United States Patent
Koutsakos et al.

(10) Patent No.: US 11,517,617 B2
(45) Date of Patent: Dec. 6, 2022

(54) METHODS AND COMPOSITIONS FOR PREVENTING INFLUENZA INFECTION

(71) Applicant: THE UNIVERSITY OF MELBOURNE, Victoria (AU)

(72) Inventors: Marios Koutsakos, Victoria (AU); Katarzyna Kedzierska, Victoria (AU); E. Bridie Clemens, Victoria (AU); Luca Hensen, Victoria (AU)

(73) Assignee: The University of Melbourne, Victoria (AU)

( * ) Notice: Subject to any disclaimer, the term of this patent is extended or adjusted under 35 U.S.C. 154(b) by 0 days.

(21) Appl. No.: 16/645,067

(22) PCT Filed: Sep. 7, 2018

(86) PCT No.: PCT/AU2018/050971
§ 371 (c)(1),
(2) Date: Mar. 6, 2020

(87) PCT Pub. No.: WO2019/046901
PCT Pub. Date: Mar. 14, 2019

(65) Prior Publication Data
US 2020/0368345 A1    Nov. 26, 2020

(30) Foreign Application Priority Data
Sep. 8, 2017  (AU) .............. 2017903652

(51) Int. Cl.
*A61K 39/145* (2006.01)
*C07K 7/06* (2006.01)
*C07K 7/08* (2006.01)

(52) U.S. Cl.
CPC .............. *A61K 39/145* (2013.01); *C07K 7/06* (2013.01); *C07K 7/08* (2013.01)

(58) Field of Classification Search
None
See application file for complete search history.

(56) References Cited

U.S. PATENT DOCUMENTS

2009/0191233 A1 * 7/2009 Bonnet ............... C07K 14/005
424/194.1

FOREIGN PATENT DOCUMENTS

| EP | 2368899 | 9/2011 |
| WO | 2008/039267 | 4/2008 |
| WO | 2009/027688 | 3/2009 |
| WO | 2015/033137 | 3/2015 |

OTHER PUBLICATIONS

The International Search Report (ISR) with Written Opinion for PCT/AU2018/050971 dated Nov. 13, 2018, pp. 1-16.
Stoloff, Gregory A. et al. "Synthetic multi-epitope peptides identified in silica induce protective immunity against multiple influenza serotypes" European Journal of Immunology (2007) vol. 37(9), p. 2441-2449.
Tan, Paul ThiamJoo et al. "Conservation and diversity of influenza A H1N1 HLArestricted T cell epitope candidates for epitope-based vaccines." PloS one (2010) vol. 5(1), p. e8754.

* cited by examiner

*Primary Examiner* — Benjamin P Blumel
(74) *Attorney, Agent, or Firm* — McDonnell Boehnen Hulbert & Berghoff LLP

(57) ABSTRACT

The present invention provides novel methods and compositions for use in preventing infection with at least one type of influenza virus, including the use of peptides or compositions comprising a peptide comprising, consisting or consisting essentially of an amino acid sequence selected from the group of sequences as shown in SEQ ID Nos: 1 to 53, or functional derivatives or homologues thereof.

18 Claims, 39 Drawing Sheets
Specification includes a Sequence Listing.

| FluA Epitope | HLA Restriction | IAV sequence | IBV sequence | ICV sequence |
|---|---|---|---|---|
| PB1 591-599 | A1 | VSDGGPNLY | VADGGPNIY | *too low to identify* |
| PB1 30-38 | A1 | YSHGTGTGY | YSHGTGTGY | MSHGSSTKY |
| PB1 407-415 | A2 | MMMGMFNML | MMMGMFNML | MLMGMFNML |
| PB1 412-421 | A2 | FNMLSTVLGV | FNMLSTVLGV | FNMLSTVLGV |
| PB1 413-421 | A2 | NMLSTVLGV | NMLSTVLGV | NMLSTVLGV |
| PB1 471-480 | A3/A11/A31/A68 | KLVGINMSKK | KLLGINMSKK | KLIGINMSLE |
| PB1 540-548 | B7 | GPATAQMAL | GPATAQTAI | SPSTALMAL |
| PB1 490-497 | B44 | FEFTSFFY | FEFTSMFY | FEFTSMFF |
| NP 338-346 | B37 | FEDLRVLSF | YEDLRVLSA | *too low to identify* |

Figure 1b n=66

| Cohort | Age (median) | Days after ILI onset (median) |
| --- | --- | --- |
| Healthy (n=14-24) | 22-60 (45) | N/A |
| IAV (n=16) | 13-77 (41.5) | 0-11 (6) |
| IBV (n=8) | 6-33 (22.5) | 0-16 (11) |

PB1$_{413-421}$

BHA$_{543}$

Figure 12

METHODS AND COMPOSITIONS FOR PREVENTING INFLUENZA INFECTION

CROSS-REFERENCE TO RELATED APPLICATION

This application is a U.S. national phase of International Application No. PCT/AU2018/050971, filed on Sep. 7, 2018, which claims priority to Australian Patent Application No. 2017903652, filed Sep. 8, 2017, both of which are incorporated by reference herein in their entirety.

FIELD OF THE INVENTION

The present invention relates to novel methods and compositions for preventing influenza infection or symptoms of influenza infection in a subject.

RELATED APPLICATION

This application claims priority from Australian provisional application AU 2017903652, the contents of which are hereby incorporated by reference in their entirety.

BACKGROUND OF THE INVENTION

Despite widespread vaccination initiatives, influenza remains a major cause of mortality and morbidity. Each year between 250,000 and 500,000 deaths are attributed to seasonal influenza, with associated annual healthcare costs in the US alone reaching billions of dollars.

Vaccination programmes have been developed and are aimed at minimising the burden of seasonal influenza, with the majority of vaccines designed to generate a protective antibody-mediated immunity. However, the vaccines currently utilised are highly strain specific, especially in the case of inactivated (killed) virus vaccines.

Influenza viruses can evade established protective immune responses by two distinct mechanisms: either via the gradual antigenic drift of viral surface epitopes, or less commonly, through the emergence of new viral strains arising from re-assortment of influenza virus RNA from different strains in a common host. As such, the success of seasonal vaccination programmes is dependent upon both the reliable predictive modelling of strain circulation and the lack of viral coat protein mutation enabling immune evasion during a flu season.

T cells may also mediate protection or limit the severity of influenza-associated illness. Pre-existing T cell responses have been shown to reduce influenza A severity in the context of existing antibodies although little, if anything is known about T cell responses to influenza Type B or Type C.

There remains a need for new or improved agents for use in the prevention and/or treatment of influenza viral infections.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention is concerned with peptides, and compositions and vaccines containing such peptides, which are useful in various methods for inducing T cell immunity to at least one type of influenza virus.

The present invention provides a composition comprising a peptide comprising, consisting essentially of, or consisting of an amino acid sequence selected from the group of sequences as shown in SEQ ID Nos: 1 to 53, or functional derivatives or homologues thereof.

In any embodiment of the invention, the composition may comprise a peptide that comprises two or more sequences as shown in SEQ ID Nos: 1 to 53.

Further, the invention provides a composition comprising two or more peptides comprising two or more amino acid sequences as shown in any one of SEQ ID Nos: 1 to 53, or functional derivatives or homologues thereof. For example, the composition may comprise a first peptide comprising, consisting or consisting essentially of an amino acid sequence selected from the group of sequences consisting of SEQ ID Nos: 1 to 4 and 25 to 42, and a second peptide comprising, consisting or consisting essentially of an amino acid sequence selected from the group of sequences consisting of SEQ ID Nos: 5 to 19, 25, 26 or 43 to 53 or functional derivatives or homologues of said peptides.

In preferred embodiments, the present invention provides a composition comprising at least one peptide comprising, consisting or consisting essentially of an amino acid sequence selected from the group of sequences consisting of SEQ ID Nos: 1 to 4, or functional derivatives or homologues of said peptides.

Alternatively, the invention provides a composition comprising at least one peptide comprising, consisting or consisting essentially of an amino acid sequence selected from the group of sequences consisting of SEQ ID Nos: 5 to 19, and 43 to 53 or functional derivatives or homologues of said peptides.

Still further, the invention provides a composition comprising at least one peptide comprising, consisting or consisting essentially of an amino acid sequence selected from the group of sequences consisting of SEQ ID Nos: 20 to 26, or functional derivatives or homologues of said peptides.

In any embodiment, the composition comprising a peptide comprising, consisting or consisting essentially of the amino acid sequence selected from SEQ ID Nos: 1 to 4, SEQ ID Nos: 5 to 19, 43 to 53, and SEQ ID Nos: 20 to 24, may further comprise at least one peptide comprising an amino acid sequence selected from the group of sequences consisting of SEQ ID Nos: 25 to 42, or functional derivatives or homologues of said peptides.

In any embodiment, the composition comprises a peptide that comprises, consists or consists essentially of:
a) a first peptide comprising an amino acid sequence selected from the group of sequences consisting of SEQ ID Nos: 1 to 4 and 25 to 42,
b) a second peptide comprising an amino acid sequence selected from the group of sequences consisting of SEQ ID Nos: 5 to 19, 25, 26, and 43 to 53
or functional derivatives or homologues of said peptides.

In any embodiment, the composition comprises a peptide that comprises, consists or consists essentially of:
a) a first peptide comprising an amino acid sequence selected from the group of sequences consisting of SEQ ID Nos: 1 to 4 and 25 to 42, and
b) a second peptide comprising an amino acid sequence selected from the group of sequences consisting of SEQ ID Nos: 5 to 19, 25, 26 and 43 to 53
or functional derivatives or homologues of said peptides.

Preferably the first peptide is a peptide that comprises, consists or consists essentially of an amino acid sequence selected from the group of sequences consisting of SEQ ID NOs: 1 to 4 and the second peptide comprises, consists or consist essentially of an amino acid sequence selected from the group consisting of SEQ ID NOs: 44 to 53.

Still further, the composition may comprise a peptide comprising, consisting or consisting essentially of an amino acid sequence selected from the group of sequences consisting of SEQ ID NO: 20 to 26, or functional derivatives of homologues of said peptides.

In any embodiment, the composition may comprise at least one peptide comprising, consisting or consisting essentially of an amino acid sequence selected from the group of sequences consisting of SEQ ID NOs: 9, 11, 14, 19, 21, 25, 26, 30, 33, 34, 40 and 45 or functional derivatives or homologues of said peptides.

In any embodiment, the composition may comprise at least one peptide comprising, consisting, or consisting essentially of an amino acid sequence selected from SEQ ID NOs: 25 or 26, preferably, wherein the peptide comprises or consists or consists essentially of the sequence of SEQ ID NO: 25.

In any embodiment, the composition may comprise at least one peptide comprising, consisting or consisting essentially of an amino acid sequence selected from SEQ ID NOs: 9 or 33, preferably, wherein the peptide comprises or consists or consists essentially of the sequence of SEQ ID NO: 33.

In still further embodiments of the invention, the composition may comprise at least one peptide comprising, consisting, or consisting essentially of an amino acid sequence selected from SEQ ID NOs: 14 or 40, preferably, wherein the peptide comprises or consists or consists essentially of the sequence of SEQ ID NO: 40.

In any embodiment of the present invention, a composition as herein defined may further comprise an adjuvant. An adjuvant may be used for potentiating an immune response to the peptide contained in the composition, when the composition is utilised as a vaccine composition. Preferably, the adjuvant potentiates a cellular immune response, specifically a cytotoxic T cell response.

The compositions described herein may additionally comprise pharmaceutically acceptable excipients, diluents or carriers.

In any embodiment of the present invention, the peptides defined herein, including for use in the methods and compositions defined herein, are 60 amino acids in length or less. Preferably, each peptide is at least 7 amino acids in length. In alternative embodiments, each peptide is at least 8, 9, 10, 11, 12, 13, 14, 15, 16, 17, 18, 19, 20 or more amino acids in length, but no more than 60 amino acids in length.

In any embodiment of the present invention, the peptides defined herein are capable of binding to an HLA molecule as described herein and/or binding to a T cell receptor. Binding to an HLA molecule and/or T cell receptor can be determined using methods described herein. Preferably, the peptides are capable of activating CD8$^+$ T cells in vitro and/or in vivo.

The present invention also provides for a vaccine or immune stimulating composition for providing an immune response to an influenza virus in an individual, comprising:

an immunogen in the form of at least one peptide comprising a sequence selected from the group of sequences consisting of SEQ ID NO: 1 to 53, and an adjuvant, for potentiating the immune response in an individual to the immunogen.

The immunogen may be in the form of at least one peptide comprising, consisting or consisting essentially of an amino acid sequence selected from the group of sequences consisting of SEQ ID Nos: 1 to 4 or at least one peptide comprising, consisting or consisting essentially of an amino acid sequence selected from the group of sequences consisting of SEQ ID Nos: 5 to 8, and 43 to 53 or functional derivatives or homologues of said peptides.

Alternatively, the immunogen is in the form of at least one peptide comprising, consisting or consisting essentially of an amino acid sequence selected from the group of sequences consisting of SEQ ID Nos: 1 to 4 and at least one peptide comprising, consisting or consisting essentially of an amino acid sequence selected from the group of sequences consisting of SEQ ID NOs: 5 to 8, and 43 to 53 or functional derivatives or homologues of said peptides.

In a further embodiment, the immunogen further comprises at least one peptide comprising an amino acids sequence selected from the group consisting of any one of SEQ ID Nos: 9 to 42.

In any embodiment, the immunogen may be in the form of a first and second peptide, wherein the first peptide comprises an amino acid sequence selected from the group of sequences consisting of SEQ ID NOs: 1 to 4 and 25 to 42 and the second peptide comprises an amino acid sequence selected from the group of sequences consisting of SEQ ID NOs: 5 to 19 and 43 to 53. The vaccine or immune stimulating composition may further comprise a third peptide selected from the group of sequences consisting of SEQ ID NO: 20 to 24.

In further embodiments, the immunogen may be in the form of at least one peptide comprising, consisting or consisting of an amino acid sequence selected from the group of sequences consisting of SEQ ID Nos: 9, 11, 14, 19, 21, 25, 26, 30, 33, 34, 40 and 45, or functional derivatives or homologues of said peptides.

In a preferred embodiment, the immunogen is in the form of at least one peptide that comprises, consists or consists essentially of the amino acid sequence of SEQ ID NO: 25.

In a preferred embodiment, the immunogen is in the form of at least one peptide that comprises, consists or consists essentially of the amino acid sequence of SEQ ID NO: 33.

In a further preferred embodiment, the immunogen is in the form of at least one peptide that comprises, consists or consists essentially of the amino acid sequence of SEQ ID NO: 40.

In any embodiment, the compositions, the vaccines or immune stimulating compositions described herein comprise at least one peptide that binds to an HLA molecule selected from the group consisting of: HLA-A*02:01, HLA-A*01:01, HLA-A*03:01, HLA-A*11, HLA-A*31, HLA-A*68, HLA-A*24:02, HLA-A*26, HLA-B*7, HLA-B*27, HLA-B*37, HLA-B*44. Binding of a peptide to a HLA molecule may be determined using an assay or method as described herein.

Preferably, the sole immunogen(s) provided in the compositions, vaccines or immune stimulating compositions of the invention, is/are a peptide/s as herein described.

The present invention provides for methods of preventing an influenza infection or symptoms of influenza infection in a subject, the method comprising administering to the subject a peptide, composition or vaccine or immune stimulating composition as herein defined.

In certain embodiments, the invention provides a method of eliciting an immune response in an individual to more than one subtype of influenza, the method comprising:

administering to an individual an immune stimulating composition comprising an immunogen in the form of at least one peptide comprising, consisting or consisting essentially of an amino acid sequence selected from the group of sequences consisting of SEQ ID NO: 9, 11, 14, 19, 21, 25, 26, 30, 33, 34, 40 and 45, thereby eliciting an immune response in the individual against more than one subtype of influenza.

In one embodiment, the composition that elicits an immune response in an individual to more than one subtype of influenza comprises at least one peptide that comprises, consists or consists essentially of the amino acid sequence of SEQ ID NO: 25, 33 or 40.

In one embodiment, the composition that elicits an immune response in an individual to more than one subtype of influenza comprises at least one peptide that comprises, consists of or consists essentially of an amino acid sequence selected from the sequences of SEQ ID NO: 11, 21 and 34.

In one embodiment, the composition that elicits an immune response in an individual to more than one subtype of influenza comprises at least one peptide that comprises, consists of or consists essentially of an amino acid sequence selected from the sequences of SEQ ID NO: 19 and 39.

In one embodiment, the composition that elicits an immune response in an individual to more than one subtype of influenza comprises at least one peptide that comprises, consists of or consists essentially of an amino acid sequence selected from the sequences of SEQ ID NO: 30 and 45.

Preferably, the peptide comprises, consists or consists essentially of a sequence selected from SEQ ID NO: 25 or 26, preferably SEQ ID NO: 25.

Preferably, the peptide comprises, consists or consists essentially of a sequence selected from SEQ ID NO: 9 or 33, preferably SEQ ID NO: 33.

Preferably, the peptide comprises, consists or consists essentially of a sequence selected from SEQ ID NO: 14 or 40, preferably SEQ ID NO: 40.

In any embodiment, the influenza infection for which prevention is required is an infection with a virus selected from the group consisting of influenza Types A, B or C.

The present invention provides for methods for minimising the severity of a symptom associated with influenza infection, comprising administering to an individual in need thereof, a peptide, composition, vaccine or immune stimulating composition as herein defined, wherein the symptoms are selected from the group consisting of chills, fever, sore throat, muscle pains, severe headache, coughing, weakness/fatigue and general discomfort.

The present invention also provides for methods of immunising an individual against an influenza virus, the method comprising administering to the individual, a peptide, composition, vaccine or immune stimulating composition as herein defined.

The present invention also provides for methods of immunising an individual against at least two types of influenza, the method comprising administering to the individual, a peptide, composition, vaccine or immune stimulating composition as herein defined.

In any embodiment of the invention, the individual may be immunised against influenza types A and B. In further embodiments, the individual is immunised against influenza types A, B and C.

Preferably, the individual is immunised against at least influenza type A when the individual is provided with a composition or vaccine comprising at least one peptide that comprises, consists or consists essentially of an amino acid sequence selected from the group of sequences shown in SEQ ID NOs: 1 to 4 and 25 to 42.

Preferably, the individual is immunised against at least influenza type B when the individual is provided with a composition or vaccine comprising at least one peptide that comprises, consists or consists essentially of an amino acid sequence selected from the group of sequences shown in SEQ ID NOs: 5 to 8, 25, 26 and 43 to 53.

Preferably, the individual is immunised against at least influenza type C when the individual is provided with a composition or vaccine comprising at least one peptide that comprises, consists or consists essentially of an amino acid sequence selected from the group of sequences shown in SEQ ID NOs: 20 to 26.

Preferably, the individual is immunised against influenza types A and B when the individual is provided with a composition or vaccine composition comprising at least one peptide comprising, consisting or consisting essentially of an amino acid sequence selected from the following group: $PB1_{413-321}$: NMLSTVLGV (SEQ ID NO: 25), FNMLSTVLGV (SEQ ID NO: 26), $NP_{338-345}$: YEDLRVLSA (SEQ ID NO: 9), FEDLRVLSA (SEQ ID NO: 33), $PB1_{591-599}$: VADGGPNIY (SEQ ID NO: 14), and VSDGGPNLY (SEQ ID NO: 40).

In further embodiments, the individual is immunised against influenza types A and B when the individual is provided with a composition of vaccine composition comprising at least one peptide comprising, consisting or consisting essentially of an amino acid sequence selected from the following group: $PB1_{540-549}$: GPATAQTAI (SEQ ID NO: 11), SPSTALMAL (SEQ ID NO: 21) and GPATAQMAL (SEQ ID NO: 34).

In further embodiments, the individual is immunised against influenza types A and B when the individual is provided with a composition of vaccine composition comprising at least one peptide comprising, consisting or consisting essentially of an amino acid sequence selected from the following group: $PB1_{41-49}$: DTVIRTHEY (SEQ ID NO: 19) and DTVNRTHQY (SEQ ID NO: 39).

In further embodiments, the individual is immunised against influenza types A and B when the individual is provided with a composition of vaccine composition comprising at least one peptide comprising, consisting or consisting essentially of an amino acid sequence selected from the following group: $PB2_{549-557}$: TYQWIIRNW (SEQ ID NO: 30) and TYQWVLKNL (SEQ ID NO: 45).

In certain embodiments, the individual is immunised against influenza types A and B when the individual is provided with a composition or vaccine composition comprising at least one peptide comprising amino acid sequence selected from the following group: NMLSTVLGV (SEQ ID NO: 25), FNMLSTVLGV (SEQ ID NO: 26), YEDLRVLSA (SEQ ID NO: 9), FEDLRVLSA (SEQ ID NO: 33), RDGFVSNF (SEQ ID NO: 12), RYGFVANF (SEQ ID NO: 35), FYRDGFVSNF (SEQ ID NO: 13), GPATAQTAI (SEQ ID NO: 11), GPATAQMAL (SEQ ID NO: 34), SPSTALMAL (SEQ ID NO: 21), KLLGINMSKK (SEQ ID NO: 10), KLIGINMSLE (SEQ ID NO: 20), KLVGINMSKK (SEQ ID NO: 32), VADGGPNIY (SEQ ID NO: 14), VSDGGPNLY (SEQ ID NO: 40), FEFTSMFY (SEQ ID NO: 15), FEFTSFFY (SEQ ID NO: 41), FEFTSMFF (SEQ ID NO: 24), RRAIATAGI (SEQ ID NO: 16), RRAIATPGM (SEQ ID NO: 22), CENLEQSGL (SEQ ID NO: 17), CEKLKESGL (SEQ ID NO: 23), CEKLEQSGL (SEQ ID NO: 37), GMFEFTSMFY (SEQ ID NO: 18), FEFTSMFF (SEQ ID NO: 24), DTVIRTHEY (SEQ ID NO: 19) AND DTVNRTHQY (SEQ ID NO: 39).

In yet further embodiments, the individual is immunised against influenza types A, B and C when the individual is provided with a composition or vaccine composition comprising at least one peptide having the following amino acid sequence: NMLSTVLGV (SEQ ID NO: 25) FNML-STVLGV (SEQ ID NO: 26), GPATAQTAI (SEQ ID NO: 11), SPSTALMAL (SEQ ID NO: 21), GPATAQMAL (SEQ ID NO: 34), KLLGINMSKK (SEQ ID NO: 10), KLIG-INMSLE (SEQ ID NO: 20), KLVGINMSKK (SEQ ID NO: 32), FEFTSMFY (SEQ ID NO: 15), FEFTSFFY (SEQ ID NO: 41), FEFTSMFF (SEQ ID NO: 24), CENLEQSGL (SEQ ID NO: 17), CEKLKESGL (SEQ ID NO: 23), and CEKLEQSGL (SEQ ID NO: 37).

Preferably, the individual is immunised against influenza types A, B and C when the individual is provided with a composition or vaccine composition comprising at least one peptide having the following amino acid sequence:

PB1$_{413-321}$: NMLSTVLGV (SEQ ID NO: 25), FNML-STVLGV (SEQ ID NO: 26).

The present invention also provides a method of inducing T cell immunity to an influenza virus in an individual, the method comprising administering to the individual, a peptide, composition, vaccine or immune stimulating composition as herein defined.

In preferred embodiments, the T cell immunity is effective to mount an immune response for more than one type of influenza virus.

The present invention further provides methods of inducing a cytotoxic T cell response in an individual, the method comprising administering to the individual, a peptide, composition, vaccine or immune stimulating composition as herein defined.

The cytotoxic T cell response may be to Influenza A or Influenza B. Alternatively, the cytotoxic T cell response is to Influenza A and Influenza B. Still further, the cytotoxic T cell response is to Influenza A, Influenza B and Influenza C.

Preferably, the only immunogen used in the methods of the present invention is a peptide immunogen, including a peptide immunogen as herein described. The skilled person will understand this to mean that the methods of the invention are not directed to administration of inactivated (killed) intact or lysed virus.

The present invention provides for use of a peptide comprising, consisting essentially of or consisting of an amino acid sequence selected from the group consisting of SEQ ID NO: 1 to 53, or functional derivatives or homologues thereof, in the manufacture of a medicament for preventing an infection, or symptom of influenza infection in a subject.

The medicament is preferably for prevention of infection or symptoms of infection with more than one type of influenza in the subject.

The medicament preferably comprises one or more peptides, or combinations of peptides as herein described. Preferably, the only immunogen present in the medicament is a peptide immunogen as herein described.

In any embodiment of the present invention, the vaccines, compositions or methods are for treating or preventing infection in an individual who is susceptible to infection with an influenza virus.

The present invention also provides for isolated, recombinant, substantially purified or synthetic peptides comprising, consisting essentially of or consisting of an amino acid sequence selected from the group consisting of SEQ ID NO: 1 to 53 or functional derivatives or homologues thereof.

The present invention also provides a kit comprising a composition comprising a peptide that comprises, consists or consists essentially of an amino acid sequence selected from the group of sequences consisting of SEQ ID NO: 1 to 53, wherein optionally the kit comprises one or more cytokines and/or adjuvants in sealed containers.

Preferably, the kit comprises a label or package insert indicating that the composition is used for immunising an individual, optionally wherein the label or package insert includes instructions for use.

In any embodiment of the compositions, vaccines, methods, uses or kits described herein, the peptide is not a peptide comprising, consisting or consisting essentially of the sequence of SEQ ID NO: 32.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

Figure 12:
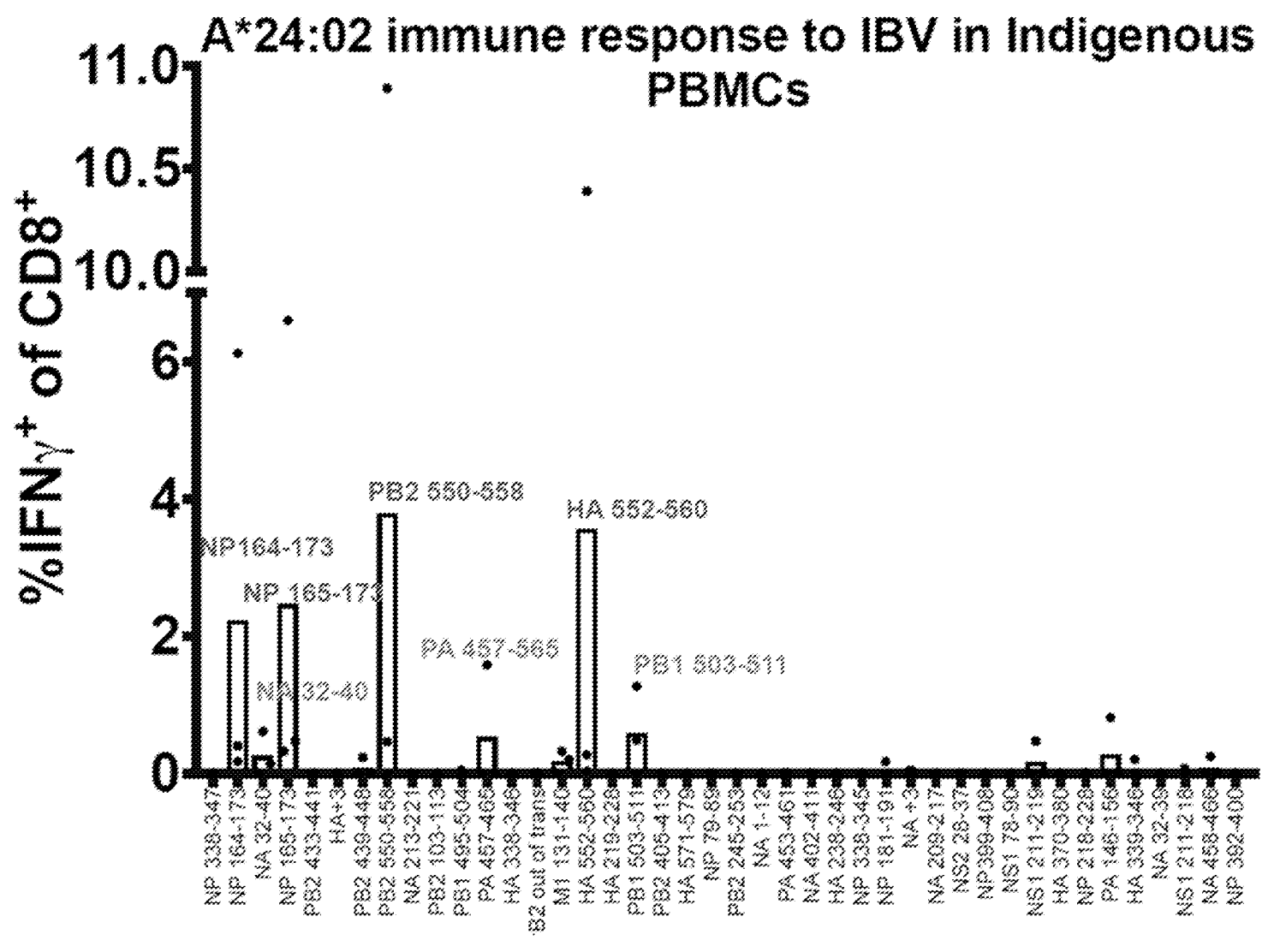

FIG. 12 Identification of novel A24 influenza B epitopes in Indigenous donors. Peripheral blood mononuclear cells (PBMCs) of Indigenous A*24:02+ donors were stimulated with pools of the identified IBV peptides and expanded for 15 days in the presence of IL-2. On day 15, PBMCs were re-stimulated with single peptide pulsed antigen presenting cells for 5 hrs in presence of protein transport inhibitors and cells stained for surface markers and intracellular cytokines. Histogram shows of % IFNγ positive CD8 T cells following re-stimulation.

DETAILED DESCRIPTION OF THE EMBODIMENTS

Figure 1A:
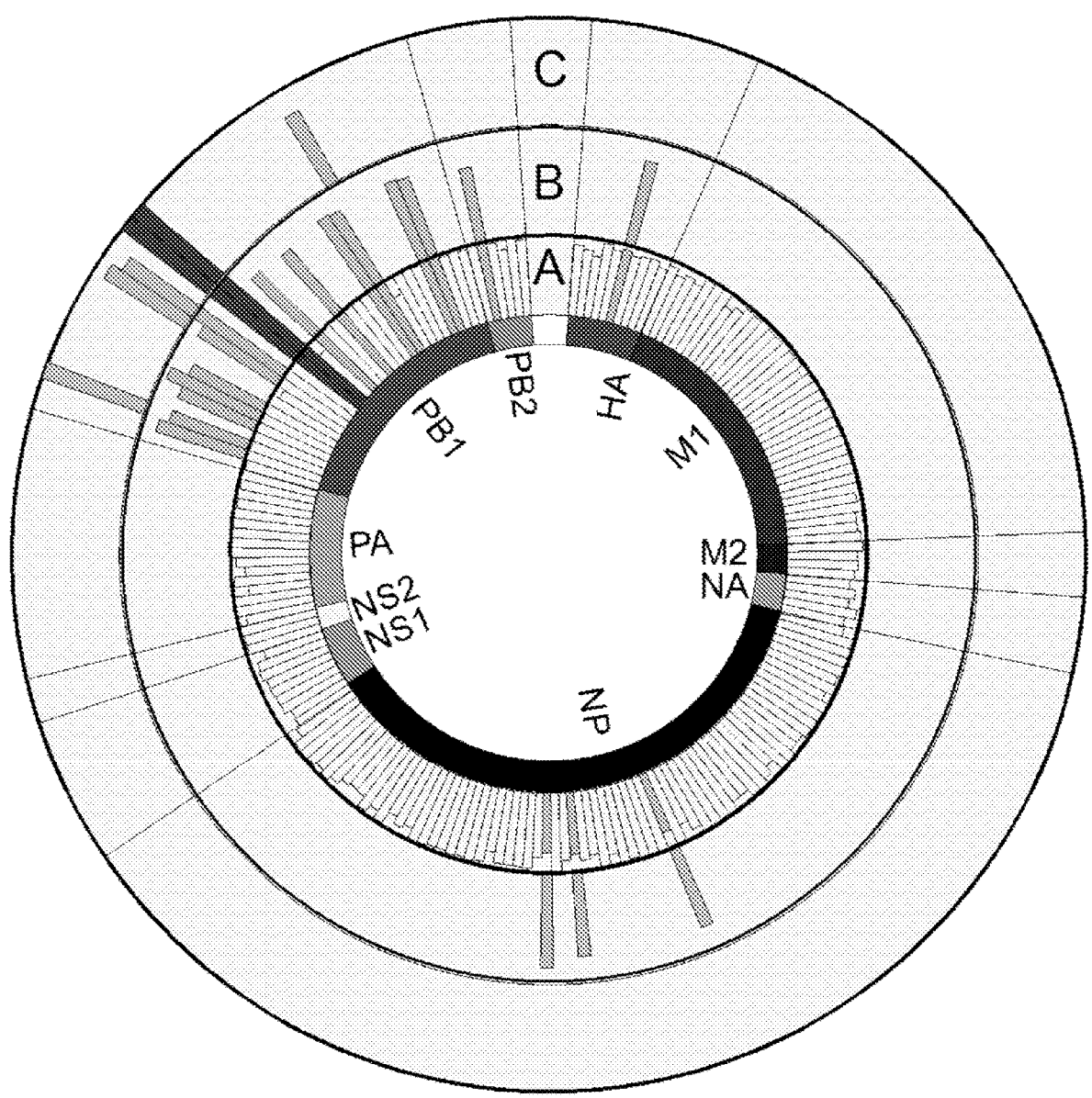
FIG. 1 Identification of highly conserved CD8+ T cell epitopes across Influenza A (IAV), Influenza B (IBV) and Influenza C (ICV). a) Conservation of known IAV epitopes in IBV and ICV. The bars indicate the percent conservation (average amino acid identity) of each peptide across the three types of viruses in the indicated number of sequences. b) Highly conserved peptides across IAV, IBV and ICV types were selected for dissection of cross-reactive CD8+ T cell responses. (c) Immunogenicity of memory CD8+ T cells directed at conserved peptides in healthy adults. PBMCs were cultured with the peptides (as outlined in B) for ~10 days and responses were assessed in an IFN-γ ICS. Frequency of IFNγ+CD8+ T cells after subtracting 'no peptide' control and responding donors are shown. Dots indicate individual donors, median and interquartile range (IQR) shown. (n=3-5). d) Conservation of PB1$_{413-421}$ peptide in Orthomyxoviruses. Alignment of PB1 sequences derived from viruses representing each genus is shown. The box indicates the PB1$_{413-421}$ peptide. (e) A2/PB1$_{413-421}$-mediated cross-reactivity across IAV, IBV and ICV. PBMCs were stimulated with either virus for ~10 days and responses to the peptide were assessed in an ICS. A2/PB1$_{413-421}$+CD8+ T cell responses measured directly ex-vivo by ICS are shown for comparison. Representative concatenated FACS plots for IFNγ production are shown. Data points indicate individual donors, median and IQR. (n=6). Statistical significance was determined using the Mann-Whitney test, *p<0.05, **p<0.005. (f) B37/NP$_{338-345}$-mediated and (g) A1/PB1$_{591-599}$-mediated cross-reactivity across IAV and IBV. On ~day 10 of peptide culture, CD8+ T cell responses to either IAV or IBV variants were assessed by ICS. Dots indicate individual donors and bars indicate the mean (n=3-4). (e-f) 'No peptide' control was subtracted.

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

Influenza (commonly referred to as "the flu") is an infectious disease caused by RNA viruses of the family Orthomyxoviridae (the influenza viruses) that affects birds and mammals. The most common symptoms of the disease are chills, fever, sore throat, muscle pains, severe headache, coughing, weakness/fatigue and general discomfort.

The influenza viruses make up three of the five genera of the family Orthomyxoviridae. Influenza Type A and Type B viruses co-circulate during seasonal epidemics and can cause severe influenza infection. Influenza Type C virus infection is less common but can be severe and cause local epidemics.

Influenza Type A virus can be subdivided into different serotypes or subtypes based on the antibody response to these viruses. Influenza A viruses are divided into subtypes based on two proteins on the surface of the virus: the hemagglutinin (H) and the neuraminidase (N). There are 18 different hemagglutinin subtypes and 11 different neuraminidase subtypes. (H1 through H18 and N1 through N11 respectively.) The sub types that have been confirmed in humans are H1N1, H1N2, H2N2, H3N2, H5N1, H7N2, H7N3, H7N7, H9N2 and H10N7.

Influenza has an enormous impact on public health with severe economic implications in addition to the devastating health problems, including morbidity and even mortality. Accordingly, there is a need for therapeutic agents which can prevent infection, or reduce severity of infection in individuals.

The present inventors have identified novel peptides derived from influenza proteins which are useful for inducing an immune response to at least one influenza type. In particular, the inventors have identified novel peptides derived from Influenza Type A and Influenza Type B, which are useful in inducing a cellular immune response, preferably T cell, to these influenza types. In particular, the inventors are the first to identify Influenza B peptides that are naturally presented on HLA molecules, and can be used to provide immunoprotection in individuals against this type of influenza.

As such, the present invention provides for peptides, compositions comprising said peptides, including vaccines, which are useful for inducing a T cell response to either Influenza Type A or Influenza Type B.

The present invention relates to peptides useful for inducing cell mediated immunity to influenza. In particular the present invention relates to peptides that are useful for provoking a cytotoxic T cell and/or memory T cell response, such as an enhanced CD8+ T-cell response. The peptides of the present invention can be used to induce T cell immunity to influenza and used in the treatment or prophylaxis of an influenza infection, especially in patients who are immunologically naive to an influenza virus.

In certain aspects of the invention, the inventors have identified peptides which, when presented on specific HLA alleles, elicit robust, numerically prominent, and highly functional T cell responses. Thus, a further advantage of the peptides and compositions of the present invention, is the extensive coverage provided across ethnicities and the ability to be able to immunise a broad cross-section of the global population against different types of Influenza. In particular, because other studies use whole proteins or large peptide segments with limited knowledge of the antigenic peptides encompassed within those regions, the resulting compositions have likely limited population coverage, and in particular, are unlikely to be useful in Indigenous and Asian populations. In contrast, the peptides and compositions provided in the present invention provide for broader coverage across many ethnicities, including amongst Indigenous and Asian populations worldwide.

Advantageously, in certain embodiments, certain peptides of the present invention have been found to provide cross-reactive T cell responses, meaning the peptides can generate a cellular immune response that will abrogate the consequences of infection with different influenza types, subtypes and strains. Certain peptides of the invention are therefore useful for inducing cell mediated immunity to more than one type of influenza, including several influenza strains or preferably substantially all influenza types and strains. In particular, the present inventors have shown that certain peptides disclosed herein, may be useful for providing immunity to at least Influenza Type A, preferably to Influenza Types A and B, more preferably to Influenza Types A, B and C.

Peptides

The present inventors have identified a number of peptides, as shown in the Table 1 below, which can be used in accordance with the methods and compositions described further herein:

TABLE 1

Peptides of the present invention

| Amino acid sequence | Peptide name | Source of peptide (Influenza A/B/C) | SEQ ID NO: | Exemplary HLA presentation |
|---|---|---|---|---|
| NLPFDRTTI | $NP_{417-425}$ | A | 1 | A24 |
| DVNPTLLFL | $PB1_{2-10}$ | A | 2 | A24 |
| SFSFGGFTF | $PB2_{322-330}$ | A | 3 | A24 |
| RYGPALSI | $PB2_{703-710}$ | A | 4 | A24 |
| SLNDDGLDNHTILL | $HA_{538-551}$ | B | 5 | A2 |
| GLDNHTILL | $HA_{543-551}$ | B | 6 | A2 |
| VLSQFGQEHRL | $NS1_{264-274}$ | B | 7 | A3 |
| SQFGQEHRL | $NS1_{266-274}$ | B | 8 | A3 |
| YEDLRVLSA | $NP_{394-401}$ | B | 9 | B37 |
| KLLGINMSKK | $PB1_{470-479}$ | B | 10 | A3/A11/A31/A68 |
| GPATAQTAI | $PB1_{539-547}$ | B | 11 | B7 |
| RDGFVSNF | $PB1_{497-504}$ | B | 12 | A24 |
| FYRDGFVSNF | $PB1_{495-504}$ | B | 13 | A24 |
| VADGGPNIY | $PB1_{591-599}$ | B | 14 | A1 |
| FEFTSMFY | $PB1_{490-497}$ | B | 15 | B44 |
| RRAIATAGI | $PB1_{238-246}$ | B | 16 | B27 |
| CENLEQSGL | $PB1_{263-271}$ | B | 17 | B44 |
| GMFEFTSMFY | $PB1_{487-496}$ | B | 18 | A3 |
| DTVIRTHEY | $PB1_{41-49}$ | B | 19 | A26 |
| KLIGINMSLE | $PB1_{472-481}$ | C | 20 | A3 |
| SPSTALMAL | $PB1_{541-549}$ | C | 21 | B7 |
| RRAIATPGM | $PB1_{240-248}$ | C | 22 | B27 |
| CEKLKESGL | $PB1_{265-273}$ | C | 23 | B44 |
| FEFTSMFF | $PB1_{490-497}$ | C | 24 | B44 |
| NMLSTVLGV | $PB1_{413-421}$ | A/B/C | 25 | A2 |
| FNMLSTVLGV | $PB1_{412-421}$ | A/B/C | 26 | A2 |
| YYLEKANKI | $PA_{130-138}$ | A | 27 | A24 |
| SYLIRALTL | $PB1_{216-224}$ | A | 28 | A24 |
| SYINRTGTFEF | $PB1_{482-492}$ | A | 29 | A24 |
| TYQWIIRNW | $PB2_{549-557}$ | A | 30 | A24 |
| TYQWIIRNWET | $PB2_{549-559}$ | A | 31 | A24 |
| KLVGINMSKK | $PB1_{471-480}$ | A | 32 | A24 |
| FEDLRVLSA | $NP_{338-345}$ | A | 33 | B37 |

TABLE 1-continued

Peptides of the present invention

| Amino acid sequence | Peptide name | Source of peptide (Influenza A/B/C) | SEQ ID NO: | Exemplary HLA presentation |
|---|---|---|---|---|
| GPATAQMAL | PB1$_{540-549}$ | A | 34 | B7 |
| RYGFVANF | PB1$_{498-505}$ | A | 35 | A24 |
| RRAIATPGM | PB1$_{238-246}$ | A | 36 | B27 |
| CEKLEQSGL | PB1$_{263-271}$ | A | 37 | B44 |
| GTFEFTSFFY | PB1$_{488-497}$ | A | 38 | A3 |
| DTVNRTHQY | PB1$_{41-49}$ | A | 39 | A26 |
| VSDGGPNLY | PB1$_{591-599}$ | A | 40 | A1 |
| FEFTSFFY | PB1$_{490-497}$ | A | 41 | B44 |
| GILGFVFVL | M1$_{58-66}$ | A | 42 | A2 |
| YLNPGNYSM | M1$_{132-140}$ | B | 43 | A2 |
| IYHPGGNKL | PB2$_{245-253}$ | B | 44 | A24 |
| TYQWVLKNL | PB2$_{550\_558}$ | B | 45 | A24 |
| KYVLFHTSL | PA$_{457-465}$ | B | 46 | A24 |
| IYFSPIRVTF | NP$_{164-173}$ | B | 47 | A24 |
| YFSPIRVTF | NP$_{165-173}$ | B | 48 | A24 |
| AAYEDLRVL | NP$_{392-400}$ | B | 49 | A24 |
| LYSDILLKF | NA$_{32-40}$ | B | 50 | A24 |
| TYHSYANNI | NA$_{213-221}$ | B | 51 | A24 |
| YYSTAASSL | HA$_{552-560}$ | B | 52 | A24 |
| NFAMELPSF | PB1$_{503-511}$ | B | 53 | A24 |

In Table 1 above, and throughout this specification, the amino acid residues are designated by the usual IUPAC single letter nomenclature. The single letter designations may be correlated with the classical three letter designations of amino acid residues. The full names of the amino acids are as follows: alanine (A or Ala), cysteine (C or Cys), aspartic acid (D or Asp), glutamic acid (E or Glu). phenylalanine (F or Phe), glycine (G or Gly), histidine (H or His), isoleucine (I or Ile), lysine (K or Lys), leucine (L or Leu), methionine (M or Met), asparagine (N or Asn), proline (P or Pro), glutamine (Q or Gin), arginine (R or Arg), serine (S or Ser), Threonine (T or Thr), tryptophan (W or Trp), tyrosine (Y or Tyr) and valine (V or Val).

As used herein, the term "peptide" refers to a short sequence of amino acids and includes oligopeptides and polypeptides. These terms are therefore used interchangeably herein.

It will be appreciated that where the present invention concerns the use of compositions, immune stimulating compositions, vaccines of various peptides, or methods of use involving the peptides, the peptides can be provided in various forms. For example, in certain embodiments, the compositions of the invention may include a plurality of peptide molecules consisting essentially of the sequences provided in Table 1. Alternatively, the compositions may contain longer peptide molecules, or polypeptides which comprise any one of the sequences listed in Table 1. Still further, the compositions may comprise a plurality of polypeptides, wherein each polypeptide comprises two or more of the peptides provided in Table 1.

Accordingly, a peptide of the invention may have a length, in the range of from about 7 to 60 amino acids, typically from about 9 to 50, more typically from about 9 to 40 and more typically from about 9 to 30 amino acids, for example from about 10 to 20 amino acids, although these lengths are not intended to be limiting. In some embodiments the peptide may have a length of from 7, 8, 9 or 10 amino acids up to 11, 12, 13, 14, 15, 16, 17, 18, 19 or 20 consecutive amino acids.

The present invention also contemplates the use of fusions or conjugates of any peptide of the invention, whereby a peptide of the invention is conjugated or fused to a carrier moiety to facilitate delivery or improve stability and/or solubility. As is known in the art, a carrier is a substance that may be conjugated to a peptide epitope thereby enhancing immunogenicity. Some carriers do this by binding to multiple peptides so as to provide an antigen of increased molecular weight to the host in which the immune response is to be developed. Preferred carriers include bacterial toxins or toxoids. Other suitable carriers include the *N. meningitides* outer membrane protein, albumin such as bovine serum albumin, synthetic peptides, heat shock proteins, KLH, Pertussis proteins, protein D from *H. influenza* and toxin A, B or C from *C. difficile*. When the carrier is a bacterial toxin or toxoid, diphtheria or tetanus toxoids are preferred. Preferably the carrier contains functional groups that can react with the peptide of the invention, or may be modified to be capable of reacting with the peptide.

A peptide according to the present invention may be a synthetic peptide. Thus, the peptides may be obtained synthetically, for example by the production of synthetic DNA and expression there from. Methods for the production of synthetic peptides are well known in the art. Peptides can be designed using software, for example the Los Alamos National Library web-based software PeptGen (http://www.hiv.lanl,gov/content/sequence/PEPTGEN/peptgen.html), and synthesised using various commercially available platforms, for example using the proprietary PEPscreen technology from Sigma-Aldrich. Peptides can alternatively be produced recombinantly. Peptides for use in the invention are typically in a purified form. Using these techniques, the person skilled in the art would have no difficulty in providing peptides in accordance with the invention.

The present invention also contemplates the use of homologs to any one or more of the peptides listed in Table 1. In a preferred embodiment, a homolog will have at least 80% or more sequence identity to a peptide listed in Table 1. As used herein the term "identity" is as known in the art and is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

The skilled person will be familiar with the use of a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100), The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes. Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See http://www.ncbi.rihn.nm.gov. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci, 10:3-5: and. FASTA described in Pearson and Lipman (1988) Proc. Natl. Acad. Sci. 85:2444-8, Within FASTA, ktup is a control option that sets the sensitivity and speed of the search.

Typically, the amino acid sequences of each peptide of the invention may have at least 85% identity, using the default parameters of the BLAST computer program (Atschul et al., J. Mol. Biol. 215, 403-410 (1990)) provided by HGMP (Human Genome Mapping Project), at the amino acid level, to the native amino acid sequences of influenza. More typically, the amino sequence may have at least 86%, 87%, 88%, 89%, 90%, 91%, 92%, 93%, 94%, 95%, 96%, 97%, 98% or at least 99% identity, at the amino acid level to a sequence found in the viral protein.

A peptide according to the invention may therefore be a variant of the respective sequence that is found in a viral protein. As used herein the term "variant" relates to peptides which have a similar amino acid sequence and/or which retain the same function. For instance, the term "variant" encompasses peptides that include one or more amino acid additions, deletions, substitutions or the like. The peptides of the invention retain the function of generating T cell responses.

An example of a variant of the present invention is a peptide that is the same as the native peptide, apart from the substitution of one or more amino acids with one or more other amino acids. The skilled person is aware that various amino acids have similar properties. One or more such amino acids of a peptide or protein can often be substituted by one or more other such amino acids without eliminating a desired activity of that peptide or protein.

As used herein, a functional variant or homolog of a peptide as recited in Table 1, is a peptide which retains the ability to bind to a relevant HLA molecule and activate a T cell, preferably a CD8 T cell. Preferably, the peptide is able to elicit a T cell immune response in an individual.

In one embodiment, a functional homolog of any one of the peptides defined in SEQ ID NO: 1 to 4, 12, 13, 27 to 32, 35 and 44 to 53 may bind to HLA-A*24:02, a homolog of peptides defined in SEQ ID NOs 5, 6, 25, 26, 42 and 44 may bind to HLA-A*02:01, a homolog of peptides defined in SEQ ID NO: 7, 8, 10, 18, 20 and 38 may bind to any one of HLA-A*3, HLA-A*1 HLA-A*31, and HLA-A*68; a homolog of a peptide of SEQ ID NO: 9 or 33 may bind to HLA-B*37, a homolog of a peptide of SEQ ID Nos 11, 21 and 34 will bind to HLA-B*7, a homolog of a peptide of SEQ ID NOs 14 and 40 may bind to HLA-A*1, a homolog of a peptide of SEQ ID NOs 15, 17, 23, 24, 37 and 41 may bind to HLA-B*44, a homolog of a peptide of SEQ ID NOs 16, 22 and 36 may bind to HLA B*27, and a homolog of a peptide of SEQ ID NOs 19 and 39 may bind to HLA-A*26.

The amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions.

Amino acid deletions or insertions can also be made relative to the native sequence in the viral protein. Thus, for example, amino acids which do not have a substantial effect on the activity of the peptide, or at least which do not eliminate such activity, can be deleted. Such deletions can be advantageous, particularly with longer polypeptides since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence of the native peptide can also be made. This can be done to alter the properties of a peptide for use in the present invention (e.g. to enhance antigenicity).

Amino acid changes can be made using any suitable technique e.g. by using site-directed mutagenesis or solid state synthesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

It should also be appreciated that the peptides of the present invention may be conjugated to one or more moieties such as polyethylene glycol (PEG) (Veronese F. M. (2001) Biomaterials 22, pp 405-417).

Compositions and Vaccines

The invention further provides compositions comprising the peptides defined in Table 1, including functional derivatives and variants thereof, and the use of such peptides and vaccine compositions in the treatment or prevention of influenza.

The term "vaccine composition" used herein is defined as composition used to elicit an immune response against an antigen (immunogen) within the composition in order to protect or treat an organism against disease.

In any embodiment of the invention, a vaccine may comprise at least one peptide as shown in Table 1, or functional derivatives or variants thereof. In further embodiments, the vaccine may comprise at least 2, 3 or 4 or more of these peptides, or functional variants or derivatives thereof. The skilled person will appreciate that combining 2 or more peptides in a vaccine composition, may advantageously provide for an enhanced immune response following administration of the composition, or alternatively, provide for an immune response to epitopes from more than one type of influenza.

The vaccine compositions of the invention may suitably include a pharmaceutically acceptable carrier, excipient, diluent, adjuvant, vehicle, buffer or stabiliser in addition to one or more peptides of the invention as the therapeutically or prophylactically active ingredient. Such carriers include, but are not limited to, saline, buffered saline, dextrose, liposomes, water, glycerol, polyethylene glycol, ethanol and combinations thereof.

The vaccine compositions can be adapted for administration by any appropriate route, for example by the parenteral (including subcutaneous, intramuscular, intravenous or intradermal or by injection into the cerebrospinal fluid), oral (including buccal or sublingual), nasal, topical (including buccal, sublingual or transdermal), vaginal or rectal route. Such compositions can be prepared by any method known in the art of pharmacy, for example by admixing peptides with the carrier(s) or excipient(s) under sterile conditions. Typically, the vaccine composition is adapted for administration by the subcutaneous, intramuscular, intravenous or intradermal route, typically by injection. Alternatively, the vaccine composition may be adapted for oral or nasal administration.

A pharmaceutical composition adapted for parenteral administration may be an aqueous and non-aqueous sterile injection solution which can contain anti-oxidants, buffers, bacteriostats and solutes which render the formulation substantially isotonic with the blood of the intended recipient; and aqueous and non-aqueous sterile suspensions which can include suspending agents and thickening agents. Excipients which can be used for injectable solutions include water, alcohols, polyols, glycerine and vegetable oils, for example. The composition can be presented in unit-dose or multi-dose containers, for example sealed ampoules and vials, and can be stored in a freeze-dried (lyophilized) condition requiring only the addition of the sterile liquid carried, for example water for injections, immediately prior to use. Extemporaneous injection solutions and suspensions can be prepared from sterile powders, granules and tablets.

A pharmaceutical composition adapted for oral administration, can be presented as discrete units such as capsules or tablets; as powders or granules; as solutions, syrups or suspensions (in aqueous or non-aqueous liquids; or as edible foams or whips; or as emulsions)

Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc.

For the preparation of solutions and syrups, excipients which can be used include for example water, polyols and sugars. For the preparation of suspensions, oils (e.g. vegetable oils) can be used to provide oil-in-water or water in oil suspensions.

A pharmaceutical composition adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. A suitable composition wherein the carrier is a liquid, for administration as a nasal spray or as nasal drops, may comprise an aqueous or oil solution of the active ingredient.

Pharmaceutical compositions adapted for administration by inhalation include fine particle dusts or mists that can be generated by means of various types of metered dose pressurised aerosols, nebulizers or insufflators.

A pharmaceutical composition adapted for transdermal administration may be presented as a discrete patch intended to remain in intimate contact with the epidermis of the recipient for a prolonged period of time. For example, the active ingredient can be delivered from the patch by iontophoresis as generally described in Pharmaceutical Research. 3(6):318 (1986).

A pharmaceutical composition adapted for topical administration may be formulated as an ointment, cream, suspension, lotion, powder, solution, paste, gel, spray, aerosol or oil. For infections of the eye or other external tissues, for example mouth and skin, the composition may be applied as a topical ointment or cream. When formulated in an ointment, the active ingredient can be employed with either a paraffinic or a water-miscible ointment base. Alternatively, the active ingredient can be formulated in a cream with an oil-in-water cream base or a water-in-oil base. A pharmaceutical composition adapted for topical administration to the eye may comprise eye drops wherein the active ingredient is dissolved or suspended in a suitable carrier, especially an aqueous solvent. A pharmaceutical composition adapted for topical administration in the mouth may comprise lozenges, pastilles or mouth washes.

The pharmaceutical composition may contain preserving agents, solubilising agents, stabilising agents, wetting agents, emulsifiers, sweeteners, colourants, odourants, salts (substances of the present invention can themselves be provided in the form of a pharmaceutically acceptable salt), buffers, coating agents or antioxidants.

The vaccine composition of the invention may also contain one or more other prophylactically or therapeutically active agents in addition to the at least one peptide as defined herein.

A peptide for use in the vaccine compositions of the invention may or may not be lyophilised.

The vaccine compositions of the invention may also include a pharmaceutically acceptable adjuvant in addition to the peptide(s) as defined herein. Adjuvants are added in order to enhance the immunogenicity of the vaccine composition.

Suitable adjuvants for inclusion in a vaccine composition are known in the art and include incomplete Freund's adjuvant, complete Freund's adjuvant, Freund's adjuvant with MDP (muramyldipeptide), alum (aluminium hydroxide), alum plus *Bordatella pertussis* and immune stimulatory complexes (ISCOMs, typically a matrix of Quil A containing viral proteins), QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, and MF59.

The vaccine compositions of the invention may also include or be co-administered with one or more co-stimulatory molecules, such as B7, and/or cytokines, such as an interferon or an interleukin, that can promote T cell immune response such as 11-2, IL-15, IL-6, GM-CSF, IFNγ or other cytokines promoting T cell responses. This can be done in addition to conventional adjuvant, as described above.

Dosages of the vaccine composition of the present invention can vary between wide limits, depending upon the age and condition of the individual to be treated, etc. and a physician will ultimately determine appropriate dosages to be used.

This dosage can be repeated as often as appropriate. For example, an initial dose of the vaccine may be administered and then a booster administered at a later date.

For administration to mammals, and particularly humans, it is expected that the daily dosage of the active agent will be from 1 µg/kg to 10 mg/kg body weight, typically around 10 µg/kg to 1 mg/kg body weight. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

The vaccine composition of the invention can be administered by any convenient route as described herein, such as via the intramuscular, intravenous, intraperitoneal or oral routes or by injection into the cerebrospinal fluid.

The vaccine composition of the invention can be provided in unit dosage form, will generally be provided in a sealed container and may be provided as part of a kit. Such a kit would normally (although not necessarily) include instructions for use. It can include a plurality of said unit dosage forms.

Accordingly, in yet another aspect, the present invention provides a kit of parts comprising a vaccine composition of the invention and one or more cytokines and/or adjuvants in sealed containers.

In yet another aspect, the present invention provides a kit of parts comprising a vaccine composition of the invention and one or more cytokines and/or adjuvants for separate, subsequent or simultaneous administration to a subject.

Methods of Immunising/Vaccinating

The present invention provides methods and compositions for treating or preventing infection or minimising the likelihood of infection with an influenza virus, in an individual in need thereof.

Cell mediated immunity is an immune response that does not involve antibodies, but instead involves the activation of macrophages, natural killer cells (NK), antigen-specific cytotoxic T-lymphocytes (T cells), and the release of various cytokines in response to an antigen. Activated antigen-specific cytotoxic T cells can induce apoptosis in body cells displaying epitopes of foreign antigen on their surface, such as virus-infected cells.

Following a viral infection, memory T cells, a subset of infection fighting T cells, persist. At a subsequent encounter with the same virus, pre-existing memory T cells play a key role in the immune response to the virus. Memory T cells enable a faster and stronger immune response to be mounted, resulting in an infection which is of shorter duration and with less severe and/or with a reduced number of symptoms.

The present invention also provides for methods and compositions for inducing a memory T cell immune response in an individual to an influenza virus. As such, the present invention includes methods and compositions for preventing infection with an influenza virus, minimising the likelihood of infection and/or reducing the severity and duration of influenza infection in an individual.

As used herein, the terms "treatment" or "treating" of a subject includes the application or administration of a composition of the invention to a subject (or application or administration of a compound of the invention to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

The vaccine composition of the invention can be administered to patients felt to be in greatest need thereof, for example to children or the elderly or individuals exposed to influenza virus. Timing of administration of the vaccine may be important; for example a vaccination strategy can be put in place once an outbreak of influenza has been identified, in order to prevent the spread of the virus in a community. The vaccine composition can be used in particular subsets of patients, for example those who have not already suffered from a particular type of influenza. Other individuals in need of vaccination according to the methods of the present invention, include certain indigenous populations who are identified as being of greater risk of susceptibility to influenza infection, or at risk of a greater severity of disease symptoms.

The compositions and methods of the present invention extend equally to uses in both human and/or veterinary medicine. In particular, the vaccines of the invention are intended both for use in humans and in animals including livestock, poultry and domestic animals, for prevention or attenuation of influenza A or B disease, or preferably, for prevention or attenuation of influenza A, and B disease, more preferably for prevention or attenuation of influenza A, influenza B and influenza C disease.

In any embodiment, the vaccines, compositions and methods of the present invention include the use of a peptide comprising, consisting or consisting essentially of the amino acid sequence: NLPFDRTTI (NP$_{417-425}$ SEQ ID NO: 1).

In any embodiment, the vaccines, compositions and methods of the present invention include the use of a peptide comprising, consisting or consisting essentially of the amino acid sequence: DVNPTLLFL (PB1$_{2-10}$ SEQ ID NO: 2).

In any embodiment, the vaccines, compositions and methods of the present invention include the use of a peptide comprising, consisting or consisting essentially of the amino acid sequence: SFSFGGFTF (PB2$_{322-330}$ SEQ ID NO: 3).

In any embodiment, the vaccines, compositions and methods of the present invention include the use of a peptide comprising, consisting or consisting essentially of the amino acid sequence: RYGPALSI (PB2$_{703-710}$ SEQ ID NO: 4).

In any embodiment, the vaccines, compositions and methods of the present invention include the use of a peptide comprising, consisting or consisting essentially of the amino acid sequence: SLNDDGLDNHTILL (HA$_{538-551}$ SEQ ID NO: 5).

In any embodiment, the vaccines, compositions and methods of the present invention include the use of a peptide comprising, consisting or consisting essentially of the amino acid sequence: GLDNHTILL (HA$_{543-551}$ SEQ ID NO: 6).

In any embodiment, the vaccines, compositions and methods of the present invention include the use of a peptide comprising, consisting or consisting essentially of the amino acid sequence: VLSQFGQEHRL (NS1$_{264-274}$ SEQ ID NO: 7).

In any embodiment, the vaccines, compositions and methods of the present invention include the use of a peptide comprising, consisting or consisting essentially of the amino acid sequence: SQFGQEHRL (NS1$_{266-274}$ SEQ ID NO: 8).

In any embodiment, the vaccines, compositions and methods of the present invention include the use of a peptide comprising, consisting or consisting essentially of the amino acid sequence: YEDLRVLSA (NP$_{394-401}$ SEQ ID NO: 9).

In any embodiment, the vaccines, compositions and methods of the present invention include the use of a peptide comprising, consisting or consisting essentially of the amino acid sequence: KLLGINMSKK (PB1$_{470-479}$ SEQ ID NO: 10).

In any embodiment, the vaccines, compositions and methods of the present invention include the use of a peptide comprising, consisting or consisting essentially of the amino acid sequence: GPATAQTAI (PB1$_{539-547}$ SEQ ID NO: 11).

In any embodiment, the vaccines, compositions and methods of the present invention include the use of a peptide comprising, consisting or consisting essentially of the amino acid sequence: RDGFVSNF (PB1$_{497-504}$ SEQ ID NO: 12).

In any embodiment, the vaccines, compositions and methods of the present invention include the use of a peptide comprising, consisting or consisting essentially of the amino acid sequence: FYRDGFVSNF (PB1$_{495-504}$ SEQ ID NO: 13).

In any embodiment, the vaccines, compositions and methods of the present invention include the use of a peptide comprising, consisting or consisting essentially of the amino acid sequence: VADGGPNIY (PB1$_{591-599}$ SEQ ID NO: 14).

In any embodiment, the vaccines, compositions and methods of the present invention include the use of a peptide comprising, consisting or consisting essentially of the amino acid sequence: FEFTSMFY (PB1$_{490-497}$ SEQ IDNO: 15).

In any embodiment, the vaccines, compositions and methods of the present invention include the use of a peptide comprising, consisting or consisting essentially of the amino acid sequence: RRAIATAGI (PB1$_{238-246}$ SEQ ID NO: 16).

In any embodiment, the vaccines, compositions and methods of the present invention include the use of a peptide comprising, consisting or consisting essentially of the amino acid sequence: CENLEQSGL (PB1$_{263-271}$ SEQ ID NO: 17).

In any embodiment, the vaccines, compositions and methods of the present invention include the use of a peptide comprising, consisting or consisting essentially of the amino acid sequence: GMFEFTSMFY (PB1$_{487-496}$ SEQ ID NO: 18).

In any embodiment, the vaccines, compositions and methods of the present invention include the use of a peptide comprising, consisting or consisting essentially of the amino acid sequence: DTVIRTHEY (PB1$_{41-49}$ SEQ ID NO: 19).

In any embodiment, the vaccines, compositions and methods of the present invention include the use of a peptide comprising, consisting or consisting essentially of the amino acid sequence: KLIGINMSLE (PB1$_{472-481}$ SEQ ID NO: 20).

In any embodiment, the vaccines, compositions and methods of the present invention include the use of a peptide comprising, consisting or consisting essentially of the amino acid sequence: SPSTALMAL (PB1$_{541-549}$ SEQ ID NO: 21).

In any embodiment, the vaccines, compositions and methods of the present invention include the use of a peptide comprising, consisting or consisting essentially of the amino acid sequence: RRAIATPGM (PB1$_{240-248}$ SEQ IDNO: 22).

In any embodiment, the vaccines, compositions and methods of the present invention include the use of a peptide comprising, consisting or consisting essentially of the amino acid sequence: CEKLKESGL (PB1$_{265-273}$ SEQ ID NO: 23).

In any embodiment, the vaccines, compositions and methods of the present invention include the use of a peptide comprising, consisting or consisting essentially of the amino acid sequence: FEFTSMFF (PB1$_{496-497}$ SEQ ID NO: 24).

In any embodiment, the vaccines, compositions and methods of the present invention include the use of a peptide comprising, consisting or consisting essentially of the amino acid sequence: NMLSTVLGV (PB1$_{413-421}$ SEQ IDNO: 25).

In any embodiment, the vaccines, compositions and methods of the present invention include the use of a peptide comprising, consisting or consisting essentially of the amino acid sequence: FNMLSTVLGV (PB1$_{412-421}$ SEQ ID NO:26).

In any embodiment, the vaccines, compositions and methods of the present invention include the use of a peptide comprising, consisting or consisting essentially of the amino acid sequence: YYLEKANKI (PA$_{136-138}$ SEQ ID NO: 27)

In any embodiment, the vaccines, compositions and methods of the present invention include the use of a peptide comprising, consisting or consisting essentially of the amino acid sequence: SYLIRALTL (PB1$_{216-224}$ SEQ ID NO: 28).

In any embodiment, the vaccines, compositions and methods of the present invention include the use of a peptide comprising, consisting or consisting essentially of the amino acid sequence: SYINRTGTFEF (PB1$_{482-492}$ SEQ ID NO: 29).

In any embodiment, the vaccines, compositions and methods of the present invention include the use of a peptide comprising, consisting or consisting essentially of the amino acid sequence: TYQWIIRNW (PB2$_{549-557}$ SEQ ID NO: 30).

In any embodiment, the vaccines, compositions and methods of the present invention include the use of a peptide comprising, consisting or consisting essentially of the amino acid sequence: TYQWIIRNWET (PB2$_{549-559}$ SEQ ID NO: 31).

In any embodiment, the vaccines, compositions and methods of the present invention include the use of a peptide comprising, consisting or consisting essentially of the amino acid sequence: KLVGINMSKK (PB1$_{471-480}$ SEQ ID NO: 32).

In any embodiment, the vaccines, compositions and methods of the present invention include the use of a peptide comprising, consisting or consisting essentially of the amino acid sequence: FEDLRVLSA (NP$_{338-345}$ SEQ ID NO: 33).

In any embodiment, the vaccines, compositions and methods of the present invention include the use of a peptide comprising, consisting or consisting essentially of the amino acid sequence: GPATAQMAL (PB1$_{540-549}$ SEQ ID NO: 34).

In any embodiment, the vaccines, compositions and methods of the present invention include the use of a peptide comprising, consisting or consisting essentially of the amino acid sequence: RYGFVANF (PB1$_{498-505}$ SEQ ID NO: 35).

In any embodiment, the vaccines, compositions and methods of the present invention include the use of a peptide comprising, consisting or consisting essentially of the amino acid sequence: RRAIATPGM (PB1$_{238-246}$ SEQ ID NO: 36).

In any embodiment, the vaccines, compositions and methods of the present invention include the use of a peptide comprising, consisting or consisting essentially of the amino acid sequence: CEKLEQSGL (PB1$_{263-271}$ SEQ ID NO: 37).

In any embodiment, the vaccines, compositions and methods of the present invention include the use of a peptide comprising, consisting or consisting essentially of the amino acid sequence: GTFEFTSFFY (PB1$_{488-497}$ SEQ ID NO: 38).

In any embodiment, the vaccines, compositions and methods of the present invention include the use of a peptide comprising, consisting or consisting essentially of the amino acid sequence: DTVNRTHQY (PB1$_{41-49}$ SEQ ID NO: 39).

In any embodiment, the vaccines, compositions and methods of the present invention include the use of a peptide comprising, consisting or consisting essentially of the amino acid sequence: VSDGGPNLY (PB1$_{591-599}$ SEQ ID NO: 40).

In any embodiment, the vaccines, compositions and methods of the present invention include the use of a peptide comprising, consisting or consisting essentially of the amino acid sequence: FEFTSFFY (PB1$_{490-497}$ SEQ ID NO: 41).

In any embodiment, the vaccines, compositions and methods of the present invention include the use of a peptide comprising, consisting or consisting essentially of the amino acid sequence: GILGFVFVL (M1$_{58-66}$ SEQ ID NO: 42).

In any embodiment, the vaccines, compositions and methods of the present invention include the use of a peptide comprising, consisting or consisting essentially of the amino acid sequence: YLNPGNYSM (M1$_{132-140}$ SEQ ID NO: 43).

In any embodiment, the vaccines, compositions and methods of the present invention include the use of a peptide comprising, consisting or consisting essentially of the amino acid sequence: IYHPGGNKL (PB2$_{245-253}$ SEQ ID NO: 44).

In any embodiment, the vaccines, compositions and methods of the present invention include the use of a peptide comprising, consisting or consisting essentially of the amino acid sequence: TYQWVLKNL (PB2$_{550-558}$ SEQ ID NO: 45).

In any embodiment, the vaccines, compositions and methods of the present invention include the use of a peptide comprising, consisting or consisting essentially of the amino acid sequence: KYVLFHTSL (PA$_{457-465}$ SEQ ID NO: 46).

In any embodiment, the vaccines, compositions and methods of the present invention include the use of a peptide comprising, consisting or consisting essentially of the amino acid sequence: IYFSPIRVTF (NP$_{164-173}$ SEQ ID NO: 47).

In any embodiment, the vaccines, compositions and methods of the present invention include the use of a peptide comprising, consisting or consisting essentially of the amino acid sequence: YFSPIRVTF (NP$_{165-173}$ SEQ ID NO: 48).

In any embodiment, the vaccines, compositions and methods of the present invention include the use of a peptide comprising, consisting or consisting essentially of the amino acid sequence: AAYEDLRVL (NP$_{392-400}$ SEQ ID NO: 49).

In any embodiment, the vaccines, compositions and methods of the present invention include the use of a peptide comprising, consisting or consisting essentially of the amino acid sequence: LYSDILLKF (NA$_{32-40}$ SEQ ID NO: 50).

In any embodiment, the vaccines, compositions and methods of the present invention include the use of a peptide comprising, consisting or consisting essentially of the amino acid sequence: TYHSYANNI (NA$_{213-221}$ SEQ ID NO: 51).

In any embodiment, the vaccines, compositions and methods of the present invention include the use of a peptide comprising, consisting or consisting essentially of the amino acid sequence: YYSTAASSL (HA$_{552-560}$ SEQ ID NO: 52).

In any embodiment, the vaccines, compositions and methods of the present invention include the use of a peptide comprising, consisting or consisting essentially of the amino acid sequence: NFAMELPSF (PB1$_{503-511}$ SEQ ID NO: 53).

Certain peptides of the present invention, and as shown in Table 1, have been demonstrated to provide cross protection against different strains or serotypes or subtypes of influenza because they induce cross-reactive T cell responses.

Consequently, these peptides and vaccines comprising such peptides can be used to induce cell mediated immunity against a broad spectrum of different influenza viral infections.

In one embodiment of the present invention, a composition comprising at least one peptide as shown in Table 1 is useful for providing protection (i.e., immunising an individual) against infection with an influenza virus of Type A. Preferably, the peptide has an amino acid sequence as shown in any one of SEQ ID NOs: 1 to 4, or 9, 14 or 25 to 42.

In a further embodiment, a composition comprising at least one peptide as shown in Table 1 is useful for providing protection (i.e., immunising an individual) against infection with an influenza virus of Type B. Preferably, the peptide will have an amino acid sequence as shown in any one of SEQ ID NOs: 5 to 19, 25, 26, 33, 40 or 43 to 53.

In still a further embodiment, a composition comprising at least one peptide as shown in Table 1 is useful for providing protection (i.e., immunising an individual) against infection with an influenza virus of Type C. Preferably the peptide will have an amino acid sequence as shown in any one of SEQ ID NOs: 20 to 26.

Yet further, a composition comprising at least one peptide as shown in Table 1 is useful for providing protection (i.e., immunising an individual) against infection with more than one Type of influenza virus. Preferably, the peptide will have an amino acid sequence as shown in SEQ ID NO: 9, 14, 25, 26, 33, or 40. Such a composition is useful for immunising an individual against at least influenza Types A and B. More preferably, the composition is useful for immunising an individual against infection with influenza Types A, B and C.

The skilled person will also appreciate that it is possible to combine multiple peptides in a vaccine composition as described herein. For example, in order to provide a vaccine composition for immunising an individual against influenza Type A and B, the composition may comprise at least one peptide selected from the group consisting of SEQ ID NOs: 1 to 4, or 25 to 42 and at least one peptide selected from the group consisting of SEQ ID NOs: 5 to 19, 25, 26, or 43 to 53.

The skilled person will be familiar with screening methods for determining when administration of peptides defined herein, induce a T cell response. A T cell response is indicative of inducing T cell immunity. Therefore a peptide which induces a T cell response may be useful for inclusion in a vaccine against the virus from which they are derived.

T cells which respond to peptide antigens can be CD4+ and/or CD8+ T cells. After a viral infection a subset of the activated T cells will persist as memory T cells. Therefore the memory T cells can be CD4+ and/or CD8+ T cells.

The skilled person will be familiar with methods for determining successful vaccination/immunisation with a peptide or composition as described herein. For example, the skilled person will be familiar with methods for quantifying the number of T cells specific for a given peptide following immunisation (and for determining whether there is a T cell response following subsequent challenge with influenza virus or peptides.).

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1: Cross-Reactivity Across Influenza A, B and C

The conservation of known Influenza A (IAV) CD8+ T cell epitopes was determined across Influenza B (IBV) and Influenza C (ICV). This analysis enabled identification of a set of well conserved epitopes across the three types of influenza (FIG. 1a).

The high conservation of the PB1$_{413-421}$ peptide, along with the high prevalence of HLA-A2 in the human population prompted further characterization of responses to this epitope. PB1$_{413-421}$ was determined to be conserved across IAV, IBV and ICV, as well as IDV although a substitution (L7F) present in IDV isolated (FIG. 1b). Importantly, this peptide was found to be 100% conserved in 99.86% of influenza A, B or C viruses (n=39182 sequences).

Conservation analysis of >67,000 influenza segment sequences identified 31 conserved epitopes (with >70% amino acid identity) across IAV and IBV as well as 8 epitopes across all IAV, IBV and ICV influenza types. Based on the prevalence of HLA-restricting molecules in the population and the nature of mutations within the peptide variants, 9 epitopes were selected across both HLA-A (HLA-A*01:01, HLA-A*02:01 and HLA-A*03:01/A*11:01/*31:01/A*68:02) and HLA-B (HLA-B*07:02, HLA-B*44:02 and HLA-B*37:01) alleles for further investigation (see also FIGS. 1b and 1d).

Figure 1C:
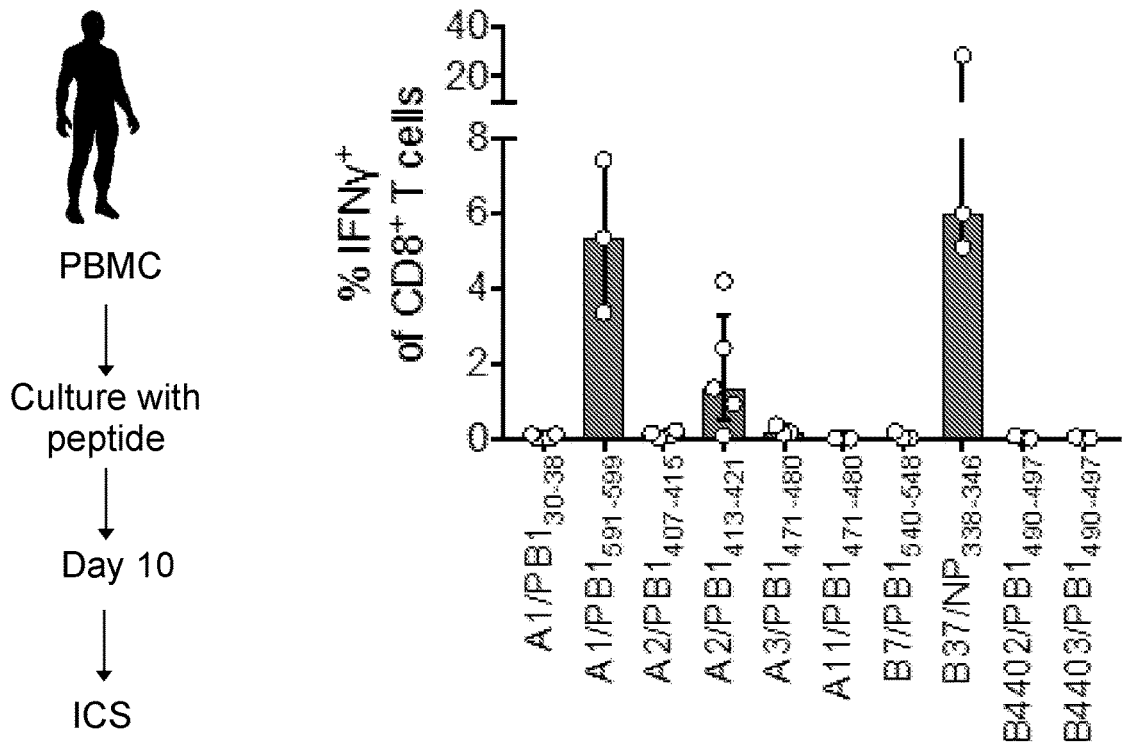
Figure 1C:
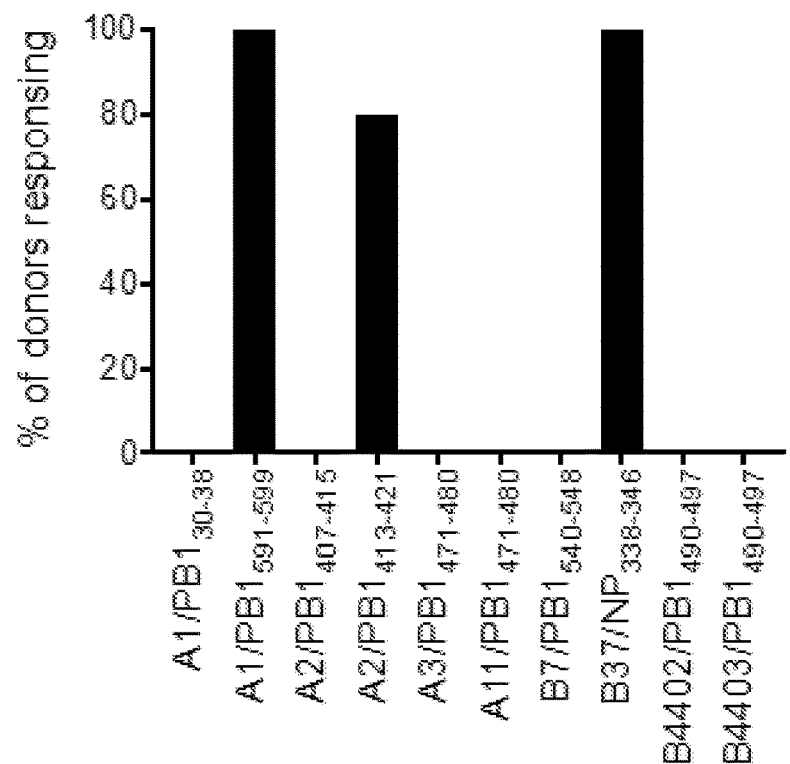
Figure 1D:
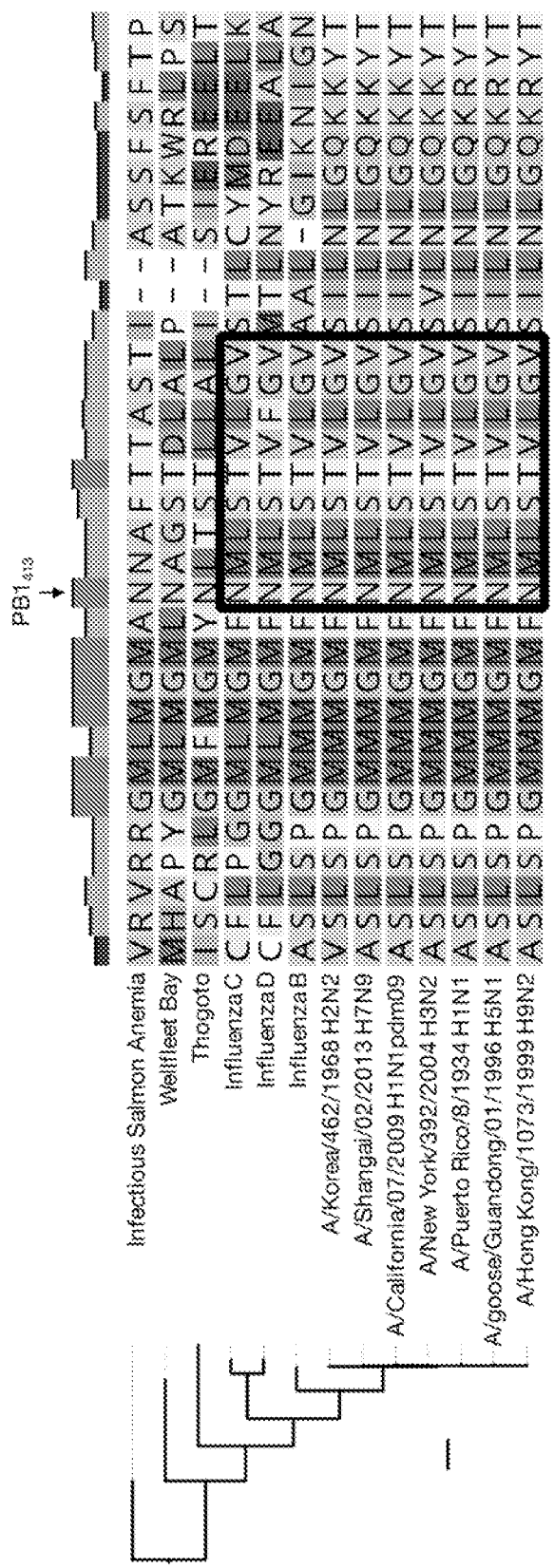

To determine CD8+ T cell immunogenicity towards these epitopes, memory CD8+ T cells within PBMCs obtained from healthy adults were probed using in vitro peptide expansion and measured IFN-γ production after peptide re-stimulation. The data indicate that three (A1/PB1$_{591}$ n=3, A2/PB1$_{413}$ n=5, B37/NP$_{338}$ n=3) out of the nine conserved CD8+ T cell epitopes recalled robust memory CD8+ T cell responses across multiple donors (FIG. 1c). These conserved CD8+ T cell peptides (PB1$_{591-599}$, PB1$_{413-421}$ and NP$_{338-345}$) are restricted by three prominent HLA molecules (HLA-A*01:01, HLA-A*02:01 and HLA-B*37:01, respectively), providing broad global coverage as ~54% of the population carry at least one of these three alleles, although some geographic regions would be underrepresented.

Figure 1E:
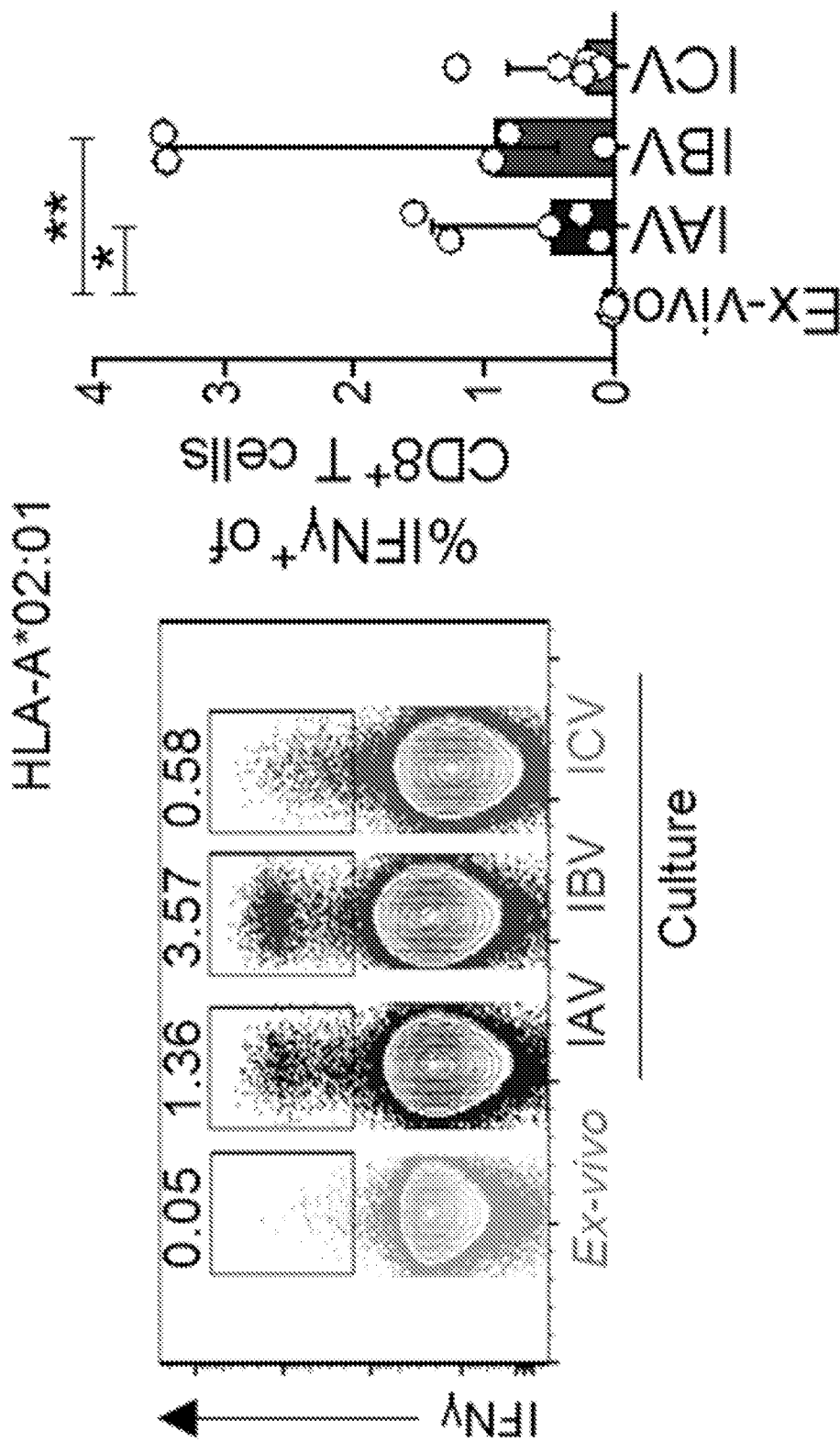

Strikingly, the PB1$_{413-421}$ peptide (PB1$_{414-422}$ in IBV and ICV; P$_{B1413}$ hereafter) was universally (>98% of sequences) conserved (average identity >99.9%) across IAV, IBV and ICV, but not in influenza D viruses where a L7F mutation was found, or other genera of the Orthomyxoviridae family like Infectious Salmon Anemia virus, Wellfleet Bay virus or Thogoto virus (FIG. 1b). To demonstrate the ability of A2/PB1$_{413}$-specific CD8+ T cells to confer cross-reactivity across IAV, IBV and ICV subtypes, PBMCs obtained from HLA-A*0201-expressing donors were stimulated in vitro with autologous PBMCs infected with either IAV, IBV or ICV, followed by measuring A2/PB1$_{413}$+CD8+ T cell responses by IFN-γ on dl 0 (n=5) (FIG. 1e). In contrast to minimal IFN-γ production towards PB1$_{413}$ peptide directly ex vivo (FIG. 1e). 10-day culture with IAV-, IBV- or ICV-infected targets markedly increased the magnitude of A2/PB1$_{413}$-specific CD8$^+$ T cells (FIG. 1e), due to expansion of A2/PB1$_{413}$$^+$CD8$^+$ T cells towards all three IAV, IBV and ICV types. Our data thus provide the first evidence that memory A2/PB1$_{413}$$^+$CD8$^+$ T cells are activated following stimulation with either IAV-, IBV- and ICV-targets, introducing a new paradigm that CD8$^+$ T cells can confer universal cross-reactivity across IAV, IBV and ICV, and hence have a much broader cross-reactivity potential than previously thought.

Figure 1F:
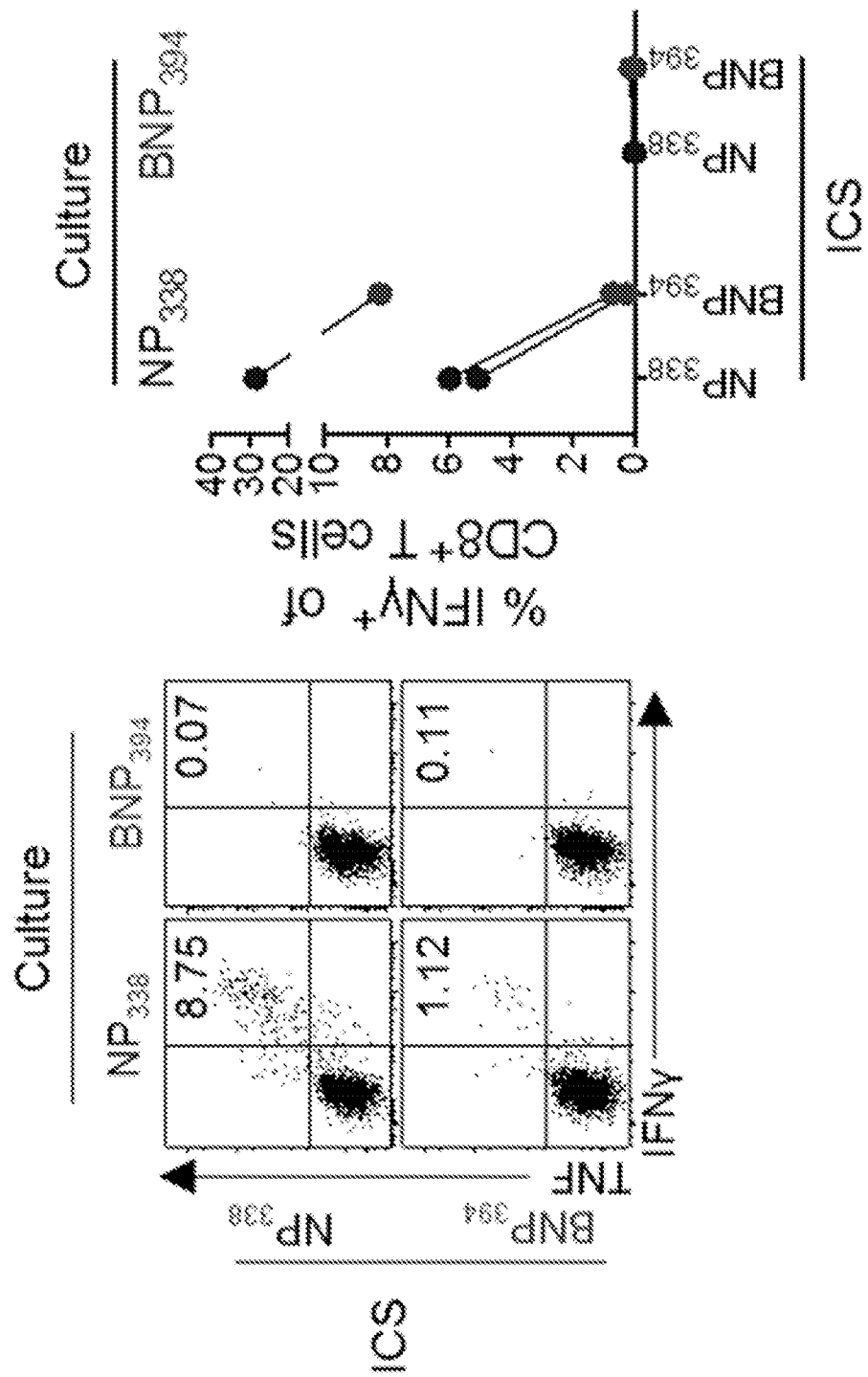
Figure 1G:
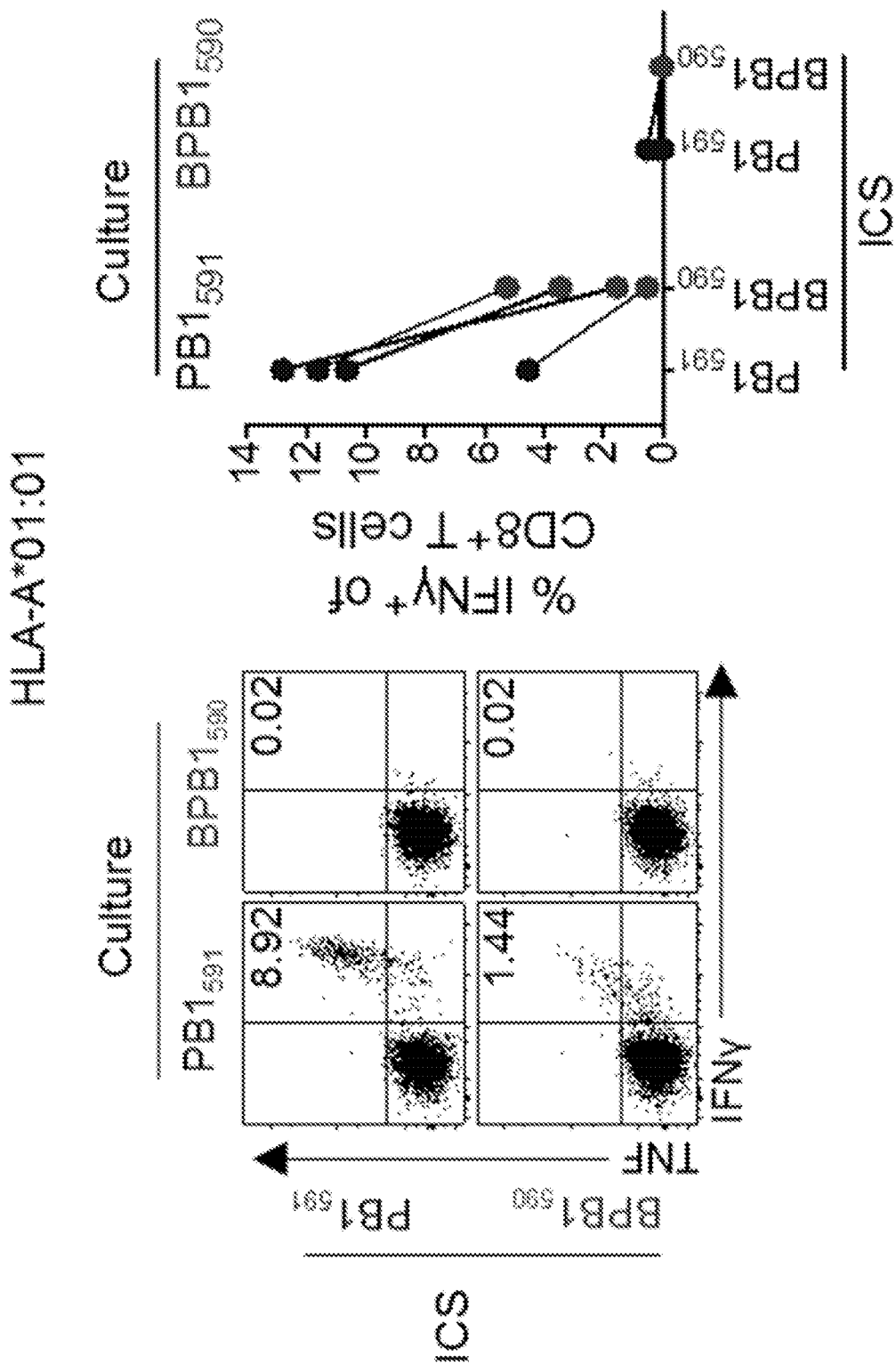

Analysis of the remaining two conserved and immunogenic peptides (PB1$_{591-599}$ and NP$_{338-345}$ in IAV, BPB1$_{590-598}$ and BNP$_{394-401}$ in IBV) revealed variations at one or two amino acids (S2A and L8I for PB1$_{591}$ and F1Y within NP$_{338}$) between IAV and IBV viruses, and a lack of conservation in ICV (FIG. 1b). In vitro expansion with either IAV- or IBV-derived peptides showed unidirectional cross-reactivity, with IAV-expanded CD8$^+$ T cells recognizing both IAV- and IBV-derived peptides, although the latter to a lesser extent. However, the IBV variants could not expand CD8$^+$ T cells directed at the cognate peptides, suggesting that the mutations may render these variants less immunogenic (FIG. 1f-g).

Collectively, these data demonstrate that human CD8$^+$ T cells can confer heterotypic cross-reactivity across IAV and IBV and ICV types. As the above findings are only based on the currently known IAV-derived epitopes and thus mainly limited to IAV peptides presented by well-characterized HLA class-I molecules, such universal cross-reactivity might be broader than defined here. Furthermore, the data suggest a need for identification of novel CD8$^+$ T cell epitopes recognizing both IAV- and IBV-derived peptides restricted by a broad range of HLAs represented across different ethnicities.

Example 2: Identification of IAV- and IBV-Derived Epitopes by Immunopeptidomics Methods: Immunopeptidome Analysis.

To identify peptides naturally presented by HLA-A*02:01 and HLA-A*A24:02 on the surface of infected cells, an immunopeptidomics approach was employed.

Class-I reduced (C1R) lymphoblastoid cell lines expressing HLA*A2:01 or HLA-A*24:02 were used. $10^9$ cells were infected with influenza A (X31) or influenza B (B/Malaysia) at a multiplicity of infection (moi) of 4 and cells were incubated for 12 hours. At 12 hours, cells were harvested and snap-frozen in $LN_2$.

Cell pellets of 5-15×$10^8$ cells were lysed using a combination of mechanical and detergent based lysis, the lysates cleared by ultracentrifugation, and MHC complexes isolated by immunoaffinity purification using solid-phase bound monoclonal antibodies for immunoaffinity purification as described previously (Dudek et al. 2012).

Anti-MHC-I antibodies BB7.2 (anti-HLA-A2) and w632 (anti-pan class I) were employed sequentially for purification of the transfected HLA-A*02:01 and remaining endogenous MHC class I (marginal HLA-B*35:03, HLA-C*04:01) of the CIR cells.

Anti-MHC-II antibodies LB3.1 (anti-HLA-DR), SPV-L3 (anti-HLA-DQ), and B721 (anti-HLA-DP) were subsequently used to isolate MHC class II complexes. Peptides were eluted from the MHC with 10% acetic acid, fractionated on a 4.6 mm internal diameter (i.d.)×100 mm monolithic reversed-phase C18 high-performance liquid chromatography (HPLC) column (Chromolith SpeedROD; Merck Millipore) using an ÄKTAmicro HPLC (GE Healthcare) system, vacuum concentrated, and reconstituted in 0.1% formic acid as described previously (Pymm et al. 2017).

Reconstituted fractions were analysed by Liquid chromatography-tandem mass spectrometry (LC-MS/MS) using a data dependent acquisition strategy either using a Dionex UltiMate 3000 RSLCnano system (Thermo Fisher Scientific) coupled to a Q-Exactive Plus Hybrid Quadrupole Orbitrap (Thermo Fisher Scientific), or a NanoUltra cHiPLC system (Eksigent) coupled to an AB SCIEX 5600+ TripleTOF mass spectrometer as described previously (Pymm et al. 2017).

Spectra were searched against a proteome database consisting of the human proteome (UniProt/Swiss-Prot v2016_04), the B/Malaysia proteome, and a 6 reading frame translation of the B/Malaysia genome, using ProteinPilot software (version 5.0, SCIEX).

Results/Discussion:

The EBV-transformed lymphoblastoid C1R cell line expressing high levels of the HLA-A*02:01 molecule (C1R-A2 cells). Cells were infected at a multiplicity of infection (moi) of 4 for 12 hours with B/Malaysia (FIG. 2*a*), as these conditions were found to be optimal in terms of infection (NP staining), viability and expression levels of surface HLA-A*02:01.

Liquid chromatography-tandem mass spectrometry (LC-MS/MS) analysis of peptides isolated from HLA-A*02:01 molecules revealed predominantly 9-mer (n=1490), followed by 11-mer (n=695) and 10-mer (n=589), peptides after filtering for peptides detected in isolates from parental HLA molecules (FIG. 2*a-b*). These peptides mainly exhibited the canonical anchor residues of HLA-A*02:01 ligands (Leucine (L) ar P2 and L or Valine (V) at last residue, favoring leucine at position 2 and a valine or leucine at the C-terminus (FIG. 2*b*). Length distributions were similar for human peptides from uninfected cells and human and viral peptides from infected cells.

Analyses from two independent experiments yielded a total of 73 potential HLA-A*02:01-presented IBV-derived peptides. The IBV-derived peptides mainly originated from hemagglutinin (BHA) (22.3%), followed by BNP (16.4%) and BM1 (11.9%), with all IBV proteins contributing to the HLA-A*02:01 immunopeptidome, except from BM2 and NB (FIG. 2*d*). In contrast, numerous peptides derived from BM2 were identified at high confidence in the analysis of peptides presented by the HLA class II.

Example 3: Screening of Novel Influenza B CD8+ T Cell Epitopes in Transgenic HHD-A2 Mice To determine the in vivo immunogenicity of the novel IBV-derived peptides identified in Example 2, HLA-A2-expressing transgenic (HHD-A2) mice were used . . . . These mice are not confounded by exposure infection history nor co-expression of other MHC-I molecules and thus provide an important tool for screening peptide antigens in vivo.

Methods and Results

Synthetic peptides were purchased from GenScript and dissolved in Hanks Balanced Salt Solution (HBSS) with DMSO. Mice were infected intranasally with 30 μl of influenza viruses diluted in sterile PBS (200 pfu of A/X31 for A24 mice, 100 pfu of B/Malaysia for A2 mice).

On day (d) 10 after intranasal infection (i.n.) with B/Malaysia (FIG. 2*e*), splenocytes were stimulated with each peptide individually and measured production of IFNγ and TNF.

Cells were stained with anti-CD8, anti-IFNγ and anti-TNF antibodies using the BD cytofix/cytoperm kit according to the manufacturer's instructions (BD Biosciences).

Of the 66 peptides tested, CD8+ T cell responses were targeted to 2 peptides ($HA_{543-551}$ and $NS1_{266-274}$). Responses could also be detected for a longer version of each of these peptides, namely $HA_{538-551}$ and $NS1_{264-274}$. These responses could also be detected in mice that had been primed with B/Malaysia and then 6-8 weeks later challenged with B/Phuket.

Figure 2A:
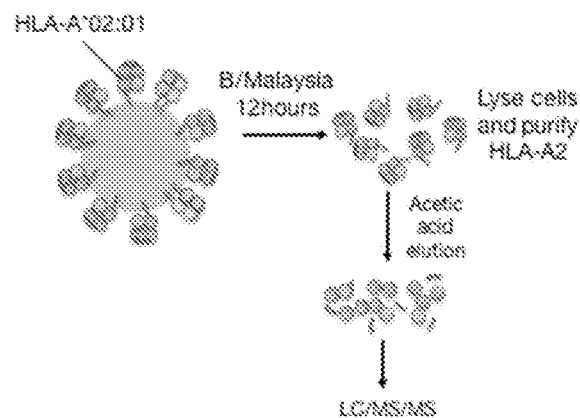
FIG. 2 Identification of novel influenza B CD8+ T cell epitopes by immunopeptidomics. a) Identification of naturally presented peptides by immunopeptidomics. (b) Peptide binding motifs for host and IBV HLA-A*02:01 ligands generated from combined non-redundant lists of 9mer, 10mer and 11 mer, using Icelogo by the static reference method against the swiss-prot human proteome. (c) Length distribution of filtered HLA-A*02:01 ligands (non-redundant by sequence) from uninfected (single experiment) and B/Malaysia infected (2 experiments) CIR.A*02:01 cells. Numbers of peptides of each length identified from the Human proteome (5% FDR cut-off) and B/Malaysia proteome (all confidences) are shown. d) Distribution of novel IBV-derived HLA ligand peptide according to protein antigen. Pooled data from 2 independent experiments e) In vivo screening of novel peptides in HHD (A2+) transgenic mice. Experimental design and representative FACS plots for immunogenic peptides. (f-h) In vitro screening of novel peptides in human HLA-A*02:01-expressing PBMCs. (f) Experimental outline of screening. (g) Representative concatenated FACS plots for each peptide pool are shown, with a mock (unstimulated) control outlined for comparison. Frequency of IFNγ$^+$ TNF$^+$CD8$^+$ T cells for each pool. Dots indicate individual donors, median and IQR are shown (n=11). (h) Frequency of IFNγ$^+$ TNF$^+$CD8$^+$ T cells directed towards individual peptides from pool 2 (n=6), median and IQR are shown. (i-j) In vitro validation of immunogenic peptides. (i) Experimental outline of validation. (j) Representative FACS plots for a positive CD8$^+$ T cell response directed towards each peptide. Frequency of IFNγ$^+$ TNF$^+$ CD8$^+$ T cells. Donors are color-coded, medians and IQRs are shown. (n=6). (k-n) Immunization with novel IBV peptides accelerates viral clearance. (k) Brief experimental outline. (l) Number of total (A2/BHA$_{543}$ and A2/BNS1$_{266}$) tetramer$^+$ CD8 T cells in the spleen on day 6 after IBV infection. (m) Viral titers in the lungs and nose of peptide-vaccinated and mock-vaccinated mice, following IBV infection. Days 5 (n=5) and d6 (n=5) were assessed independent experiment to d7 (n=4-5). (n) Cytokine responses in the BAL on d7 after IBV challenge (n=4-5). (n-o) Statistical significance was determined using an unpaired t-test. *p<0.05, p<0.005. **p<0.0001. Means and SEM are shown (n=5). (g, i, j & l) 'No peptide' control was subtracted.
Figure 2B:
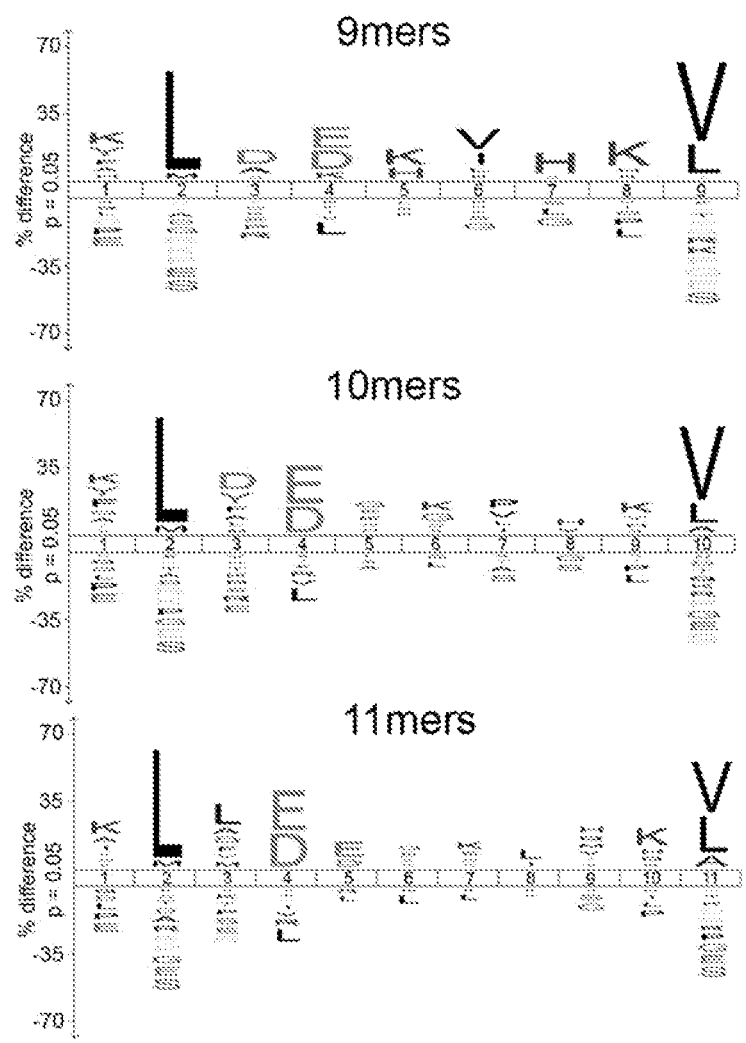
Figure 2C:
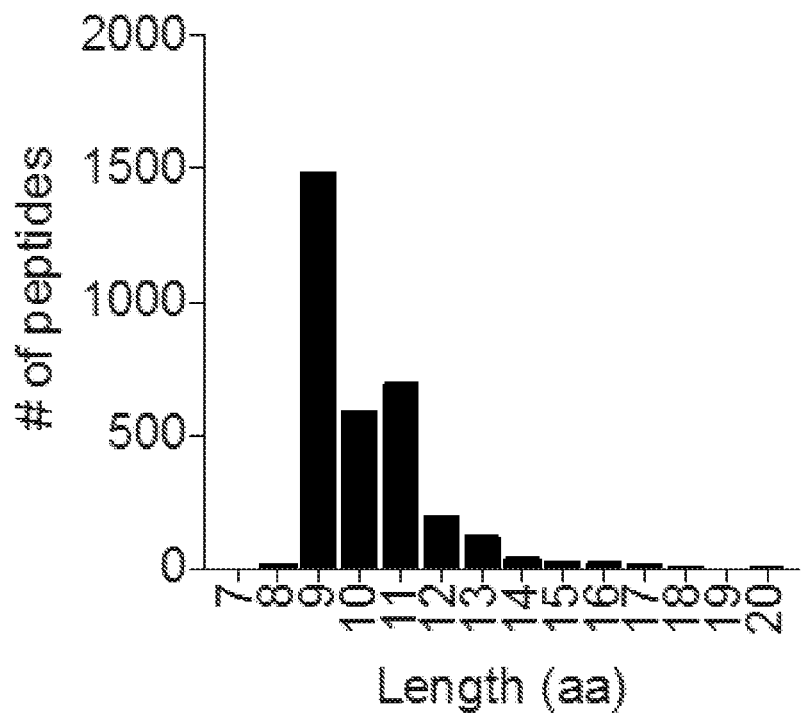
Figure 2D:
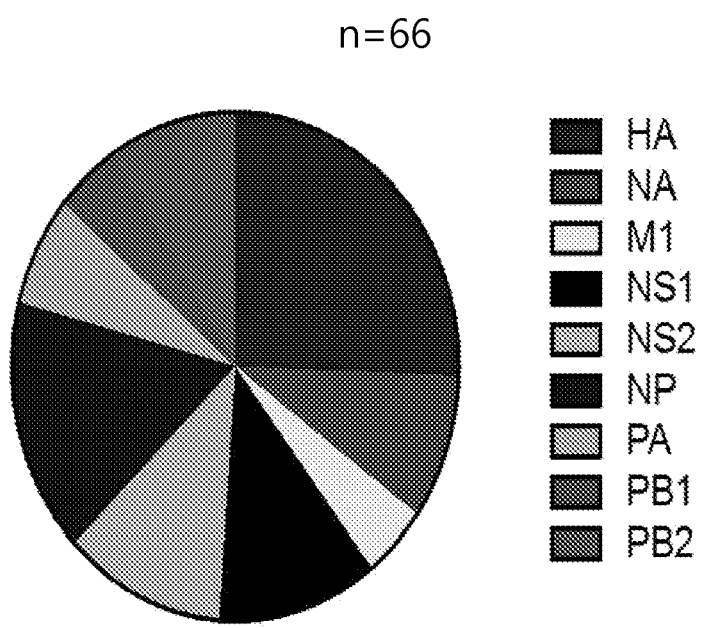
Figure 2E:
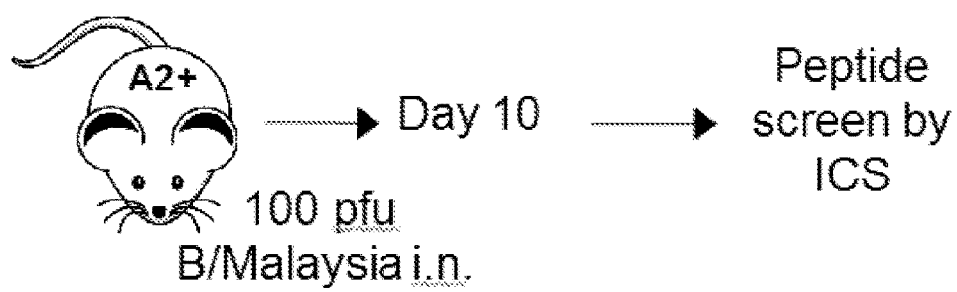
Figure 2E:
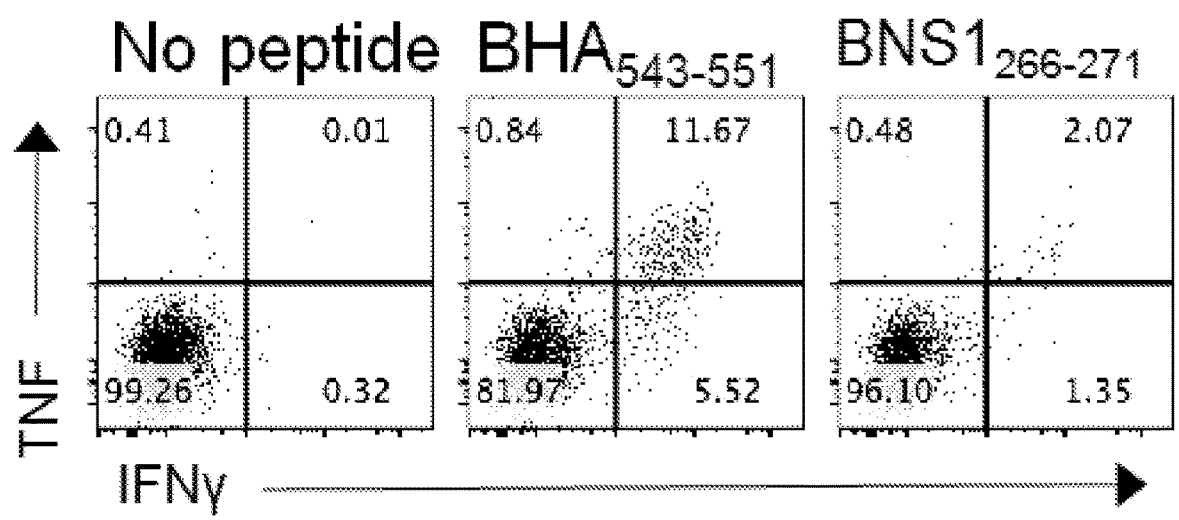

Immunodominant CD8+ T cell responses were largely targeted towards $A2/BHA_{543-551}$ (mean of 5% of CD8+ T cells) and $A2/BNS1_{266-274}$ (mean of 1.8% of CD8+ T cells), with smaller subdominant responses observed for $A2/HA_{538-551}$ and $A2/BNS1_{264-274}$ (mean of <0.5% of CD8+ T cells), which overlap with $A2/BHA_{543-551}$ and $A2/BNS1_{266-274}$, respectively (FIG. 2e).

The peptides were randomly assigned in 6 pools of 10-12 peptides, avoiding overlapping peptides in the same pool and CD8+ T cell responses to each pool at the site of infection was assessed, as represented by the bronchoalveolar lavage (BAL). CD8+ T cell responses were targeted to pools 2 and 3 containing the $BHA_{543-551}$, $BNS1_{266-274}$ and $BNS1_{264-274}$ peptides, as confirmed separately.

To further verify the immunogenicity of these epitopes in recall responses, HHD-A2 mice were primed i.n. with B/Malaysia, infected with the heterologous strain B/Phuket 6 weeks later and then assessed CD8+ T cells against the main epitopes $A2/BHA_{543-551}$ and $A2/BNS1_{266-274}$ in the spleen on d8 after challenge. The number of secondary IFNγ+TNF+ CD8+ T cells in the spleen was ~27-fold higher than following a primary infection, although this did not reach statistical significance. Additionally, CD8+ T cells for both specificities showed increased polyfunctionality (IFNγ+ TNF+IL-2+) following secondary infection (0.14% and 2.14% of CD8+ T cells for $BHA_{543}$, n=4-5, p=0.013) Thus, the in vivo screening in HHD-A2 mice identified 4 immunogenic peptides, with immunodominant CD8+ T cells being heavily biased towards $A2/BHA_{543-551}$ and $A2/BNS1_{266-274}$ epitopes in both primary and secondary infections.

Figure 2F:
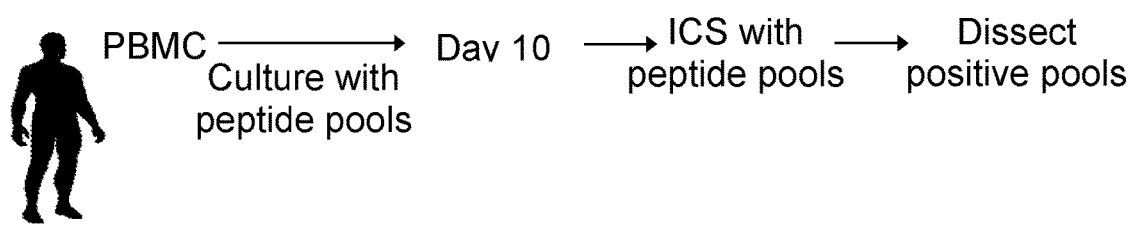
Figure 2G:
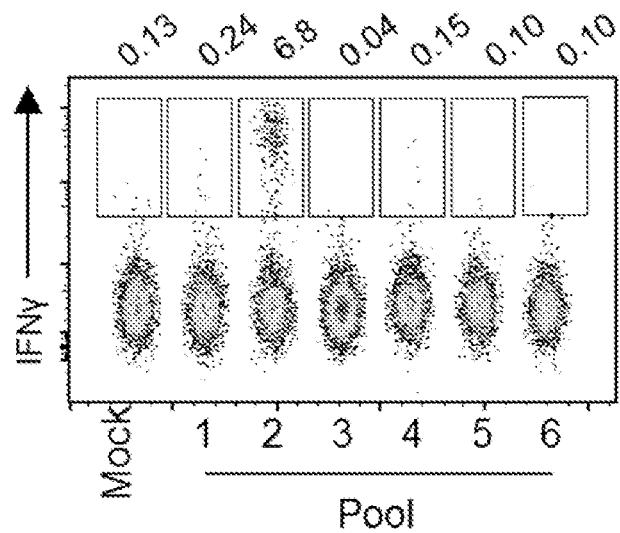
Figure 2G:
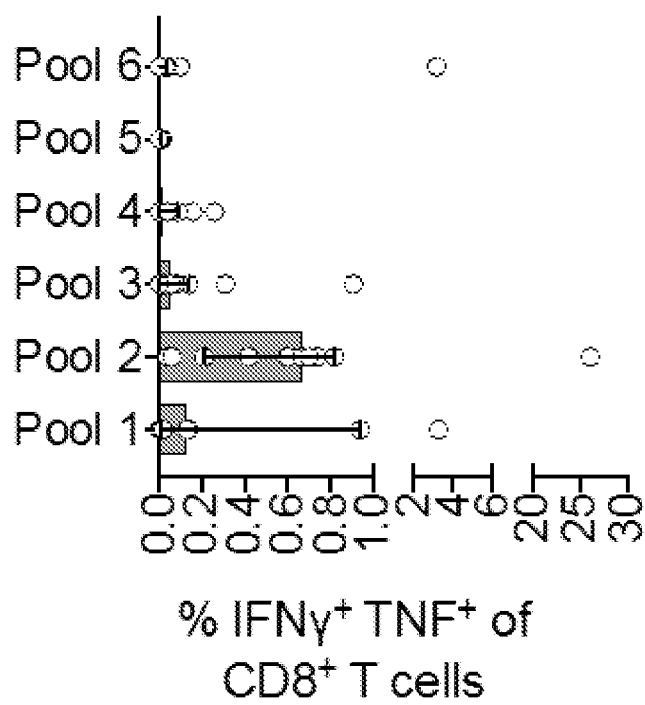
Figure 2H:
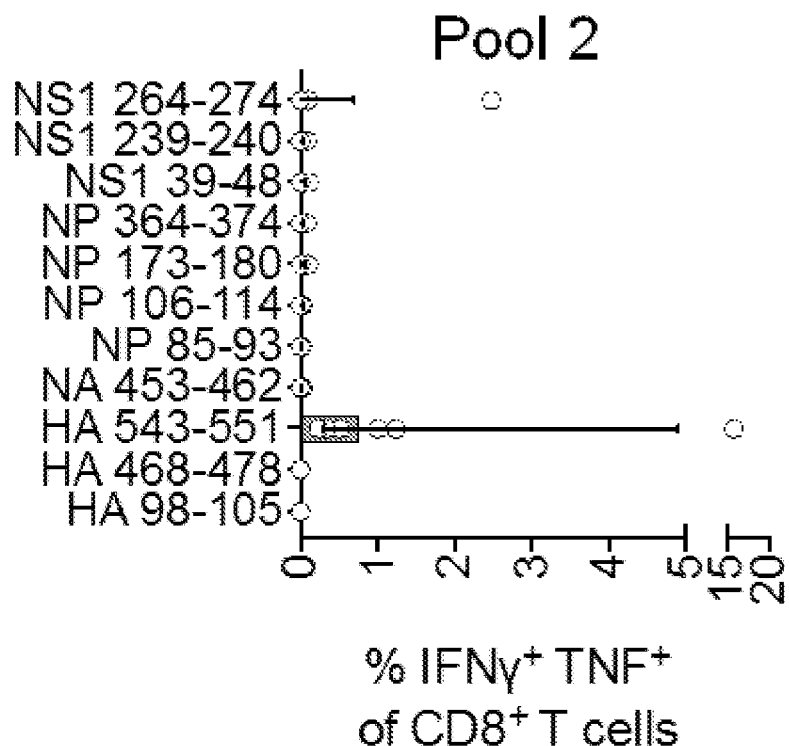

As a next step, the IBV-specific CD8+ T cell responses towards the 67 LC/MS-identified IBV-peptides in HLA-A*02:01-expressing individuals were dissected. CD8+ T cell lines specific for each of the 6 peptide pools were established, and then re-stimulated cells with the cognate pool in an IFNγ/TNF ICS assay (FIG. 2f). CD8+ T cell responses were predominantly targeted towards pool 2 (80% of donors responding, n=11), with smaller responses detected in some donors for pools 1, 3, 4 and 6 (FIG. 2g). Dissection of pool 2 into individual peptides verified $A2/BHA_{543-551}$ as the immunodominant epitope amongst HLA-A*0201+ donors (n=6) (FIG. 2h). Subdominant responses towards $A2/BHA_{538-551}$, $A2/NS1_{266-274}$, $A2/BNS1_{264-274}$ and $BM1_{132-140}$ were also detected in some donors.

Figure 2I:
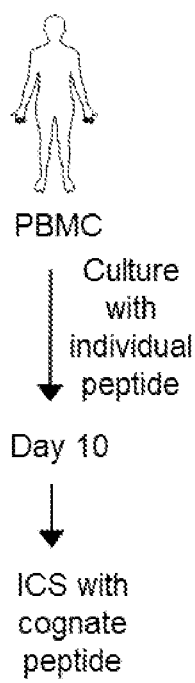
Figure 2J:
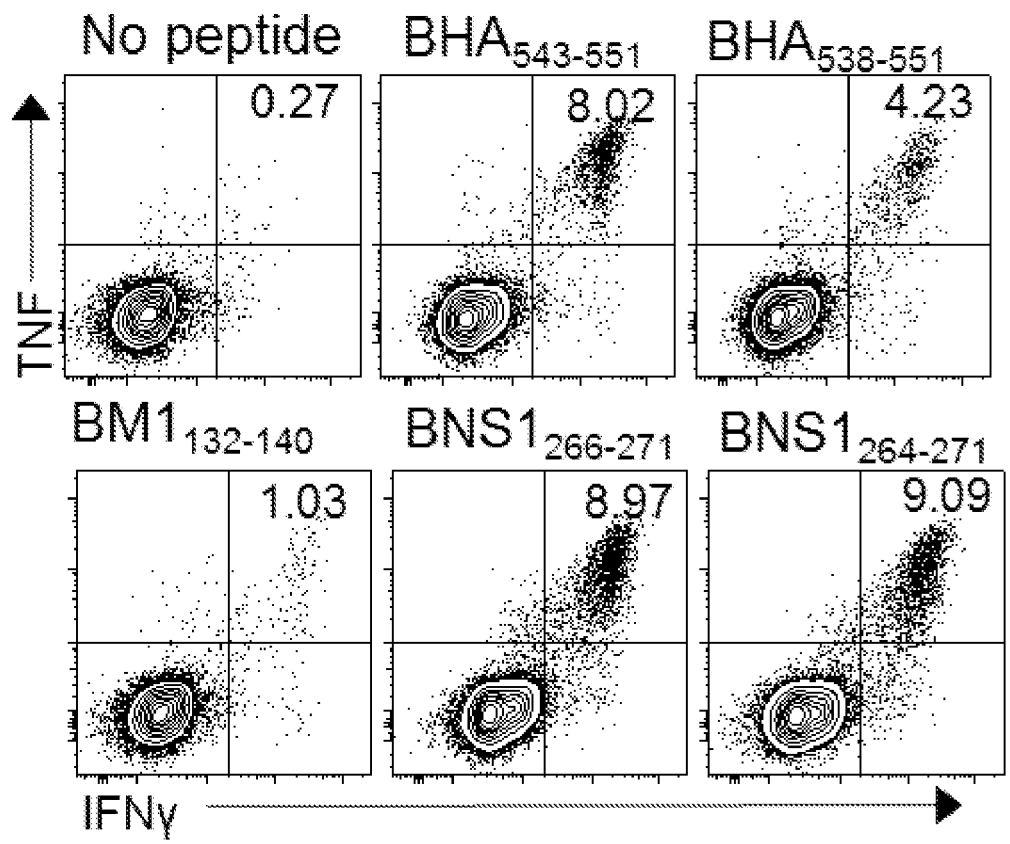
Figure 2J:
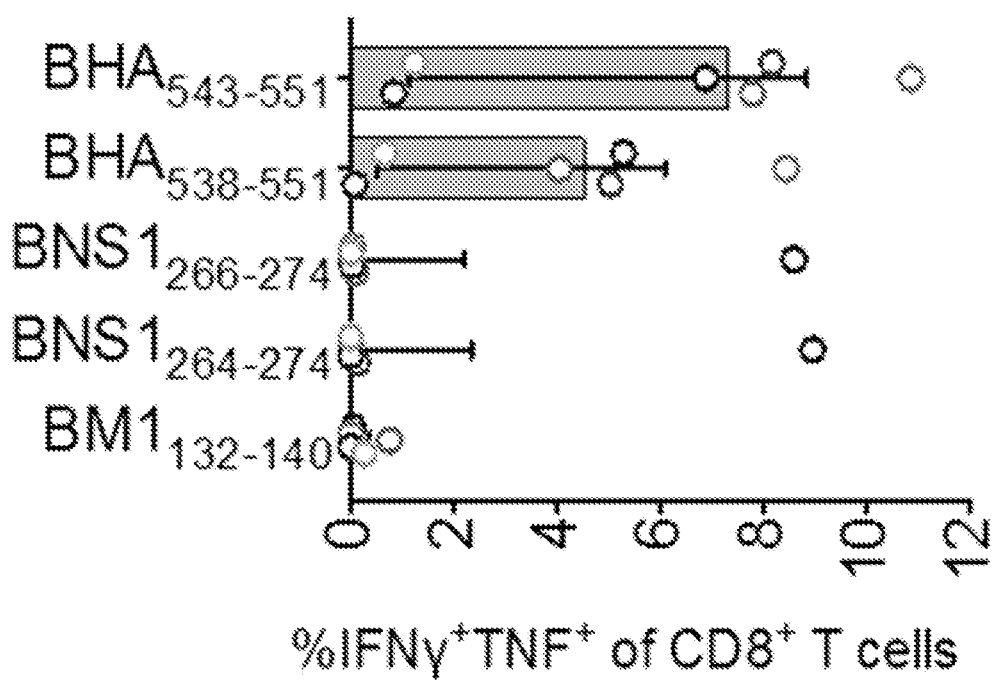

To validate these responses independently of the peptide pools, CD8+ T cell lines were established towards individual immunogenic peptides (FIG. 2i). Similar to HHD-A2 mice, CD8+ T cell responses to $A2/BHA_{543-551}$ were of the greatest magnitude (median 7.35% of CD8+ T cells; n=6) and more frequent amongst donors (6/6) than the subdominant $A2/NS1_{266-274}$, $A2/BNS1_{264-274}$ and $A2/BM1_{132-140}$ (0.035% and 0.025% of CD8+ T cells, respectively), each found in a single donor (FIG. 2j). Thus, these thorough in vivo and in vitro analyses identified 5 novel peptides recognized by CD8+ T cells in complex with the HLA-A*02:01 molecule, with $BHA_{543-551}$ being immunodominant amongst the peptides tested, in both mice and humans.

Having identified novel IBV CD8+ T cell epitopes, the conservation of two most immunodominant peptides, $BHA_{543-551}$ and $BNS1_{266-274}$, across IBV strains was determined. Both peptides were highly conserved (mean conservation of 99% and 98%, respectively) in >14,000 sequences per segment, spanning both lineages and 77 years of evolution (1940-2017). While some of the peptides identified by immunopeptidomics were highly conserved (>70%) in IAV (n=6 peptides) or in ICV (n=1) these were not immunogenic in humans or mice.

Overall, the immunopeptidomics approach identified 73 previously uncharacterized IBV-derived HLA-A*02:01 peptide-ligands, 67 of which were tested for immunogenicity, with CD8+ T cell responses being targeted predominantly to $BHA_{543-551}$, highly conserved across IBV, but not IAV or ICV.

Figure 2K:
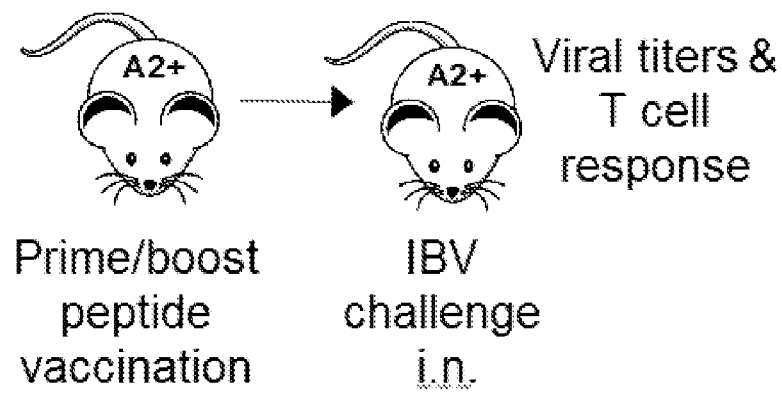
Figure 2L:
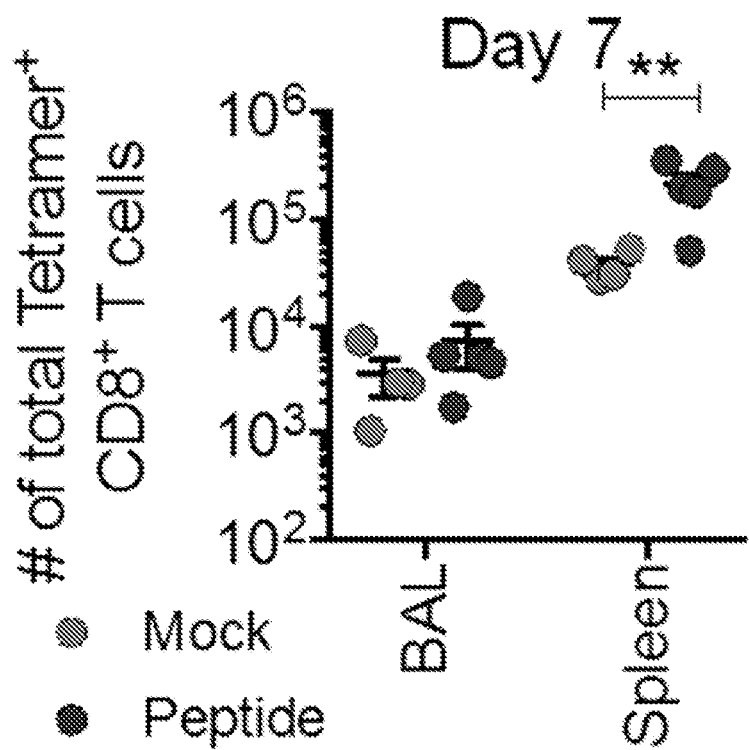
Figure 2M:
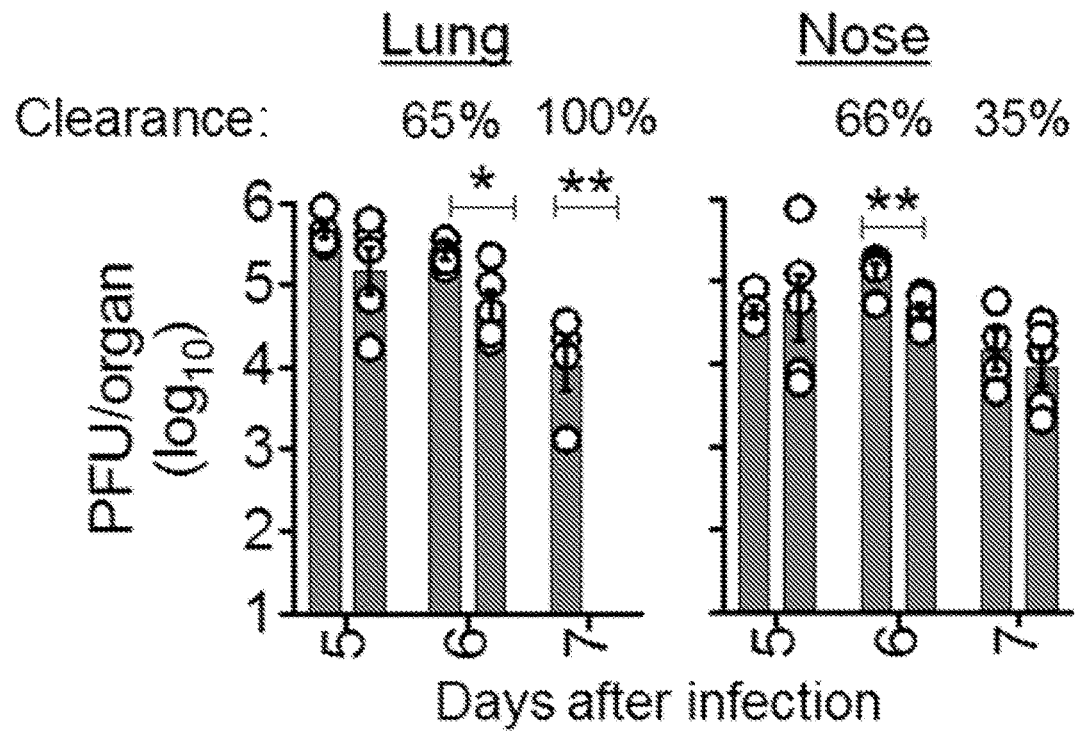
Figure 2N:
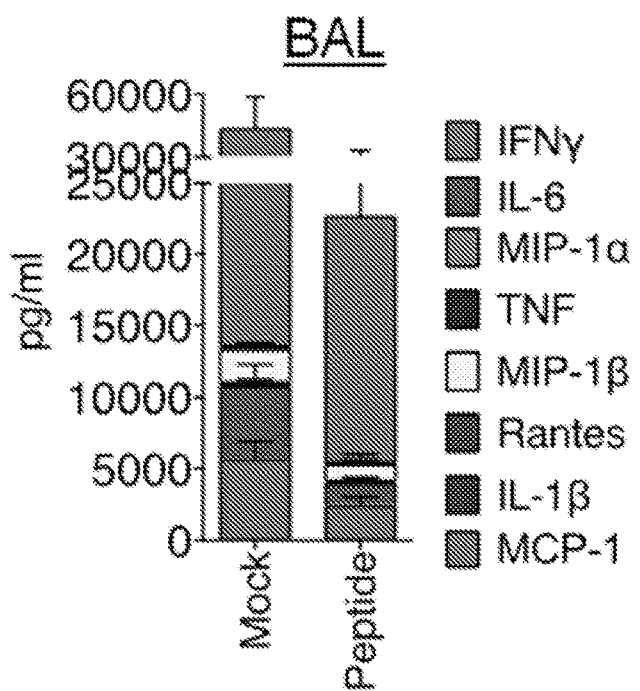

Example 4: Protective Capacity of $A2/BHA_{543}$- and $A2/BNS1_{266}$-Specific CD8+ T Cells During In Vivo IBV Infection To determine the protective capacity of the novel IBV CD8+ T cell epitopes, we vaccinated mice with the $BHA_{543}$ and $BNS1_{266}$ peptides using a prime/boost approach (FIG. 2k). Vaccination with peptides resulted in significantly higher numbers of $A2/BHA_{543}$- and $A2/BNS1_{266}$-tetramer+ CD8+ T cells in the spleen on d6 and d7 after IBV infection when compared to mock-vaccinated (adjuvant alone) mice (~5.6-fold p<0.05) (FIG. 2l). $A2/BHA_{543}^+CD8^+$ and $A2/BNS1_{266}^+CD8^+$ T cell numbers were comparable (p>0.05) in the BAL (with ~2-fold increase in immunized mice). Importantly, peptide-vaccinated mice exhibited a significant ~65% reduction in viral titers in the lung and nose on d6 and 100% clearance in the lung on d7 after IBV infection when compared to the mock-immunized group (p<0.05) (FIG. 2m). Additionally, there was a significant decrease (p<0.05) in the levels of inflammatory cytokines (MIP-1β, IL-6, IL-1β, IFNγ) in d7 BAL of peptide-vaccinated mice in comparison to the mock-immunised animals. Thus, CD8+ T cells directed at our newly-identified IBV-specific epitopes are protective, as they can markedly accelerate viral clearance and reduce the cytokine storm at the site of infection. Although the $PB1_{413}$ peptide was included in the immunization regimen, CD8+ T cells specific for the $A2/PB1_{413}$ epitope could not be detected either in (i) this experiment, (ii) following primary, secondary or tertiary influenza infections or (iii) following lipopeptide vaccination due to a lack of naïve $A2/PB1_{413}$-specific precursors in HHD-A2 mice.

Figures 3A, 3B:
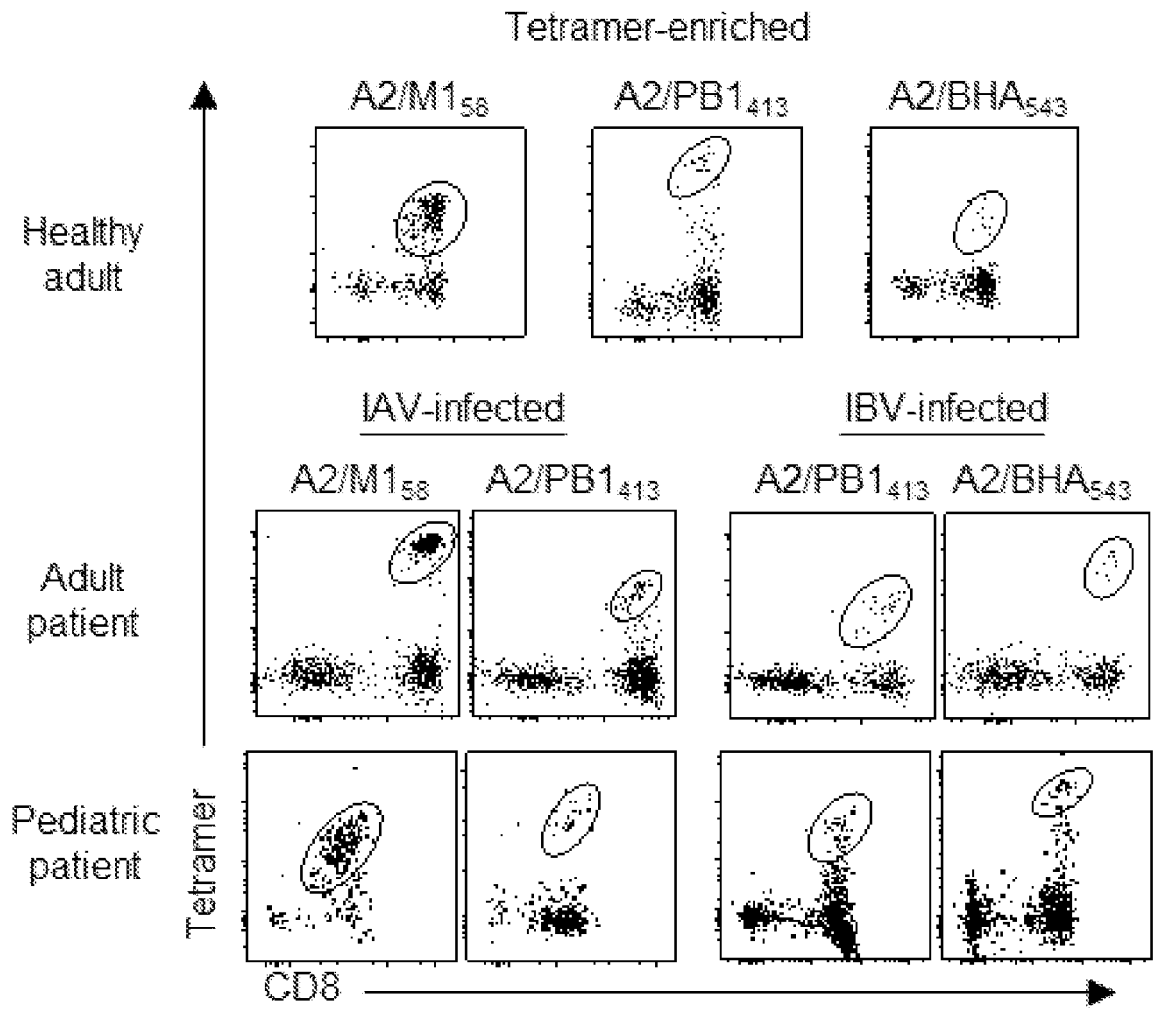
FIG. 3 Presence of memory and effector pools of universal CD8$^+$ T cells in healthy adults, influenza-infected individuals and human tissues. (a-d) Tetramer-specific CD8$^+$ T cells in healthy and influenza-infected individuals. (a) Ex-vivo TAME on PBMCs from healthy and infected donors. Representative FACS plots are shown. (b) Characteristics of healthy and influenza-infected cohorts used in this study. ILI: influenza-like illness. (c) Precursor frequency of tetramer$^+$ cells in healthy and influenza-infected individuals (n=6-24). Statistical significance was determined using the Mann-Whitney test, *p<0.05, **p<0.005. Median and IQR are shown. (d) Precursor frequency of tetramer$^+$ CD8$^+$ T cells in healthy and influenza-infected individuals across age. (e) Expression profiles of tetramer$^+$ CD8$^+$ T cells for activation/effector markers CD38 and Ki-67. Representative FACS plots are shown. Frequency of CD38$^+$/Ki-67$^+$ tetramer$^+$ CD8$^+$ T cells from healthy controls (n=3-5) and influenza-infected donors (n=6-26). Statistical significance for changes in the frequency of CD38$^-$Ki-67$^-$ cells was determined using the Mann-Whitney test A, *p<0.05, **p<0.005. (f-g) Ex-vivo detection of universal CD8$^+$ T cells in human lung samples. (f) Frequency of tetramer$^+$ CD8$^+$ T cells (n=3). (g) Phenotype of tetramer$^+$ CD8$^+$ T cells based on CD103 and CD69 expression. Representative FACS plots are shown. ND: not detected.
Figure 3C:
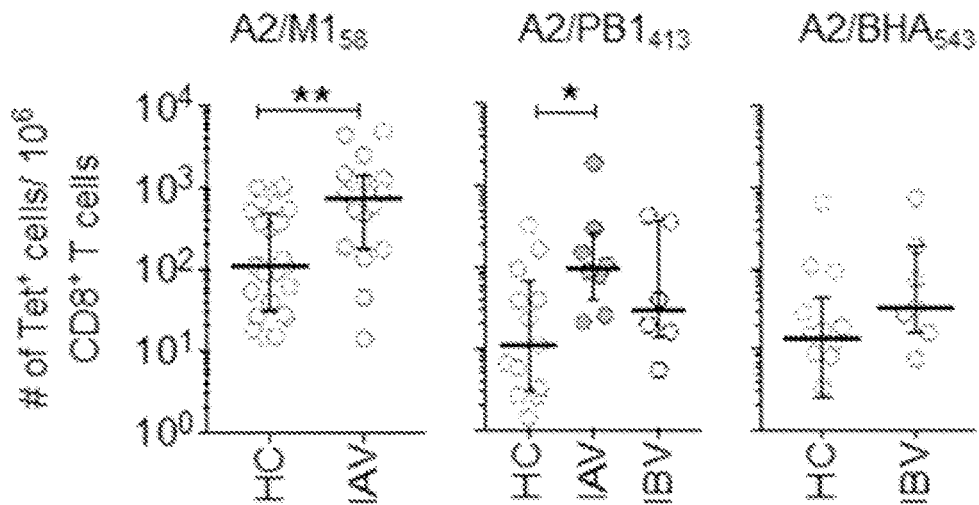
Figure 3D:
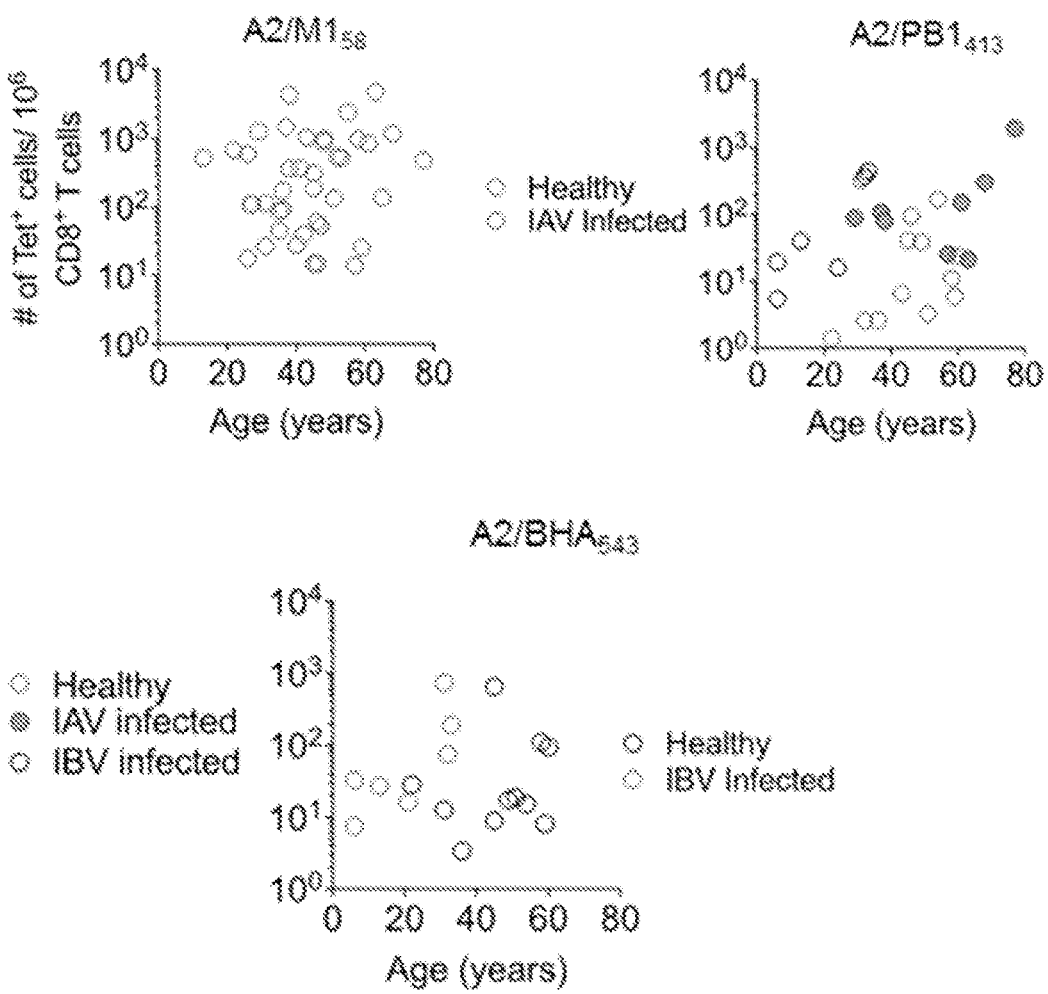
Figure 4A:
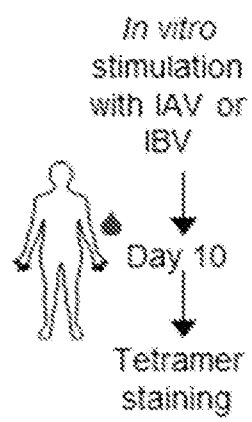
FIG. 4 Functional assessment of universal and type-specific CD8$^+$ T cells. (a-c) Immunodominance of universal CD8$^+$ T cells during in vitro IAV or IBV infection. (a) Experimental outline. (b) Responses during IAV infection against A2/M1$_{58}$, A2/PA$_{46}$ and A2/PB1$_{413}$ and (c) IBV infection against A2/BHA$_{543}$, A2/BNS1$_{288}$ and A2/PB1$_{413}$. Bar charts show the contribution of each specificity to the total measured (sum of tetramer$^+$) response. ND: not detected. (d-e) Structures of HLA-A*02:01 (white cartoon) presenting the (d) PB1$_{413-421}$ (black sticks) and (e) BHA$_{543-551}$ peptide (blue sticks). (f-g) Functional avidity of universal and type-specific CD8$^+$ T cells. (f) Peptide titration curve for each T cell specificity (n=6-9). (g) EC$_{50}$ of each T cell specificity (n=6-9). (h-i) Polyfunctionality assessment of universal and type-specific CD8$^+$ T cells. Pie charts show the mean proportion for each number of functions detected for each specificity (n=6-9). (i) Bar charts show the median (line) and minimum/maximum of number of functions for each specificity (n=6-9). (j-l) pMHC-I avidity of universal and type-specific CD8$^+$ T cells. PBMCs were stained with WT, D227K or Q115E pMHC-I tetramers. (j) Representative FACS plots are shown. (k) Frequency of CD8-independent staining (D227K/WT×100). (l) Frequency of additional low avidity staining ((Q115E-WT)/WT×100). Bars indicate the mean (n=7-10). (f-l) Experiments were performed on day-10 T cell lines specific for each peptide. Medians and IQRs are shown. Statistical significance was determined using the Mann-Whitney test, *p<0.05, **p<0.005.
Figure 4B:
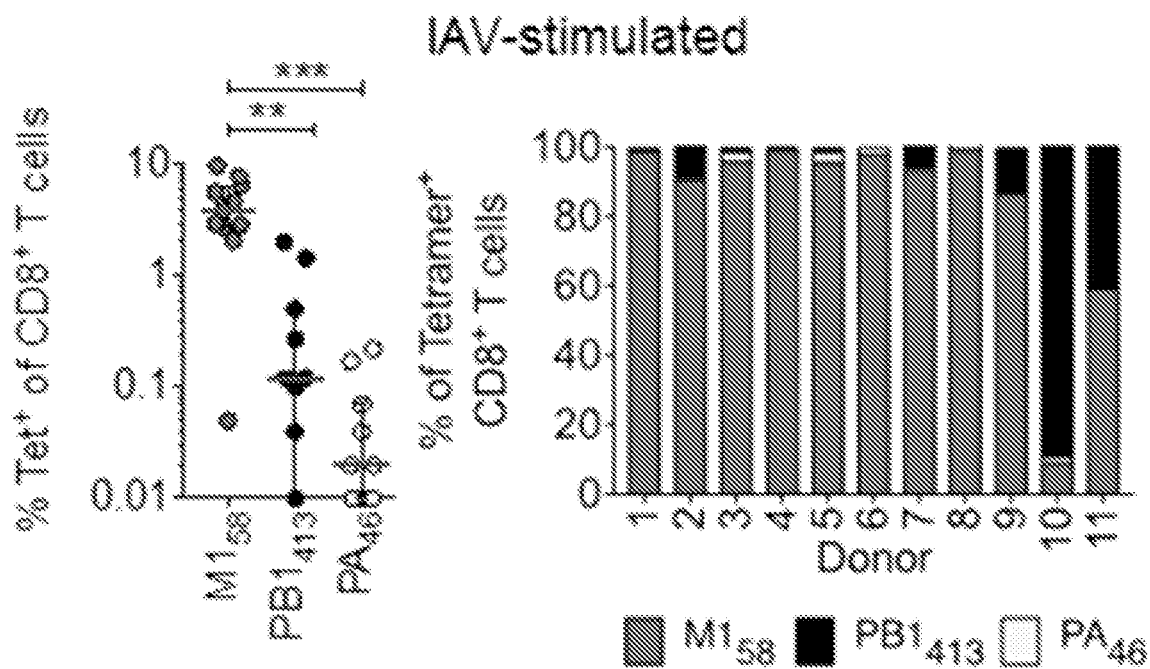

Example 5: Recruitment of Universal $A2/PB1_{413-421}^+CD8^+$ T Cells Following Human IAV and IBV Infection To evaluate the recruitment and activation of universal $A2/PB1_{413-421}^+CD8^+$ T cells in humans during influenza virus infection, PBMC samples from 3 different clinical cohorts of PCR-confirmed IAV- or IBV-infected individuals were analysed (FIG. 4b). Using a tetramer-associated magnetic enrichment (TAME) technique, antigen-specific CD8+ T cells were detected directly ex vivo (FIG. 3a). A healthy adult cohort was also analyzed for comparison (FIG. 3b). $A2/M1_{58}$- and $A2/PB1_{413}$-specific CD8+ T cells were detected in 100% and 50% of IAV+ individuals (n=16) respectively, while $A2/BHA_{543}$- and $A2/PB1_{413}$-specific CD8+ T cells were detected in 75% and 87.5% of IBV+ individuals (n=8). The frequency of $A2/M1_{58}$- and A2/PB1$_{413}$-specific CD8$^+$ T cells in the blood were significantly increased (4.3- and 6-fold increase, respectively) in IAV-infected patients, as compared to memory CD8$^+$ T cells in healthy donors (FIG. 3c). The numbers of A2/BHA$_{543}$- and A2/PB1$_{413}$-specific CD8$^+$ T cells in IBV-infected patients increased 2.2- and 2.6-fold, respectively, above the numbers in healthy donors, however these did not reach statistical significance, most likely due to the differential age distribution in IBV-infected (p=0.0002), but not IAV-infected (p=0.27) patients comparing to healthy controls. Notably, tetramer-positive CD8$^+$ T cells for all 3 specificities could be detected across all age groups (FIG. 3d).

Figure 3E:
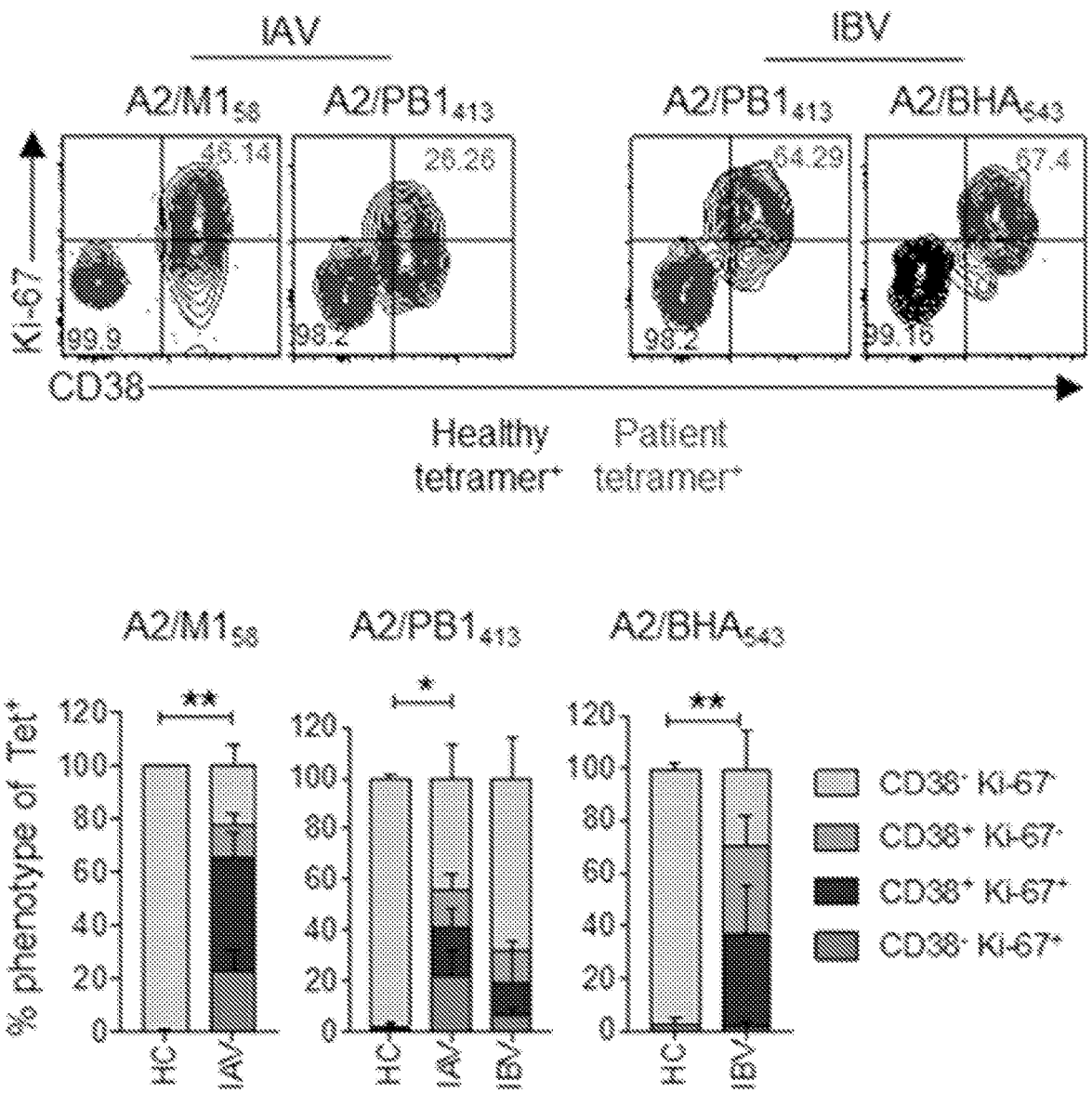

Tetramer-positive A2/PB1$_{413}$$^+$CD8$^+$, IBV-A2/BHA$_{543}$$^+$ and IAV-A2/M1$_{58}$$^+$CD8$^+$ T cells detected in IAV- or IBV-infected patients displayed an increase in CD38$^+$/Ki-67$^+$ expression (FIG. 3e), which represents an activated/effector phenotype during human viral infections, suggesting their recruitment during human influenza virus infection. The expression of additional activation markers, like HLA-DR and PD-1, was also increased on tetramer$^+$CD8$^+$ T cells, although variably across epitopes. The variability in numbers and phenotype between tetramer$^+$CD8$^+$ T cells is likely due to (i) the age range and exposure history of the donors, and (ii) varying times of sampling following influenza virus infection, both within and between the cohorts (FIG. 3b). Indeed, CD8$^+$ T cell responses after human A/H1N1 infection peak within 7 days and then contract rapidly. Additionally, the magnitude and activation status of CD8$^+$ T cells within the circulation can underrepresent virus-specific cells at the site of infection during human respiratory virus infections.

These data show that A2/PB1$_{413}$$^+$CD8$^+$ T cells are truly universal as they can be detected with an activated/effector phenotype in HLA-A*0201-expressing influenza-infected patients following either IAV or IBV infection. Additionally, activated/effector CD8$^+$ T cells specific for A2/BHA$_{543-551}$, identified by immunopeptidomics, can be detected during human IBV infection, illustrating the power of mass-spectrometry in identifying novel peptide ligands.

Figure 3F:
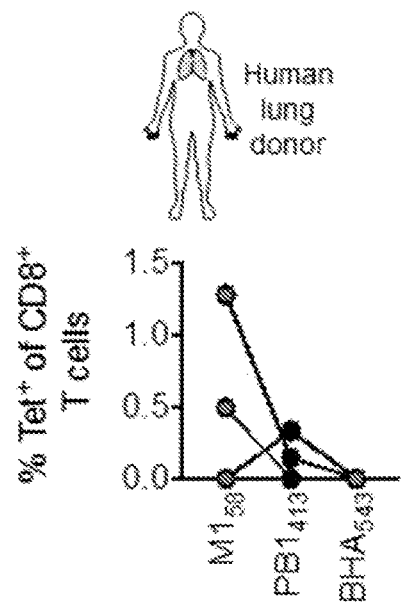
Figure 3G:
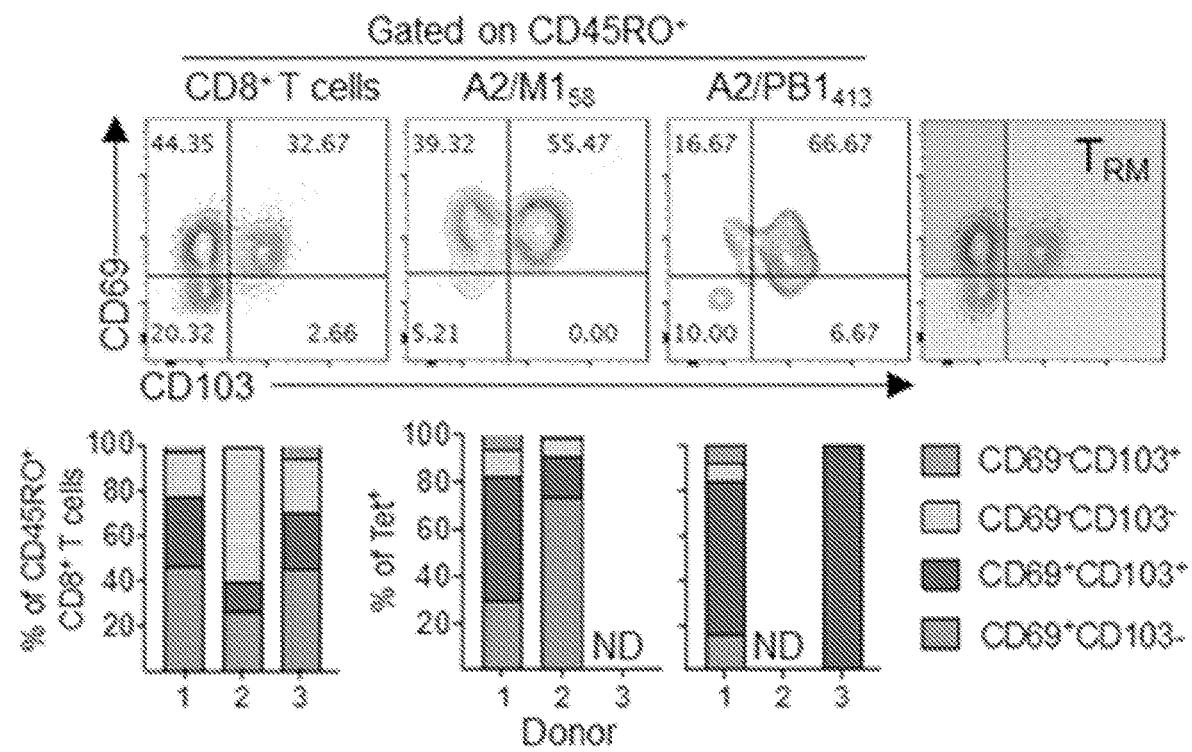

Example 6: Detection of Tissue-Resident Memory Universal A2/PB1$_{413}$$^+$ CD8$^+$ T Cells in Human Lungs As human memory CD8$^+$ T cells also reside outside the circulation, a rare set of human lung samples from deceased organ donors (n=3) were used to assess the presence of universal A2/PB1$_{413}$$^+$CD8$^+$ T cells at the site of infection. CD8$^+$ T cells specific for A2/M1$_{58}$ and A2/PB1$_{413}$, but not A2/BHA$_{543}$ were detected within human lung CD8$^+$ T cells (2/3 donors for either specificity, FIG. 3f). Importantly, the majority of A2/PB1$_{413}$$^+$CD8$^+$ T cells exhibited a tissue-resident memory CD69$^+$CD103$^+$CD45RO$^+$ phenotype (FIG. 3g). Although based on a limited number of donors, this analysis indicates the presence of universal A2/PB1$_{413}$$^+$ tissue-resident memory CD8$^+$ T cell pools in the human lung.

Overall, circulating pools of effector and memory IAV-A2/M1$_{58}$$^+$, IBV-A2/BHA$_{543}$$^+$ and universal A2/PB1$_{413}$$^+$ CD8$^+$ T cells can be detected directly ex vivo in peripheral blood of healthy individuals as well tissue-resident IAV-A2/M1$_{58}$-specific and universal A2/PB1$_{413}$-specific CD8$^+$ T cells memory pools in the human lung.

Figures 4C, 4D, 4E:
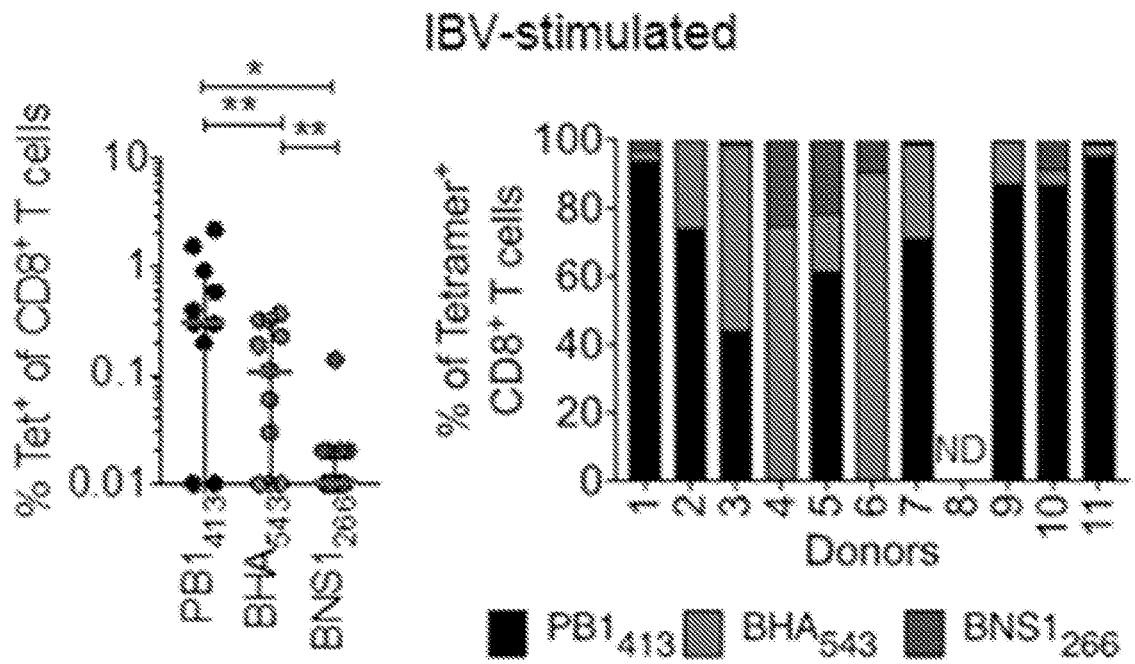
Figure 4F:
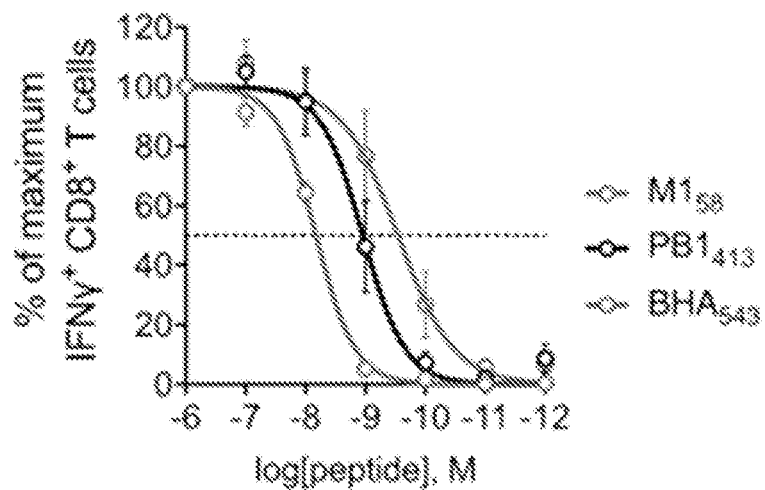
Figure 4G:
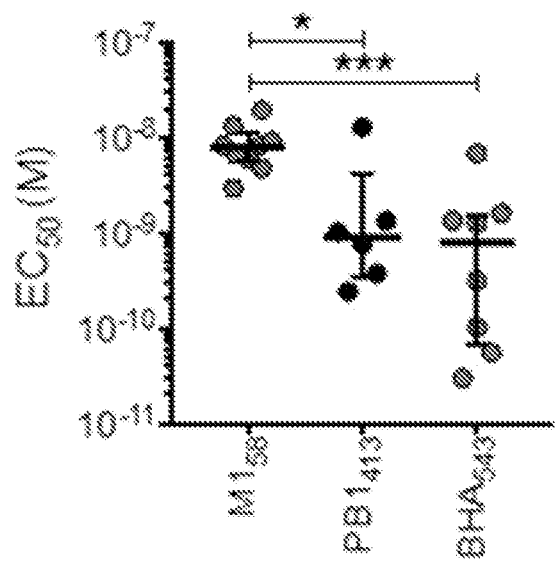

Example 7: Immunodominance of Universal A2/PB1$_{413}$$^+$ Over IBV-Specific A2/BHA$_{543}$$^+$CD8$^+$ T Cells in IBV Infection These data so far identified three conserved HLA-A*02:01-restricted epitopes for IBV: the universal A2/PB1$_{413}$ and two IBV-specific (A2/BHA$_{543-551}$ and A2/NS1$_{266-274}$ hereafter A2/BHA$_{543}$ and A2/BNS1$_{266}$) epitopes. To further understand the role of the universal A2/PB1$_{413}$$^+$CD8$^+$ T cells in the immunodominance hierarchy following either IAV or IBV infection, IAV- or IBV-specific CD8$^+$ T cell lines were established in vitro from PBMC of healthy adults (n=11) and assessed tetramer-specific CD8$^+$ T cell responses against IAV epitopes (A2/M1$_{58-66}$ (A2/M1$_{58}$), A2/PA$_{46-54}$ (A2/PA$_{64}$), A2/PB1$_{413}$) and IBV epitopes (A2/BHA$_{543}$, A2/BNS1$_{266}$, A2/PB1$_{413}$). Consistent with the IFNγ staining (FIG. 1e), A2/PB1$_{413}$-tetramer detected universal A2/PB1$_{413}$$^+$CD8$^+$ T cells within both IAV- or IBV-specific CD8$^+$ T cell lines, although they displayed differential immunodominance hierarchies following either IAV and IBV infection (FIG. 4a-c). Within the IAV-specific CD8$^+$ T cell lines, the A2/M1$_{58}$-tetramer$^+$CD8$^+$ T cell population was significantly dominant (median of 3.9% tetramer$^+$ of CD8$^+$ T cells; detected in all 11 donors) over the universal A2/PB1$_{413}$$^+$ (0.12%; detected in 10/11 donors) and the subdominant A2/PA$_{46}$$^+$CD8$^+$ T cells (0.05%) populations (FIG. 4b). Conversely, the universal A2/PB1$_{413}$ epitope within the IBV-specific T cell lines was immunodominant (0.3%; detected in 8/11 donors) over the IBV-specific A2/BHA$_{543}$ (0.11%; detected in 10/11 donors) and A2/BNS1$_{266}$ epitopes (0.01%) (FIG. 4c). These data demonstrate that (i) the universal A2/PB1$_{413}$ as well as the newly identified IBV-specific A2/BHA$_{543}$ and A2/BNS1$_{266}$ CD8$^+$ T cells can be expanded following virus stimulation in vitro, and (ii) immunodominance of the universal A2/PB1$_{413}$ epitope depends on the type of influenza infection.

Example 8: Different Conformations of the Universal PB1$_{413-421}$ and IBV-Specific BHA$_{543-551}$ Peptides Bound to HLA-A*02:01 Molecule To understand differential hierarchies observed for the A2-restricted influenza epitopes (PB1, BHA and M1), the ability of the epitopes to stabilize the HLA-A2 molecule was investigated including the structures of HLA-A2 presenting the PB1 and BHA peptides and compare them with previously solved HLA-A2-M1 structure. The pHLA-A*02:01 molecule in complex with M1$_{58}$ exhibited a Tm (temperature required to unfold 50% of the protein) of 65° C.[34], while both BHA$_{543}$ and PB1$_{413}$ were more stable, both exhibiting a Tm of ~72° C. Therefore, the observed hierarchy (M1>PB1>BHA) cannot be linked to the pHLA complex stability.

Subsequently, the HLA-A*02:01 structures in complex with the PB1$_{413}$ and BHA$_{543}$ peptides were determined at a resolution of 2.3 and 1.8 Å, respectively. The PB1$_{413}$ and the BHA$_{543}$ peptides adopted a canonical extended conformation with P2-Met/Leu and P9-Val/Leu acting as anchor residues buried in the HLA-A*02:01 antigen-binding cleft (FIG. 3d-e), consistent with the peptide binding motif observed (FIG. 2b). P3-Leu/Asp was also buried in the HLA-A*02:01 cleft, further stabilizing the PB1$_{413}$/BHA$_{543}$ peptides, similar to the M1$_{58}$ peptide.

The PB1$_{413}$ peptide has four residues exposed to the solvent, thus available for TCR accessible recognition, namely P4-Ser, P5-Thr, P7-Leu and P8-Gly. Meanwhile, the BHA$_{543}$ peptide has only three exposed residues (P4-Asn, P6-Thr and P8-Leu), as P7-Ile is partially buried. A structural overlay of HLA-A*02:01-presenting M1$_{58}$, PB1$_{413}$ and BHA$_{543}$ peptides showed that the antigen clefts adopted similar conformations (root mean square deviation (r.m.s.d.) of 0.3 Å). However, the PB1$_{413}$ peptide structure overlaid more closely with the M1$_{58}$ peptide than BHA$_{543}$, with a r.m.s.d. of the peptides of 0.5 and 0.7 Å for the Cα atoms, respectively. Indeed, the $PB1_{413}$ structure revealed a flat surface, similar to the $M1_{58}$ peptide, with residues at position 4, 5 and 7 either buried or containing small side chains, and a small hydrophobic P6-Val buried or partially buried, respectively. In contrast, the BHA peptide is presented by HLA-A2 in a conformation that fully exposed the P6-Thr, contains an exposed residue at P4, which has a larger side chain (P4-Asn), and even a mobile P5-His with two alternate conformations modeled.

Overall, both the universal $PB1_{413}$ and IBV-specific $BHA_{543}$ peptides stabilized the HLA-A*02:01 molecule similarly yet formed different pMHC-I landscapes.

Figure 4H:
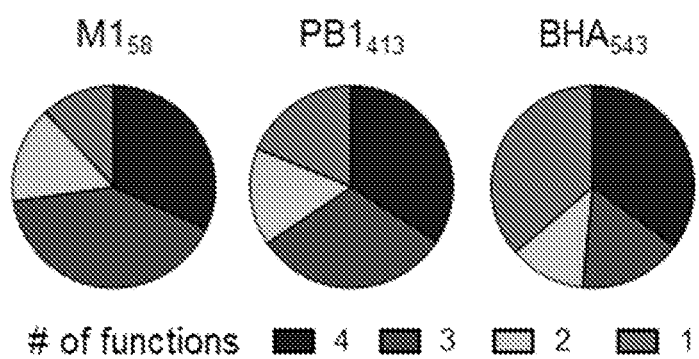
Figure 4I:
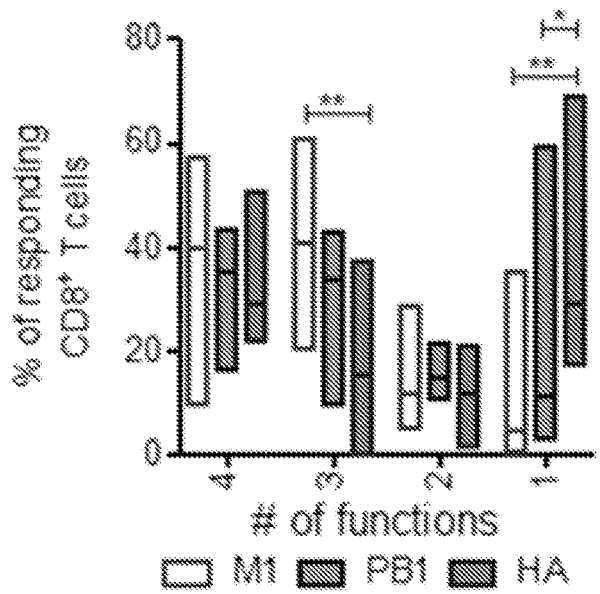
Figure 4J:
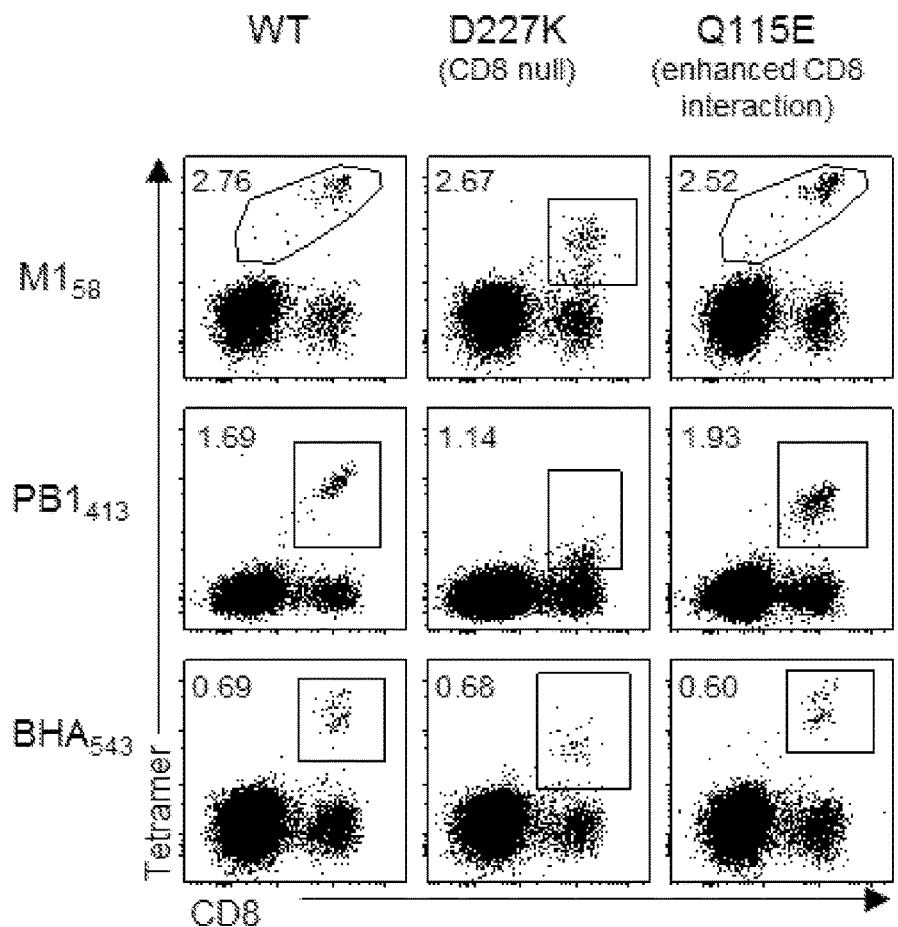
Figure 4K:
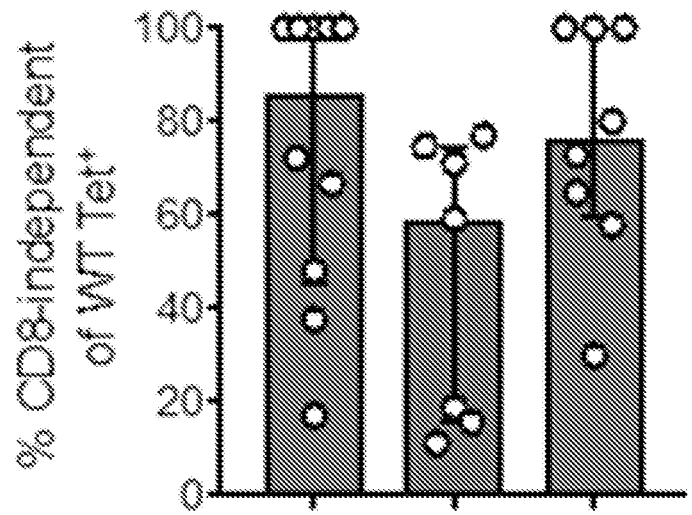
Figure 4L:
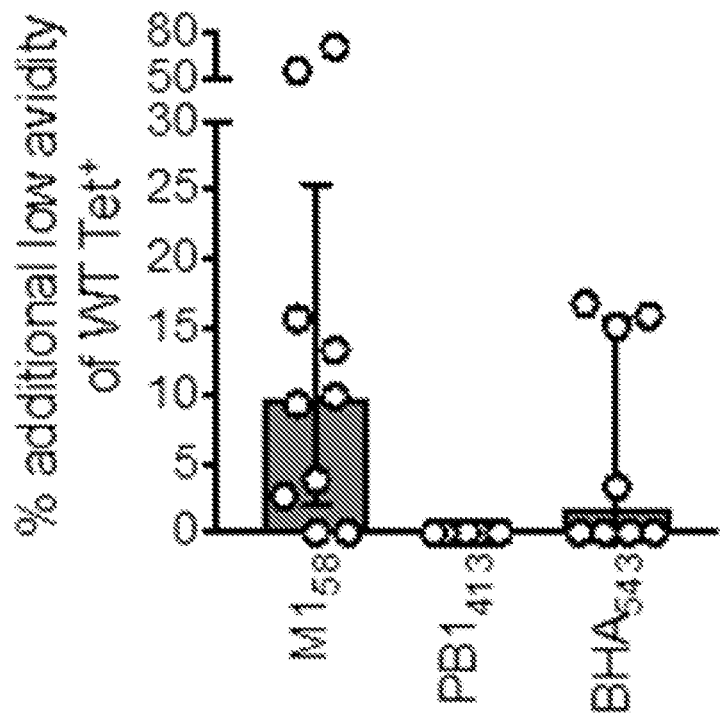

Example 9: High Quality CD8+ T Cell Responses Directed at the Universal and Type-Specific CD8+ T Cell Epitopes As the quality of CD8+ T cell responses can affect anti-viral protection, the functional avidity, pMHC-I/TCR avidity and cytokine polyfunctionality was determined across all three HLA-A*0201-restricted CD8+ T cell epitopes. Both universal $A2/PB1_{413}$ and IBV-A2/$BHA_{543}$CD8+ T cells displayed significantly higher functional avidity than the IAV-A2/$M1_{58}$CD8+ T cell population ($p<0.05$, n=6-9), with EC50 values of 0.89, 0.78 and 8.1 nM, respectively (FIG. 3f,g). IBV-A2/$BHA_{543-551}$+CD8+ T cells were, however, inferior with respect to polyfunctionality, as assessed by simultaneous production of antiviral cytokines (IFNγ, TNF, MIP1β) and a degranulation marker (CD107a) after peptide re-stimulation of expanded T cell lines (FIG. 4h,i). To assess pMHC-I/TCR avidity, we used pMHC-I tetramers with differential abilities to interact with the CD8 co-receptor molecule. While the D227K mutation within MHC-I abrogates CD8 interaction and thus only binds to high avidity TCRs, the Q115E mutation enhances interaction with the CD8 co-receptor, and thus can detect additional low avidity CD8+ T cells. Comparing the frequency of the CD8-null D227K tetramer staining with the WT tetramer, the majority (median 57-82%, n=6-9) of all three CD8+ populations could bind their cognate tetramer independently of the CD8 co-receptor, although with lower intensity (FIG. 4j,k). Based on the Q115E staining, additional CD8+ T cells specific for $A2/M1_{58-66}$ and $A2/BHA_{543-551}$ could be detected, but no additional $A2/PB1_{413-421}$ cells (FIG. 4l). Overall, these data suggest that the universal and novel IBV-specific CD8+ T cells are of high quality, can recognize and respond to their respective epitopes efficiently, although subtle differences occur between $A2/M1_{58}$, $A2/BHA_{543}$ and $A2/PB1_{413}$ CD8+ T cell specificities.

Figure 5A:
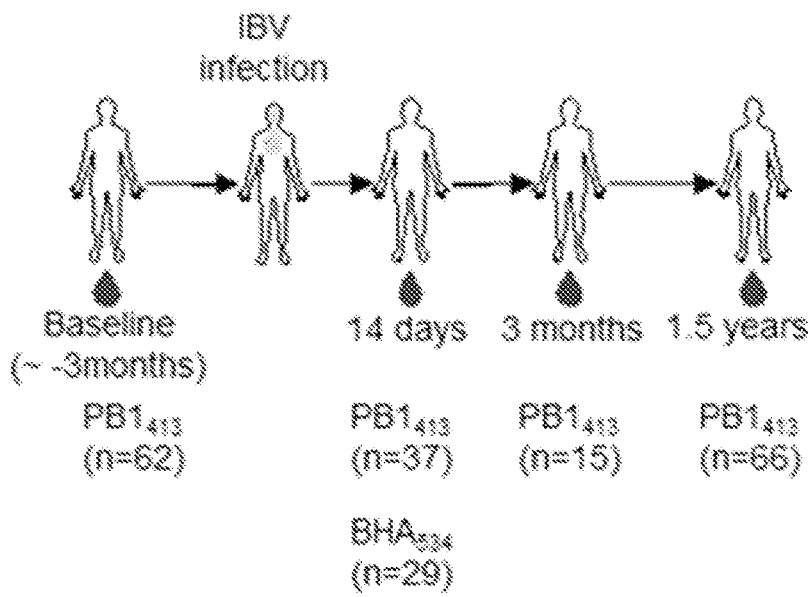
FIG. 5 Single-cell RNA sequencing of universal CD8$^+$ T cells in an IBV-infected individual. (a) Timeline of infection and number of tetramer$^+$CD8$^+$ T cells isolated from each sample. (b) FACS plots and precursor frequency of tetramer$^+$CD8$^+$ T cells prior to, during and after IBV infection. (c) Principal component analysis (PCA) of tetramer$^+$ CD8$^+$ T cells sequenced. Timepoints are distinguished by colour and specificity by shape.
Figure 5B:
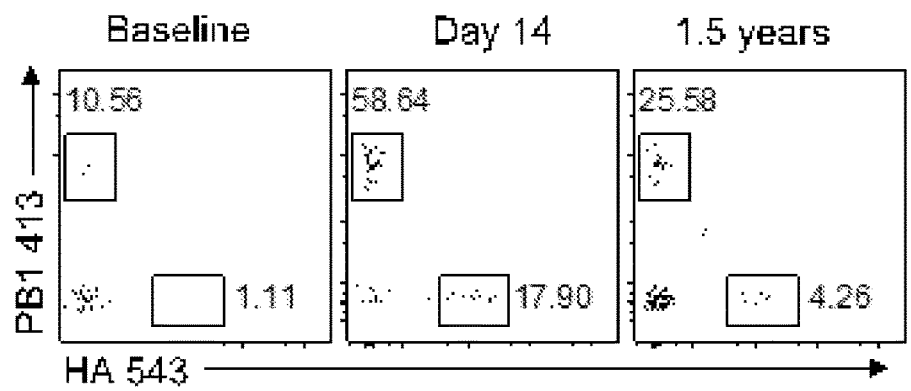
Figure 5B:
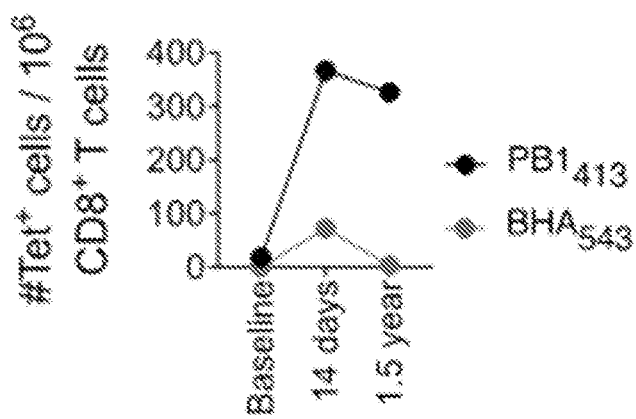

Example 10: Single-Cell RNA Sequencing Analysis of Universal and IBV-Specific CD8+ T Cells To further dissect universal and novel IBV-specific CD8+ T cells at the molecular level during human influenza infection, single-cell RNA sequencing (scRNAseq) was used to assess the transcriptome of ex-vivo isolated tetramer+CD8+ T cells from rare longitudinal PBMC samples obtained from an IBV-infected HLA-A*02:01-expressing individual. Infection with a BNictoria strain was confirmed by PCR and serological analysis. Blood samples were obtained at baseline (~3 months prior to infection), d14, 3 months and 1.5 years after IBV infection (FIG. 5a). Universal $A2/PB1_{413}$+CD8+ T cells were readily detected at baseline at 19 tetramer+/$10^6$ CD8+ T cells, then increased 19-fold to 367 tetramer+/$10^6$ CD8+ T cells on d14 after infection and were maintained at a similar level (327 tetramer+/$10^6$ CD8+ T cells) up to 1.5 years after infection (FIG. 5b). Conversely, $A2/BHA_{543}$+CD8+ T cells were undetectable at the baseline, suggesting this may have been the first IBV infection for this donor, despite a previous immunization against B/Yamagata strains, with an inactivated vaccine not eliciting CD8+ T cell responses[19]. $A2/BHA_{543}$+CD8+ T cells increased to 73.4 tetramer+/$10^6$ CD8+ T cells on d14 after infection, 5-fold lower than universal $A2/PB1_{413}$+CD8+ T cells, and close to the detection level at 1.5-year time-point. Thus, $A2/PB1_{413}$+CD8+ T cells were assessed at all time-points, while IBV-specific $A2/BHA_{543}$+CD8+ T cells were analyzed only on d14.

Figure 5C:
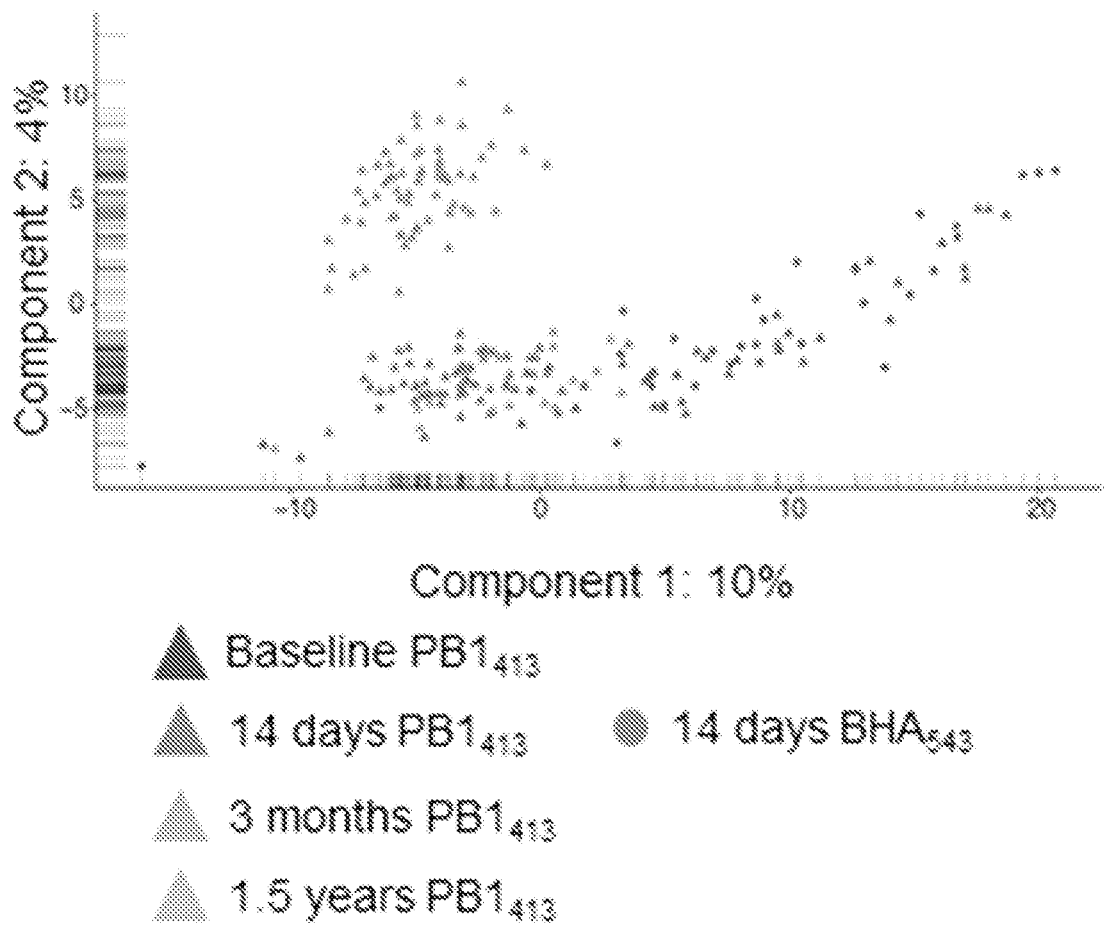

A total of 209 tetramer-positive CD8+ T cells were analyzed using scRNAseq, with an average of 1201 expressed genes identified per cell. Principal component analysis (PCA) revealed clear segregation of $A2/PB1_{413}$+CD8+ T cells by time-point but no segregation between the two antigenic IBV-specificities on d14 (FIG. 5c). Notably, differential expression analysis identified distinct gene expression signatures across time-points (not shown). Specifically, gene-set enrichment analysis revealed signatures of T cell activation and differentiation, cell division, immune cell migration and chemotaxis, which were enriched in d14 cells, as compared to those from baseline or 1.5 years (not shown).

The specific expression of genes associated with T cell differentiation, activation, cytotoxicity and effector function was next analysed. Importantly, effector CD8+ T cells across both IBV-specificities isolated from d14 upregulated genes associated with activation (CD74, CD52), cytotoxic molecules (PRF1, GZMB, GZMA, GZMK, GNLY, CTSW), cytotoxic receptors (NKG7, KLRK1) and effector cytokines (CCL5, CCL4). The expression profiles for some genes associated with differentiation and activation were confirmed by flow-cytometry.

Longitudinal TCRαβ sequences for $A2/PB1_{413}$+CD8+ T cells were then extracted from scRNAseq data using VDZPuzzle. Strikingly, we detected one dominant CDR3αβ clone across all the time-points, accounting for 77.8-100% of the TCRαβ repertoire.

Thus, our scRNAseq data clearly demonstrate dynamic transcriptional changes within the same human TCRαβ clone from baseline to acute and memory time-points. Overall, these data provide evidence on the recruitment of the universal and novel IBV-specific CD8+ T cell effectors during human IBV infection at the transcriptomic level.

Example 11: Restricted TCRαβ Repertoire within $A2/PB1_{413}$+CD8+ T Cells Reflects a Recombination Process of Generating $A2/PB1_{413}$-Specific TCRs The presence of a dominant TCRαβ clonotype in the IBV-infected donor was striking, and as the nature of the TCRαβ repertoire can affect the quality and protective efficacy of CD8+ T cell response, we further investigated TCRαβ repertoires within the universal and IBV-specific CD8+ T cells.

Paired TCRαβ clonotypes within memory $A2/PB1_{413-421}$+CD8+ and $A2/BHA_{543-551}$+CD8+ T cells were dissected using a single-cell multiplex RT-PCR approach from tetramer+CD8+ T cells directly ex vivo. Additionally, paired TCRαβ sequences of $A2/PB1_{413-421}$+CD8+ and $A2/BHA_{543-551}$+CD8+ T cells were extracted and analyzed by scRNAseq. For $A2/PB1_{413-421}$+CD8+ T cells, 89 cells from 5 healthy donors and 69 cells from the baseline, acute and memory time-points of the IBV-infected individual were analysed (FIG. 5a) while for A2/BHA$_{543-551}$-specific CD8$^+$ T cells we analyzed 44 cells from 3 healthy donors and 82 cells from 2 acutely infected individuals. TCR repertoire of universal A2/PB1$_{413}$$^+$CD8$^+$ T cells exhibited substantial enrichment for TRBV11-2 and TRBV12-4, pairing with a variety of TCRα chains. The TCR repertoire of each individual was restricted, evident by the presence of typically one large TCRαβ clonotype and a mean Simpson's Diversity index (SDI) of 0.34, as well as private TCRαβ clonotypes with no overlap at the CDR3α/CDR3β pairs across individuals, even when similar gene usage was observed between individuals. Conversely, the TCRαβ repertoire of A2/BHA$_{543}$$^+$CD8$^+$ T cells exhibited a strong bias for TRBJ2-7 paired with TRBV4-3 and TRAV29/DV5 or TRBV12-4 and TRAV12-2. Despite, these strong biases, observed across all donors, the repertoire was highly diverse at the CDR3α and CDR3β clonotype level and with a mean SDI of 0.8.

Figure 6A:
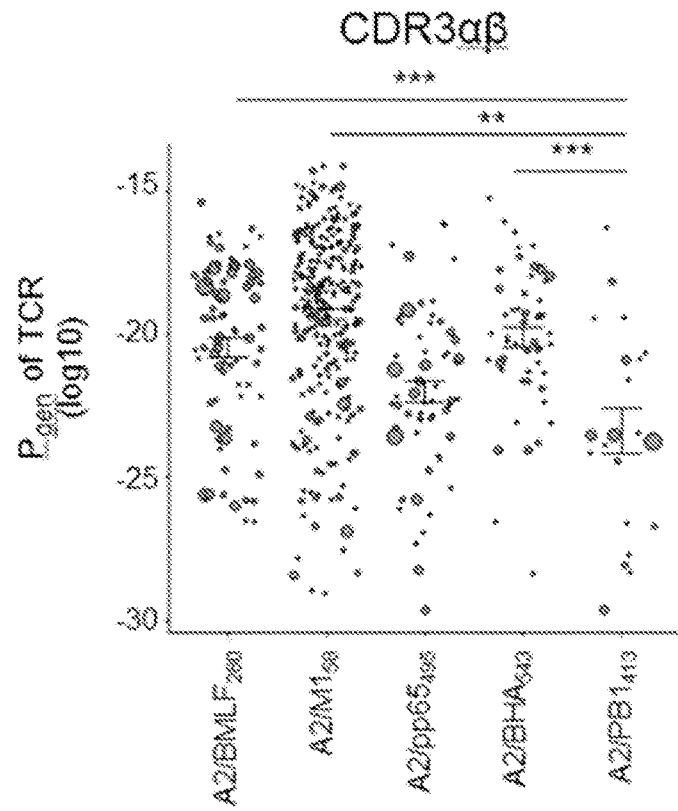
FIG. 6 TCRαβ repertoire of universal and IBV-specific CD8$^+$ T cells. (a) Probability of generating a TCRαβ clonotype for A2/PB1$_{413}$ and A2/BHA$_{543}$ as well as A2/M1$_{58}$ (IAV), A2/BMLF1$_{280}$ (EBV) and A2/pp65$_{495}$ (CMV). P$_{gen}$ was calculated using IGoR. (b) Number of N-insertions found in each TCR clonotype for each specificity, as estimated using TCRdist. (e and f) Error bars indicate SEM.
Figure 6B:
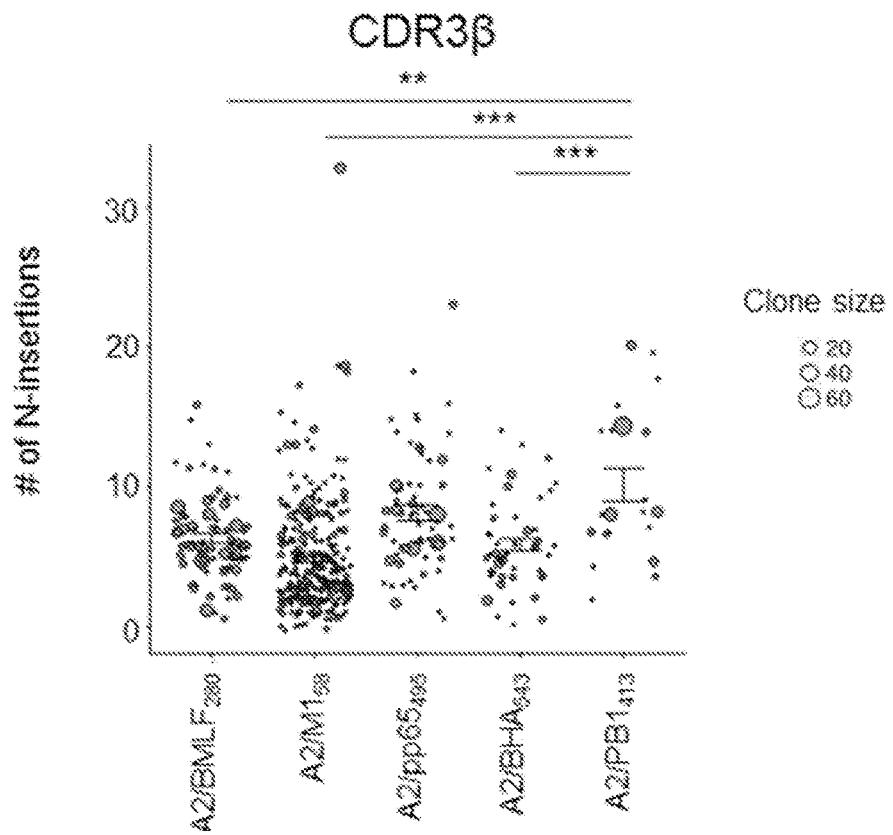

Having defined TCRαβ repertoires, the probability of generating TCRαβ clones specific for the A2/PB1$_{413}$ and A2/BHA$_{543}$ epitopes, as well as for the previously described A2/M1$_{58}$ (IAV), A2/BMLF1$_{280}$ (EBV) and A2/pp65$_{495}$ (CMV) epitopes was calculated using IGoR. The probability of generating an A2/PB1$_{413-421}$-specific TCRαβ was significantly lower (p<0.05) than that for the other T cell specificities, with the exception of the A2/pp65 repertoire (FIG. 6a). Such differences in generation of antigen-specific TCRαβ repertoires were attributed to the TCRβ chain rather than the TCRα chain. As a potential explanation for the lower probability of generating A2/PB1$_{413}$ TCRs, the number of N-insertions in each TCR repertoire was determined. Indeed, the CDR3β sequences of A2/PB1$_{413}$ TCRs contained a significantly (p<0.05) larger number of N-insertions than for the other T cell specificities, again with the exception of the A2/pp65 repertoire (FIG. 6b). No differences were observed between the TCRα chain of A2/PB1$_{413}$ TCRs and other specificities. Despite this lower probability of generating A2/PB1$_{413}$-specific TCRs, the majority of healthy donors in our cohort (80%, n=24) had detectable levels of A2/PB1$_{413}$-specific CD8$^+$ T cells, as measured by peptide-specific T cell lines and/or TAME. Thus, while the TCRαβ repertoire of A2/PB1$_{413}$$^+$CD8$^+$ T cells is highly restricted, reflecting the recombination steps required for generation of these TCRs, the universal PB1$_{413}$$^+$CD8$^+$ T cells are abundant across HLA-A*02:01 individuals and display high proliferative capacity during human influenza infection (FIG. 4e).

Discussion

Cytotoxic CD8$^+$ T cells play a crucial role in protection from severe influenza disease in both human settings and animal models of influenza virus infection. CD8$^+$ T cells limit viral replication and promote clearance of infected cells, the recognition of which is dependent on presentation of viral peptides on the cell surface by MHC-I molecules. The high conservation of these peptides allows cross-recognition of cells infected by distinct IAV strains, including pandemic and avian IAV viruses. This study proposes and examines two levels of cross-reactivity by influenza-specific CD8$^+$ T cells: i) heterotypic cross-reactivity across IAV and IBV, and in some instances ICV, by CD8$^+$ T cells recognizing peptides derived from the most conserved regions of influenza viruses, and ii) IBV-wide cross-reactivity by CD8$^+$ T cells recognizing peptides derived from highly conserved regions of IBV (like BHA$_{543}$ and BNS1$_{266}$).

Cross-reactivity across IAV and IBV is unprecedented for CD8$^+$ T cells and atypical for influenza-specific CD4$^+$ T cells and antibodies. Indeed, only one rare antibody (CR9114) that cross-recognizes a conserved region of the IAV and IBV HA stem regions has been identified and its contribution in the immune response during human infection is unknown. Similarly, a highly conserved CD4$^+$ T cell epitope containing a peptide from the fusion peptide of the HA has been identified but remains poorly characterized. Universal memory A2/PB1$_{413}$ CD8$^+$ T cells, on the other hand, are prominent in human peripheral blood and lung tissues and emerge as activated effector cells during both human IAV and IBV infections. These T cells populations exhibit high polyfunctionality, TCR avidity and antigen sensitivity, at least in vitro, all of which are associated with superior viral control in human infections. Additionally, despite the greater difficulty of generating TCRs specific for the A2/PB1$_{413}$ epitope, such CD8$^+$ T cells were found in the majority (80%) of donors tested, suggesting that such T cell responses are abundant across HLA-A*0201$^+$ donors. The heterotypic cross-reactivity demonstrated by this study is currently restricted to HLA-A*02:01, A*01:01 and B*37:01, which cover ~54% of the world's population.

The IBV-wide cross-reactivity resembles that of IAV-wide cross-reactivity provided by well-characterized CD8$^+$ T cell specificities, exemplified by A2/M1$_{58}$ [3] but also other epitopes. While, the ability of CD8$^+$ T cells to cross-react across the two IBV lineages was previously reported, the antigenic specificity underpinning such cross-reactivity has been unknown. These studies demonstrate that CD8$^+$ T cells target peptides from the BHA and BNS1 proteins and that these responses are protective, as they accelerate viral clearance and reduce inflammatory cytokines in mice. The observation that IBV-wide cross-reactivity can be conferred by peptides derived from the external HA protein is intriguing as it contests the belief that CD8$^+$ T cell cross-reactivity is conferred by peptides from the internal proteins of influenza viruses and contrasts the known immunodominance of responses to M1/NP-derived epitopes from IAV. Whether this is unique to the context of HLA-A2 or common across many HLA alleles during IBV responses is currently unknown. Given the high prevalence of HLA-A*02:01 and the clinical significance of IBV, this work implies that CD8$^+$ T cell-targeting vaccines need to be formulated with broader antigenic specificity not limited to NP and M1 antigens.

The antigenic origin of such broadly cross-reactive epitopes is also of interest. PB1 is the most well-conserved protein across IAV and IBV, with ~60% amino acid identity, as opposed to 30% or less for the other proteins. The PB1$_{413}$ peptide is derived from one of the most well conserved areas of the protein, namely motif B (residues 406-422 of IAV PB1 protein), one of the four core motifs present in viral RNA-dependent polymerases (biswas.) Genome-wide mutational analysis, has shown that IAV cannot tolerate substitutions in these motifs. More interesting, however, is the IBV-wide cross-reactivity conferred by the BHA$_{543}$ peptide. This peptide is derived from the stalk region of the BHA molecule, which shows considerably higher conservation than the HA head domain. Mutagenesis screens in vitro have also revealed limited tolerance to 15-nucleotide insertions of in the BHA molecule, particularly the stalk domain. Thus, these universally cross-reactive CD8$^+$ T cells target epitopes with little sequence flexibility, making them ideal targets for a universal influenza vaccine. Such extensive cross-reactivity across virus genera is uncommon and only resembles that of CD8$^+$ and CD4$^+$ T cells across the subfamily of Alpha-herpseviruses and to a lesser extend CD8$^+$ T cell cross-reactivity across the Flavivirus genus.

Overall, the ability of CD8$^+$ T cells to confer heterotypic cross-reactivity across IAV and IBV and the knowledge of cross-reactive epitopes across IAV/IBV types as well as within IBV, have substantial implications for the design of universal influenza vaccines that do not require annual reformulation. Such vaccines, which likely require the concerted action of both broadly-reactive antibodies and T cells for maximal efficacy, could contribute to protection during annual seasonal epidemics as well as the next inevitable influenza pandemic, regardless of the origin of the infecting influenza virus. Thus, it is critical to consider universal CD8+ T cells, alongside with universal antibodies, for the design of universally cross-reactive influenza vaccines.

Example 11: Screening in PBMCs from Healthy Donors

To further assess the IBV peptides identified in Example 2 and 3, screening for the presence of memory CD8+ T cells in healthy A*02:01+ individuals was performed.

Methods:

Peripheral blood mononuclear cells (PBMC) from healthy A2:01+ donors were cultured in the presence of antigens (10 µM peptide) for 10 days in the presence of IL-2 (10 U/ml). On day 10 PBMCs were stimulated with peptides (1 µM) for 5 hours in the presence of BFA. Cells were surface stained for CD3 and CD8 and intracellularly stained for IFNγ and TNF using the BD cytofix/cytoperm kit according to the manufacturer's instructions (BD Biosciences).

Any pools with positive ICS responses were then dissected to their individual peptides. Consistent with the HHD mice, responses to $HA_{543-551}$ and $NS1_{266-274}$ were detected across multiple donors.

Example 12: Characterization of A24 Responses

Methods:

Peptides naturally presented during IAV infection were identified using immunopeptidomics at 2, 4, 8, 12 and 16 hours post infection (see Example 2).

Class-I reduced (C1R) lymphoblastoid cell lines expressing HLA-A24:02 were used. $10^9$ cells were infected with influenza A (X31) at a multiplicity of infection (moi) of 4 and cells were incubated for 2, 4, 8, 12 and 16 hours. At the aforementioned timepoints, cells were harvested and snap-frozen in $LN_2$.

Cell pellets of 5-15×$10^8$ cells were lysed using a combination of mechanical and detergent based lysis, the lysates cleared by ultracentrifugation, and MHC complexes isolated by immunoaffinity purification using solid-phase bound monoclonal antibodies for immunoaffinity purification as described previously (Dudek et al. 2012).

Anti-MHC-I antibodies antibodies DT9 (anti-HLA-C) and w6/32 were used sequentially for depletion of the endogenous HLA-C*04:01 and purification of the transfected HLA-A*24:02 (and marginal endogenous HLA-B*35:03).

Anti-MHC-II antibodies LB3.1 (anti-HLA-DR), SPV-L3 (anti-HLA-DQ), and B721 (anti-HLA-DP) were subsequently used to isolate MHC class II complexes. Peptides were eluted from the MHC with 10% acetic acid, fractionated on a 4.6 mm internal diameter (i.d.)×100 mm monolithic reversed-phase C18 high-performance liquid chromatography (HPLC) column (Chromolith SpeedROD; Merck Millipore) using an ÄKTAmicro HPLC (GE Healthcare) system, vacuum concentrated, and reconstituted in 0.1% formic acid as described previously (Pymm et al. 2017).

Reconstituted fractions were analysed by Liquid chromatography-tandem mass spectrometry (LC-MS/MS) using a data dependent acquisition strategy either using a Dionex UltiMate 3000 RSLCnano system (Thermo Fisher Scientific) coupled to a Q-Exactive Plus Hybrid Quadrupole Orbitrap (Thermo Fisher Scientific), or a NanoUltra cHiPLC system (Eksigent) coupled to an AB SCIEX 5600+ TripleTOF mass spectrometer as described previously (Pymm et al. 2017).

Spectra were searched against a proteome database consisting of the human proteome (UniProt/Swiss-Prot v2016_04), the B/Malaysia proteome, and a 6 reading frame translation of the B/Malaysia genome, using ProteinPilot software (version 5.0, SCIEX).

Synthetic peptides were purchased from GenScript and dissolved in Hanks Balanced Salt Solution (HBSS) with DMSO. Mice were infected intranasally with 30 µl of influenza viruses diluted in sterile PBS (100 pfu of B/Malaysia for A2 mice).

On day 10 mice were sacrificed and spleens were harvested and processed into single cell suspensions. Splenocytes were stimulated with individual peptides or pools of peptides at a final concentration of 10 µM for 5 hours in the presence of Brefeldin A (BFA). Cells were stained with anti-CD8, anti-IFNγ and anti-TNF antibodies using the BD cytofix/cytoperm kit according to the manufacturer's instructions (BD Biosciences).

Peripheral blood mononuclear cells (PBMC) from healthy A24:02+ donors were cultured in the presence of antigens (10 µM peptide) for 10 days in the presence of IL-2 (10 U/ml). On day 10 PBMCs were stimulated with peptides (1 µM) for 5 hours in the presence of BFA and monenesin. Cells were surface stained for CD3 and CD8 and intracellularly stained for IFNγ and TNF using the BD cytofix/cytoperm kit according to the manufacturer's instructions (BD Biosciences).

Figure 7:
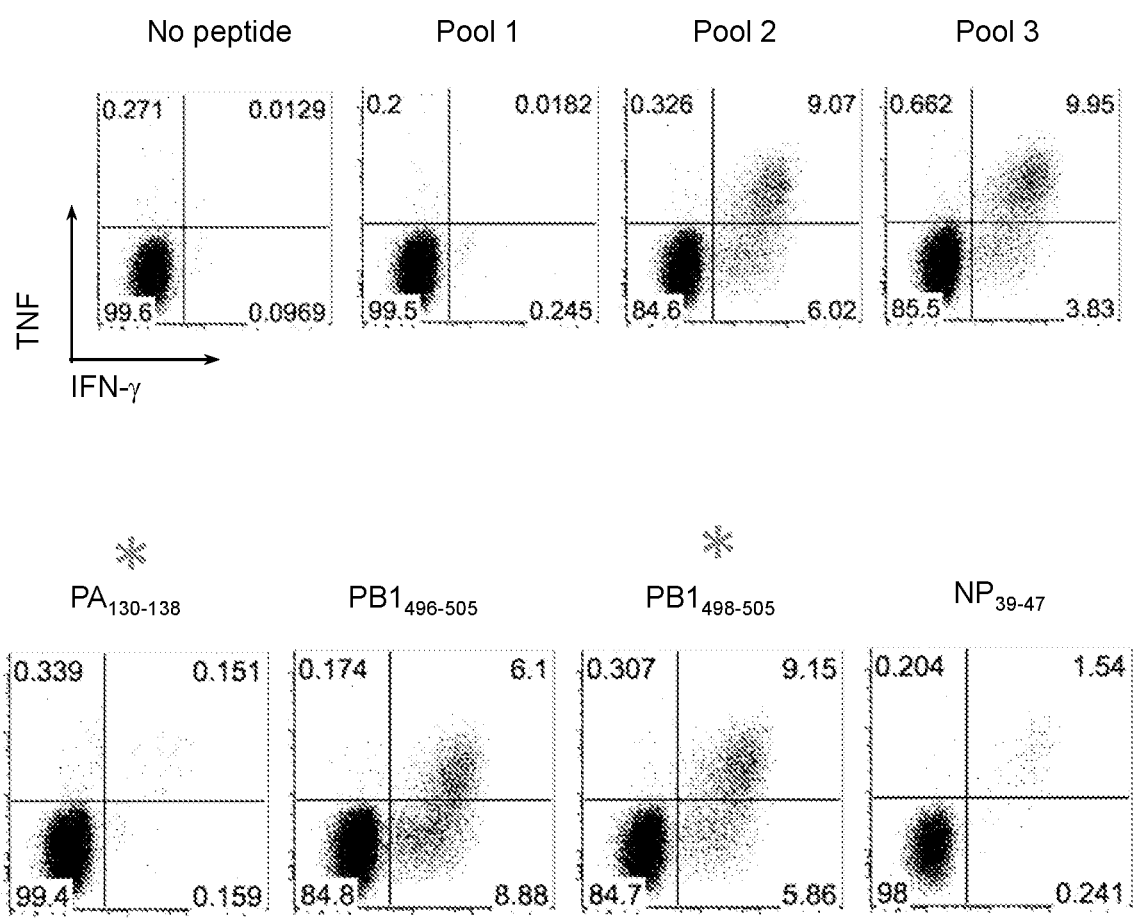
FIGS. 7 and 8 Screening of A*24:02 binding of influenza peptides in A*24:02$^+$ transgenic mice. Peptides were grouped into pools encompassing previously identified A*24:02-binding peptides (FIG. 7 and pools 1, 2 and 3.) Peptides indicated by a red star were found in these studies to be naturally presented following infection), novel peptides naturally presented 16 hours after infection (FIG. 8 and pools 4, 5 and 6), and novel peptides naturally presented 12 hours after infection (pools 7, 8 and 9). In some cases, variants (V) of a particular peptide were included to test for cross-reactivity of responses to natural peptide variants occurring in vaccine and circulating strains of influenza A. CD8$^+$ T cell responses to peptides were measured in the spleen on day 10 post primary infection with influenza A. Data show representative FACS plots for IFNγ and TNF production in response to stimulation with peptide pools, as well as individual peptides found to be immunogenic. Graphed data provides a complete dissection of responses to pools of peptides and individual peptides.
Figure 7:
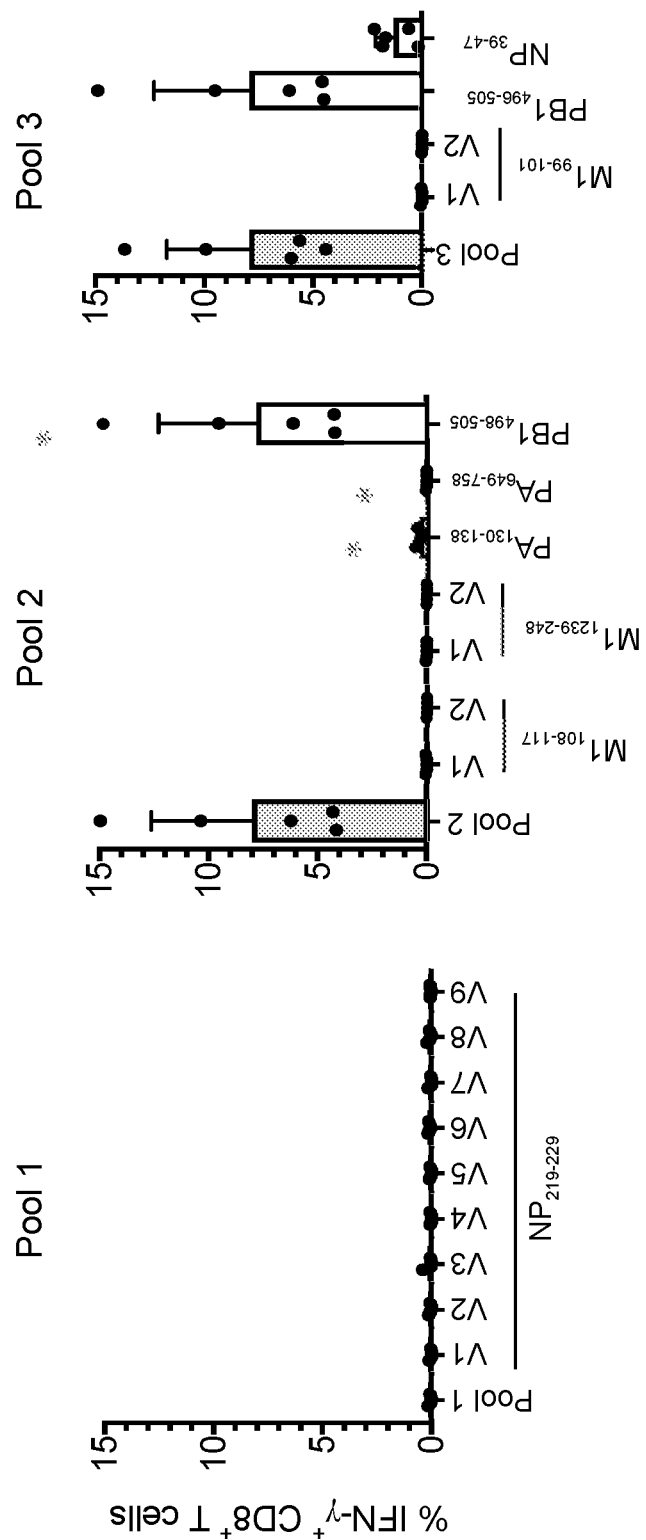
Figure 8:
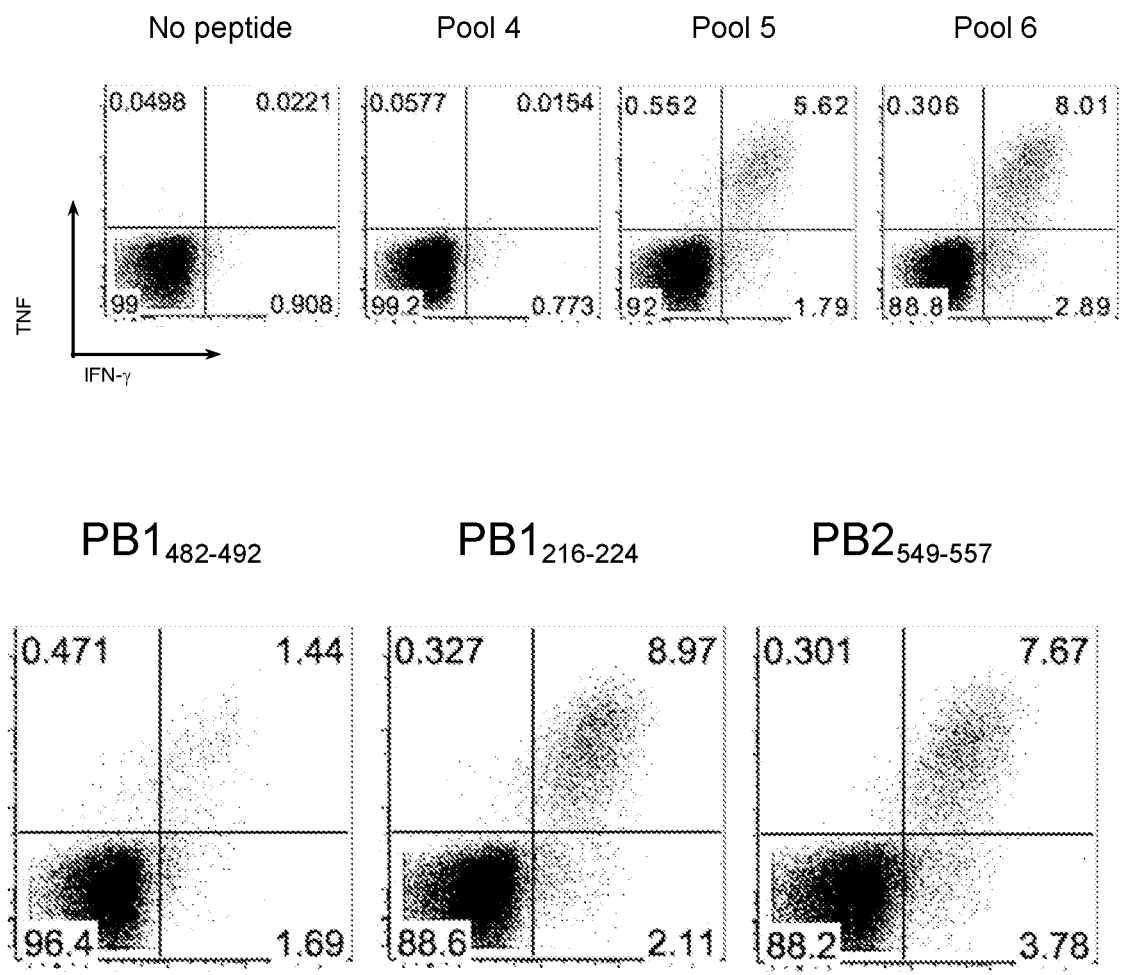
Figure 8:
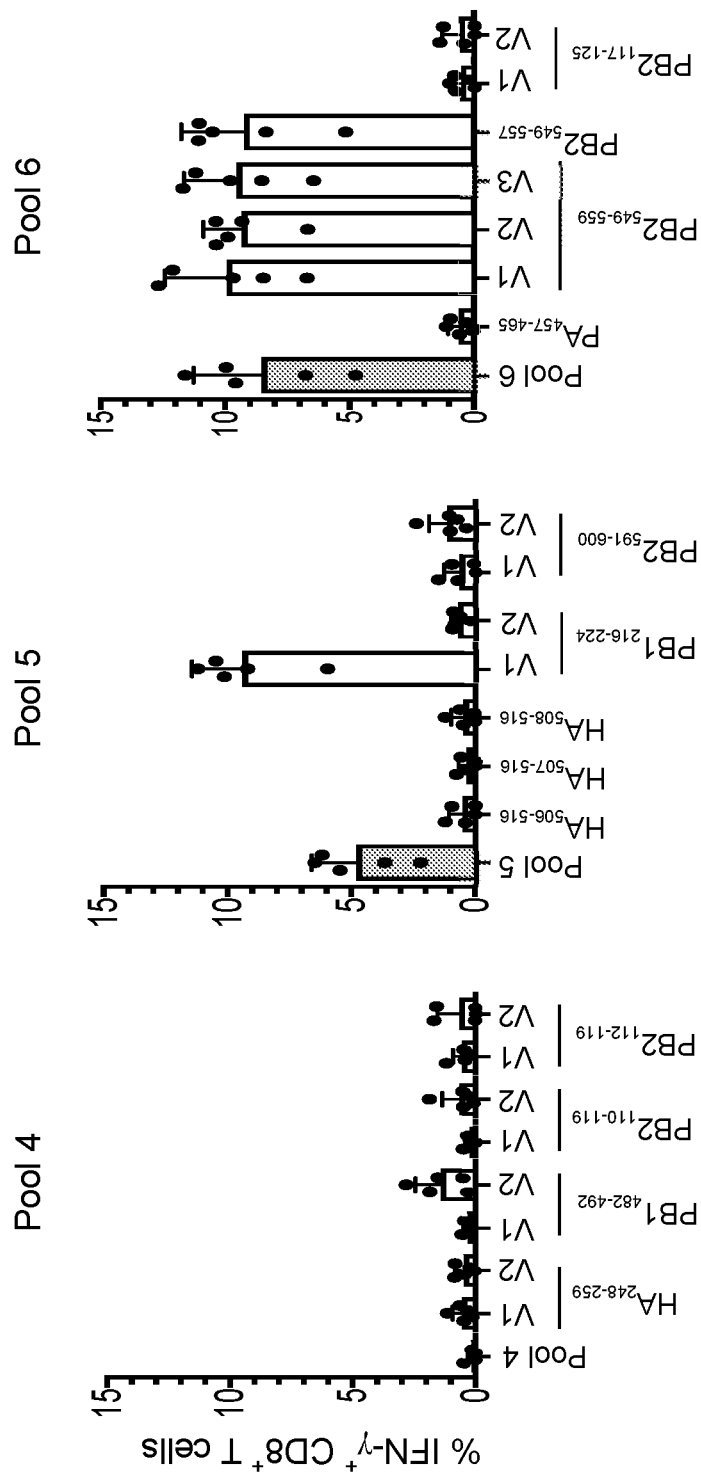
Figure 8:
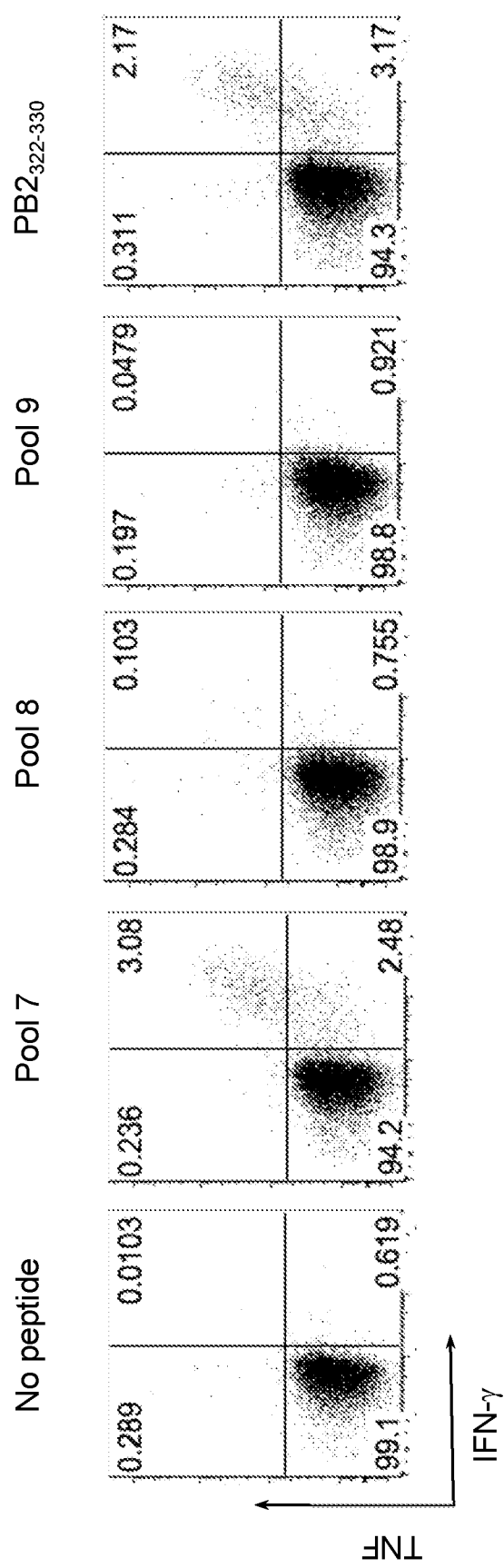
Figure 8:
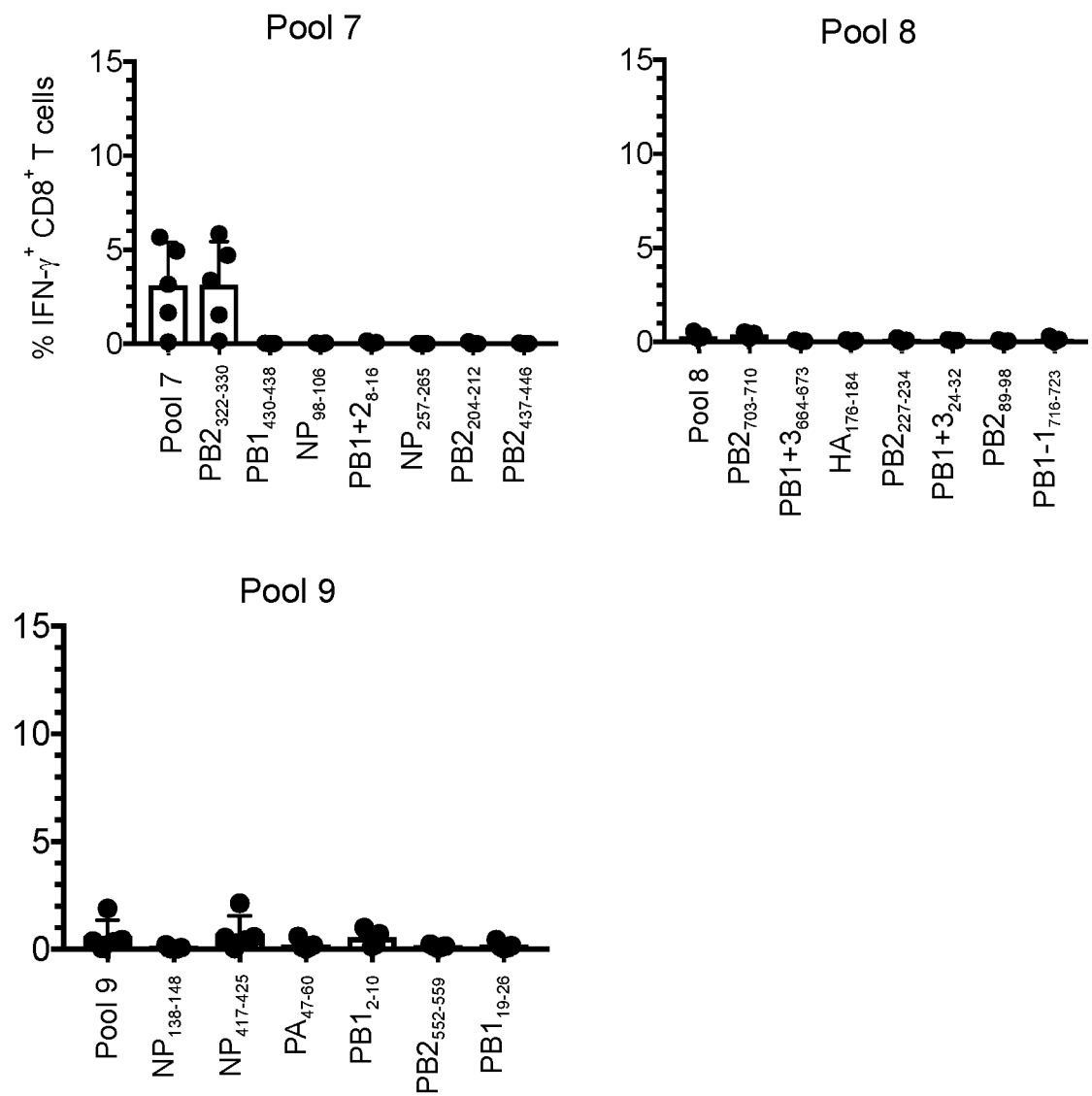

Results:

48 peptides were identified of which, only 3 have been previously reported by others. The previously published (FIG. 7) and newly identified peptides (FIG. 8) were screened in A24 mice to determine their immunogenicity. Mice were infected intranasally with influenza A (x31) and responses to pooled and individual peptides were measured in spenocytes on day 10.

The analysis included variants of epitopes identified from circulating IAV strains (noted as V1, V2 on the figures).

Figure 9:
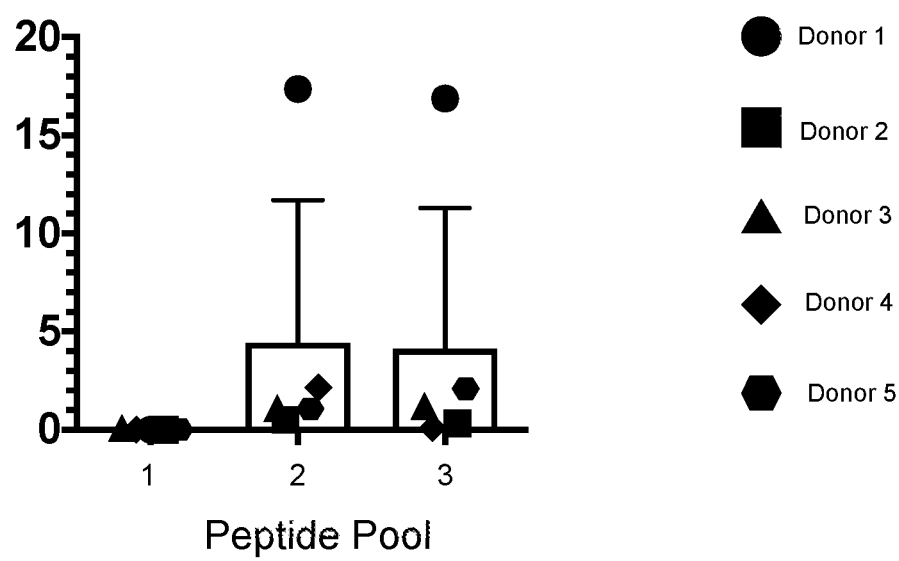
FIG. 9 Responses to HLA-A*24:02-restricted peptides in human A*24:02$^+$ human donors. Screening of previously published A*24:02-binding peptides in human PBMC from healthy donors by ICS. Data show responses to peptide pools 1, 2 and 3, then further dissection of responses to immunogenic peptides in pools 2 and 3. PMA/I stimulation was used as a positive control. Representative plots show A*24:02-PB1$_{498-505}$ tetramer staining as an additional method of confirming the detection of CD8$^+$ T cell responses specific for PB1$_{498-505}$ in donors. The HLA type of each donor is indicated.
Figure 9:
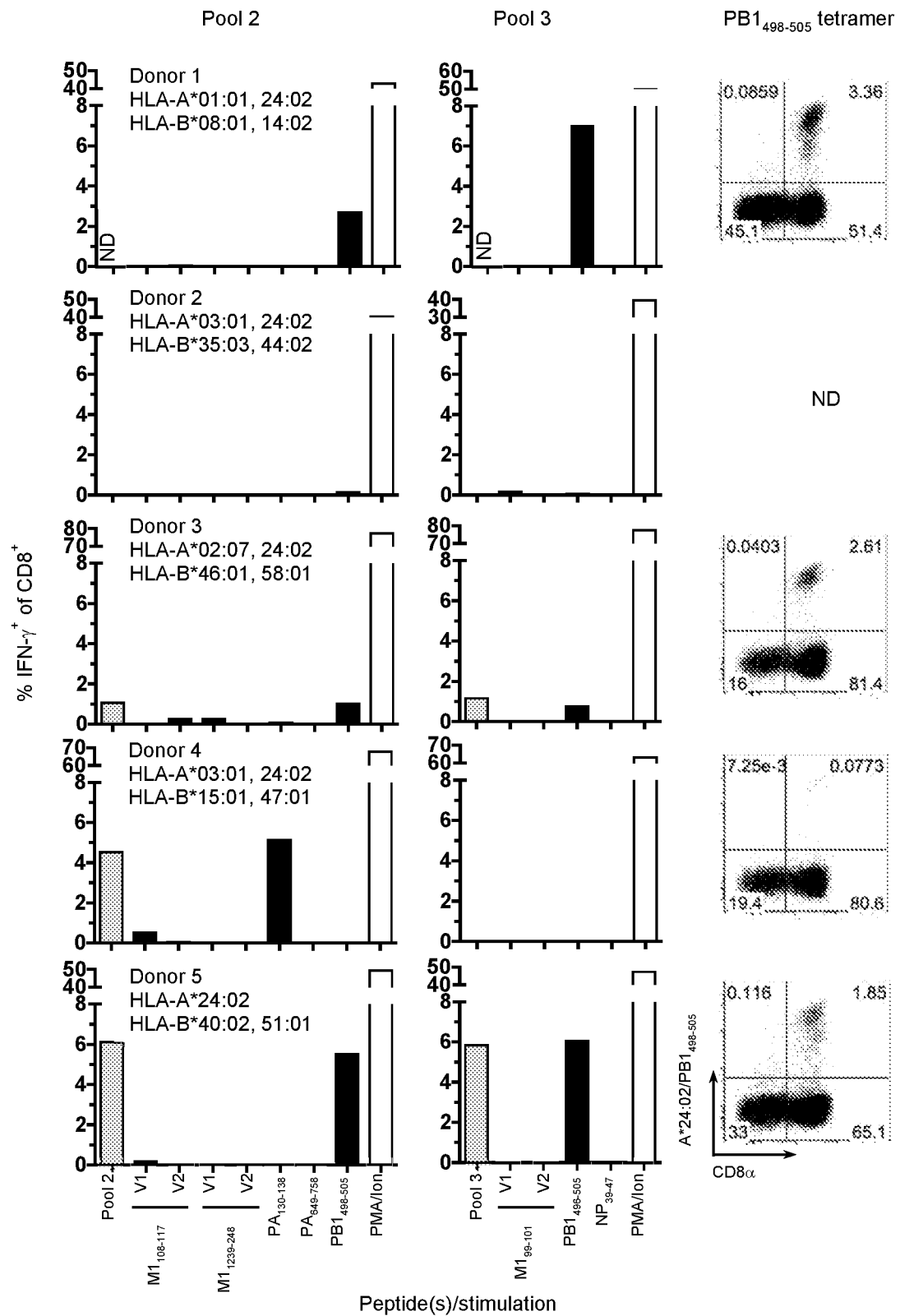
Figure 10:
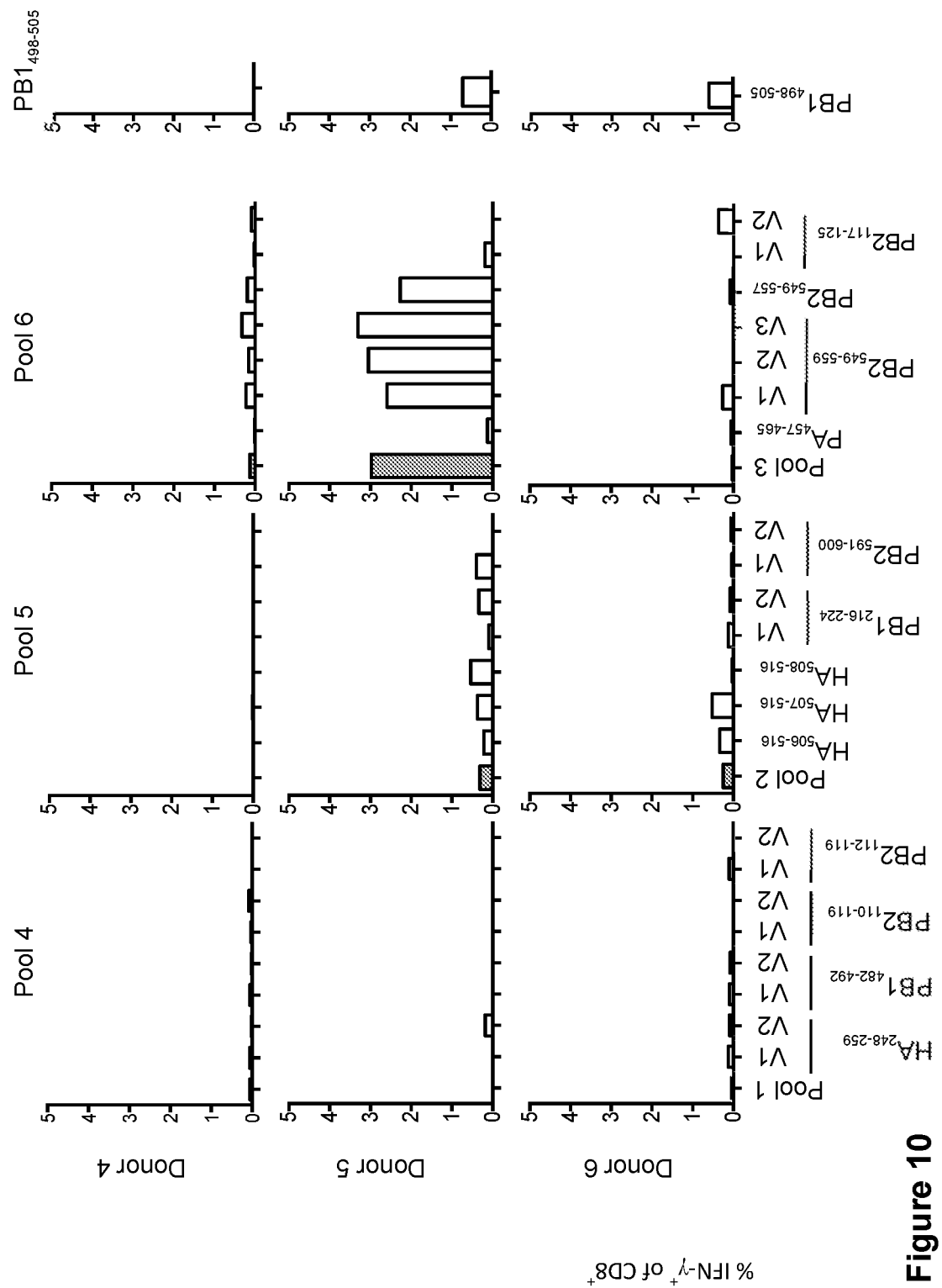
FIG. 10 Responses to novel HLA-A*24:02-presented peptides. Screening of novel peptides in A*24:02$^+$ donors by ICS. Data show responses to peptides in pools 4, 5 and 6, as well as the previously described immunogenic PB1$_{498-505}$ peptide. In some instances, T cell lines could not be established by pool 4 for analysis of responses, reflecting the lack of immunogenic peptides in this pool. The HLA type of each donor is indicated.
Figure 10:
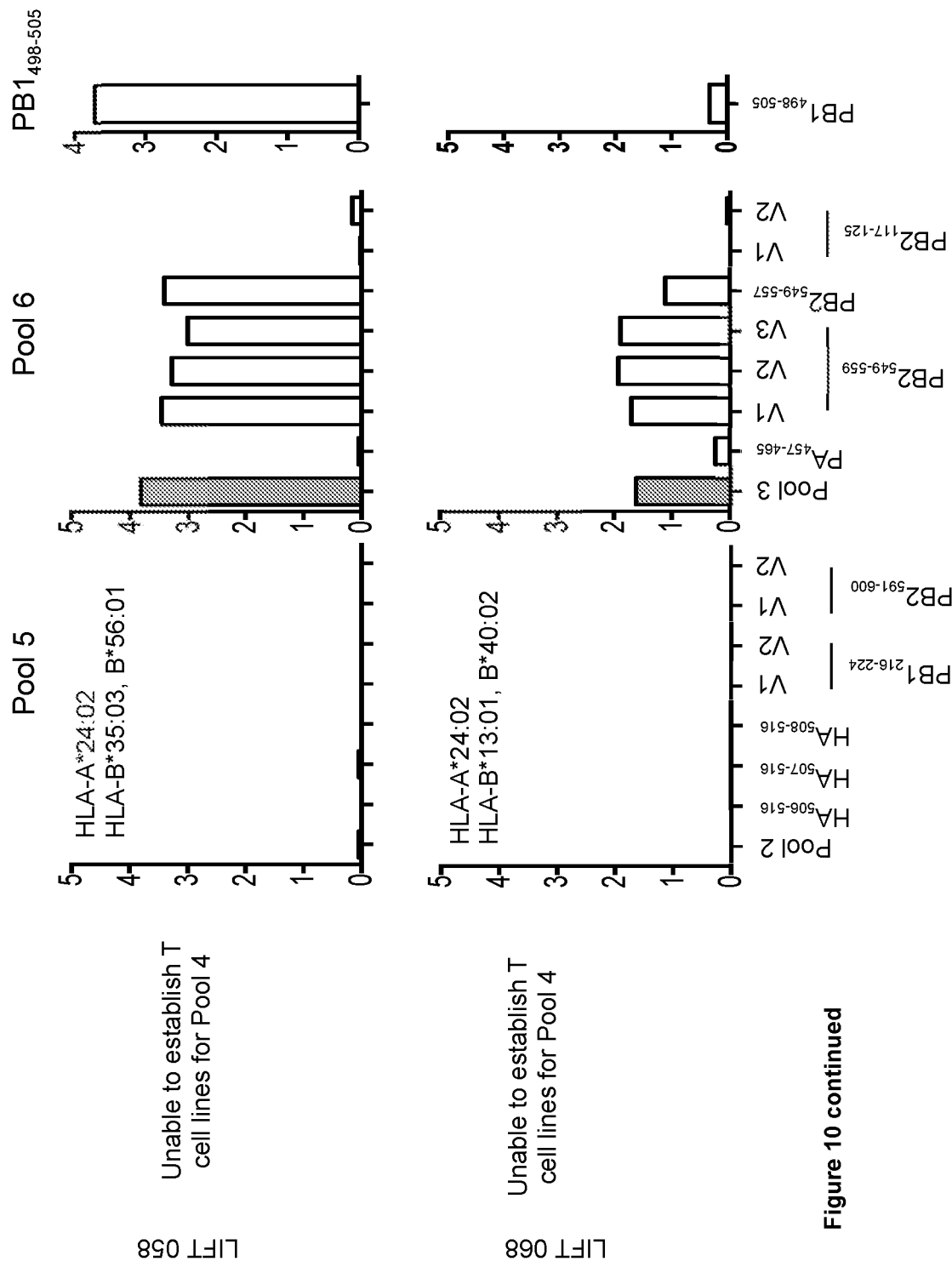
Figure 11:
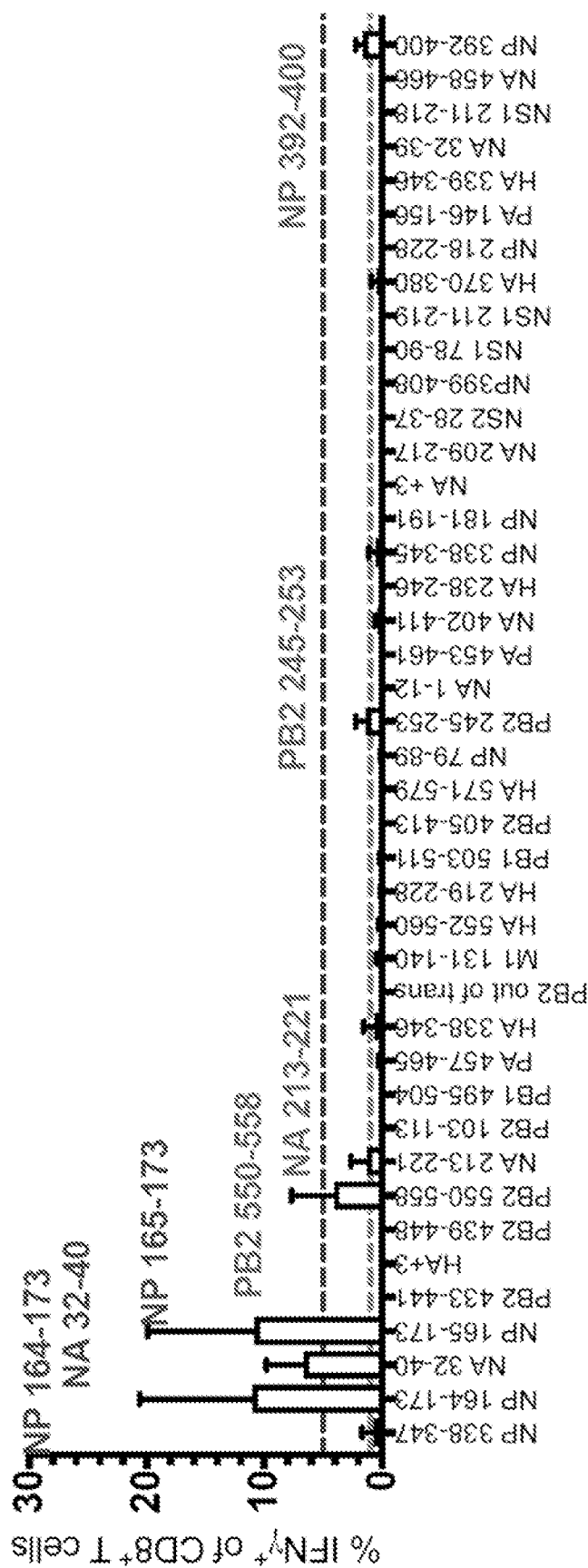
FIG. 11 Identification of novel A24 influenza B epitopes in mice. HLA-A*24:02+ transgenic were infected with 200 pfu of an B/Malaysia and 7 weeks after the primary infection challenged with a heterologous influenza B (B/Phuket). 8 days after secondary infection CD8+ T cell responses to peptides were measured in the spleen. Graphed data provides a complete dissection of the IFNγ expressing CD8+ T cells to individual peptides identified by mass spectrometry.

In vivo responses were shown to be targeted to 7 peptides: $PA_{130-138}$, $PB1_{498-505}$ (and the longer version $PB1_{496-505}$), $NP_{39-47}$, $PB1_{482-492}$, $PB1_{216-224}$, $PB2_{549-557}$, $PB2_{322-330}$. Similar response patterns to the novel and previously published peptides were found in vitro using PBMCs from A24+ donors (FIGS. 9 & 10).

Conclusions

The present studies have identified immunogenic peptides from virus proteins that are not conventionally considered to be source epitopes for CD8+ T cells. For example, the present data indicate that immune responses to influenza B can be driven by recognition of peptides derived from the HA protein. Further, immune responses to influenza A are derived from recognition of peptides from PB1, PB2 and PA proteins.

Example 13: Identification of Immunogenic Peptides for Influenza B (IBV) in HLA-a*24:02+ Mice and/or Indigenous HLA-A*24:02+ Donors Materials and Methods:

Mice=transgenic HLA-A24 mice that were knocked out for the murine class I HLA alleles but knocked in for a chimeric HLA molecule that contains the peptide binding and presentation on the human HLA-A*24:02 but still can bind to the murine T cell coreceptors.

These mice were infected with 200 pfu of an influenza B virus of the Victoria linage and 7 weeks after the primary infection challenged with a heterologous influenza B virus of the Yamagata linage. 8 days after secondary infection the spleen is removed and splenocytes separated using a 40 μm cell strainer.

Splenocytes were stimulated with 1 μM peptides for 5 hrs in presence of protein transport inhibitors. 5 hrs after stimulation, cells are for stained surface markers and internal cytokines. IFNγ and TNFα expression was assessed by Flow cytometry (n=4).

Peripheral blood mononuclear cells (PBMCs) of Indigenous A*24:02+ donors were stimulated with pools of the identified IBV peptides and expanded for 15 days in the presence of IL-2. On day 15, PBMCs were re-stimulated with single peptide pulsed antigen presenting cells for 5 hrs in presence of protein transport inhibitors and cells stained for surface markers and intracellular cytokines. IFNγ and TNFα expression of CD8+ T Lymphocytes was detected by flow cytometry. (n=3)

Results:

42 novel IBV peptides presented by the HLA-A*24:02 were identified. These peptides were screened in A24 mice to determine their immunogenicity (induction of IFNγ production in CD8+ T cells after peptide re-stimulation). These experiments determined 7 immunogenic targets namely: $PB2_{245-253}$, $PB2_{550-558}$, $NP_{164-173}$, $NP_{165-173}$, $NP_{392-400}$, $NA_{32-40}$, and $NA_{213-221}$ (FIG. 11).

In A*24:02+ Indigenous donors, we identified CD8+ T cell responses directed towards an overlapping but not congruent peptide pool. From the peptides immunogenic in mice $PB2_{550-558}$, $NP_{164-173}$, $NP_{165-173}$ and $NA_{32-40}$ showed also an immunogenic potential in Indigenous donors. 3 additional peptides from peptides identified by mass spectrometry showed an immunogenic response, namely $PA_{457-465}$, $HA_{552-560}$ & $PB1_{503}$-511 (FIG. 12).

This study identified the first IBV peptides presented by the HLA-A*24:02 and showed their potential in inducing an immune response in vivo in transgenic mice and in vitro in A*24:02+ Indigenous PBMCs. Given the severe outcome of influenza infections in Indigenous Australians and Indigenous populations in other regions these peptides are of high interest for producing a truly protective vaccine for this high risk group.

The following peptides were identified to be immunogenic.

| Epitope | Sequence | Virus |
|---|---|---|
| $PB2_{245-253}$ | IYHPGGNKL | B |
| $PB2_{550-558}$ | TYQWVLKNL | B |
| $PA_{457-465}$ | KYVLFHTSL | B |
| $NP_{164-173}$ | IYFSPIRVTF | B |
| $NP_{165-473}$ | YFSPIRVTF | B |
| $NP_{392-400}$ | AAYEDLRVL | B |
| $NA_{32-40}$ | LYSDILLKF | B |
| $NA_{213-221}$ | TYHSYANNI | B |
| $HA_{552-560}$ | YYSTAASSL | B |
| $PB1_{503-511}$ | NFAMELPSF | B |

The invention claimed is:

1. A composition comprising at least one peptide, wherein the at least one peptide consists of the amino acid sequence of SEQ ID No: 45.

2. The composition of claim 1, wherein the composition further comprises at least one additional peptide comprising, consisting of or consisting essentially of the amino acid sequence of any one or more of SEQ ID Nos: 14, 6, 9 or 33.

3. The composition of claim 1, wherein the composition further comprises at least one additional peptide comprising, consisting of or consisting essentially of the amino acid sequences of SEQ ID NOs: 25 or 26.

4. The composition of claim 1, wherein the composition further comprises at least one additional peptide comprising, consisting of or consisting essentially of the amino acid sequence of SEQ ID NO: 30.

5. The composition of claim 1, wherein the composition further comprises at least one additional peptide comprising, consisting of or consisting essentially of the amino acid sequence of any one of SEQ ID NOs: 6, 42, and 43.

6. The composition of claim 1, wherein the composition further comprises at least one additional peptide comprising, consisting of or consisting essentially of the amino acid sequence of any one of SEQ ID Nos: 8, 35, 40, 46, 48, 50, 52 and 53.

7. The composition of claim 1, wherein the composition further comprises one or more additional peptides comprising, consisting of or consisting essentially of the amino acid sequence of any one of SEQ ID NOs: 1 to 5, 7, 10 to 13, 15 to 24, 27 to 29, 31, 32, 34, 36 to 39, 41, 43 to 44, 47, 49, or 51.

8. The composition of claim 1, further comprising an adjuvant.

9. The composition of claim 2, further comprising an adjuvant.

10. The composition of claim 2, wherein the at least one additional peptide is at least 60 amino acids in length.

11. A vaccine or immune stimulating composition comprising the composition of claim 2.

12. A vaccine or immune stimulating composition comprising the composition of claim 1.

13. A method of eliciting an immune response in an individual to more than one subtype of influenza, the method comprising administering to the individual a composition of claim 1.

14. A method of immunising an individual in order to prevent an influenza infection or reduce the severity of symptoms of influenza infection in a subject, the method comprising administering to the subject a composition of claim 2.

15. A method of inducing a cytotoxic T cell response in an individual, the method comprising administering to the individual a composition of claim 2.

16. A method of inducing a cytotoxic T cell response in an individual, the method comprising administering to the individual a composition of claim 2.

17. A method of eliciting an immune response in an individual to more than one subtype of influenza, the method comprising administering to the individual a composition of claim 2.

18. A method of immunising an individual in order to prevent an influenza infection or reduce the severity of symptoms of influenza infection in a subject, the method comprising administering to the subject a composition of claim 1.

* * * * *

SEQUENCE LISTING

```
<160> NUMBER OF SEQ ID NOS: 53

<210> SEQ ID NO 1
<211> LENGTH: 9
<212> TYPE: PRT
<213> ORGANISM: Influenza A virus

<400> SEQUENCE: 1

Asn Leu Pro Phe Asp Arg Thr Thr Ile
1               5

<210> SEQ ID NO 2
<211> LENGTH: 9
<212> TYPE: PRT
<213> ORGANISM: Influenza A virus

<400> SEQUENCE: 2

Asp Val Asn Pro Thr Leu Leu Phe Leu
1               5

<210> SEQ ID NO 3
<211> LENGTH: 9
<212> TYPE: PRT
<213> ORGANISM: Influenza A virus

<400> SEQUENCE: 3
```

```
Ser Phe Ser Phe Gly Gly Phe Thr Phe
1               5

<210> SEQ ID NO 4
<211> LENGTH: 8
<212> TYPE: PRT
<213> ORGANISM: Influenza A virus

<400> SEQUENCE: 4

Arg Tyr Gly Pro Ala Leu Ser Ile
1               5

<210> SEQ ID NO 5
<211> LENGTH: 14
<212> TYPE: PRT
<213> ORGANISM: Influenza B virus

<400> SEQUENCE: 5

Ser Leu Asn Asp Asp Gly Leu Asp Asn His Thr Ile Leu Leu
1               5                   10

<210> SEQ ID NO 6
<211> LENGTH: 9
<212> TYPE: PRT
<213> ORGANISM: Influenza B virus

<400> SEQUENCE: 6

Gly Leu Asp Asn His Thr Ile Leu Leu
1               5

<210> SEQ ID NO 7
<211> LENGTH: 11
<212> TYPE: PRT
<213> ORGANISM: Influenza B virus

<400> SEQUENCE: 7

Val Leu Ser Gln Phe Gly Gln Glu His Arg Leu
1               5                   10

<210> SEQ ID NO 8
<211> LENGTH: 9
<212> TYPE: PRT
<213> ORGANISM: Influenza B virus

<400> SEQUENCE: 8

Ser Gln Phe Gly Gln Glu His Arg Leu
1               5

<210> SEQ ID NO 9
<211> LENGTH: 9
<212> TYPE: PRT
<213> ORGANISM: Influenza B virus

<400> SEQUENCE: 9

Tyr Glu Asp Leu Arg Val Leu Ser Ala
1               5

<210> SEQ ID NO 10
<211> LENGTH: 10
<212> TYPE: PRT
<213> ORGANISM: Influenza B virus

<400> SEQUENCE: 10

Lys Leu Leu Gly Ile Asn Met Ser Lys Lys
1               5                   10
```

```
<210> SEQ ID NO 11
<211> LENGTH: 9
<212> TYPE: PRT
<213> ORGANISM: Influenza B virus

<400> SEQUENCE: 11

Gly Pro Ala Thr Ala Gln Thr Ala Ile
1               5

<210> SEQ ID NO 12
<211> LENGTH: 8
<212> TYPE: PRT
<213> ORGANISM: Influenza B virus

<400> SEQUENCE: 12

Arg Asp Gly Phe Val Ser Asn Phe
1               5

<210> SEQ ID NO 13
<211> LENGTH: 10
<212> TYPE: PRT
<213> ORGANISM: Influenza B virus

<400> SEQUENCE: 13

Phe Tyr Arg Asp Gly Phe Val Ser Asn Phe
1               5                   10

<210> SEQ ID NO 14
<211> LENGTH: 9
<212> TYPE: PRT
<213> ORGANISM: Influenza B virus

<400> SEQUENCE: 14

Val Ala Asp Gly Gly Pro Asn Ile Tyr
1               5

<210> SEQ ID NO 15
<211> LENGTH: 8
<212> TYPE: PRT
<213> ORGANISM: Influenza B virus

<400> SEQUENCE: 15

Phe Glu Phe Thr Ser Met Phe Tyr
1               5

<210> SEQ ID NO 16
<211> LENGTH: 9
<212> TYPE: PRT
<213> ORGANISM: Influenza B virus

<400> SEQUENCE: 16

Arg Arg Ala Ile Ala Thr Ala Gly Ile
1               5

<210> SEQ ID NO 17
<211> LENGTH: 9
<212> TYPE: PRT
<213> ORGANISM: Influenza B virus

<400> SEQUENCE: 17

Cys Glu Asn Leu Glu Gln Ser Gly Leu
1               5
```

<210> SEQ ID NO 18
<211> LENGTH: 10
<212> TYPE: PRT
<213> ORGANISM: Influenza B virus

<400> SEQUENCE: 18

Gly Met Phe Glu Phe Thr Ser Met Phe Tyr
1               5                   10

<210> SEQ ID NO 19
<211> LENGTH: 9
<212> TYPE: PRT
<213> ORGANISM: Influenza B virus

<400> SEQUENCE: 19

Asp Thr Val Ile Arg Thr His Glu Tyr
1               5

<210> SEQ ID NO 20
<211> LENGTH: 10
<212> TYPE: PRT
<213> ORGANISM: Influenza C virus

<400> SEQUENCE: 20

Lys Leu Ile Gly Ile Asn Met Ser Leu Glu
1               5                   10

<210> SEQ ID NO 21
<211> LENGTH: 9
<212> TYPE: PRT
<213> ORGANISM: Influenza C virus

<400> SEQUENCE: 21

Ser Pro Ser Thr Ala Leu Met Ala Leu
1               5

<210> SEQ ID NO 22
<211> LENGTH: 9
<212> TYPE: PRT
<213> ORGANISM: Influenza C virus

<400> SEQUENCE: 22

Arg Arg Ala Ile Ala Thr Pro Gly Met
1               5

<210> SEQ ID NO 23
<211> LENGTH: 9
<212> TYPE: PRT
<213> ORGANISM: Influenza C virus

<400> SEQUENCE: 23

Cys Glu Lys Leu Lys Glu Ser Gly Leu
1               5

<210> SEQ ID NO 24
<211> LENGTH: 8
<212> TYPE: PRT
<213> ORGANISM: Influenza C virus

<400> SEQUENCE: 24

Phe Glu Phe Thr Ser Met Phe Phe
1               5

<210> SEQ ID NO 25
<211> LENGTH: 9

```
<212> TYPE: PRT
<213> ORGANISM: Influenza virus

<400> SEQUENCE: 25

Asn Met Leu Ser Thr Val Leu Gly Val
1               5

<210> SEQ ID NO 26
<211> LENGTH: 10
<212> TYPE: PRT
<213> ORGANISM: Influenza virus

<400> SEQUENCE: 26

Phe Asn Met Leu Ser Thr Val Leu Gly Val
1               5                   10

<210> SEQ ID NO 27
<211> LENGTH: 9
<212> TYPE: PRT
<213> ORGANISM: Influenza A virus

<400> SEQUENCE: 27

Tyr Tyr Leu Glu Lys Ala Asn Lys Ile
1               5

<210> SEQ ID NO 28
<211> LENGTH: 9
<212> TYPE: PRT
<213> ORGANISM: Influenza A virus

<400> SEQUENCE: 28

Ser Tyr Leu Ile Arg Ala Leu Thr Leu
1               5

<210> SEQ ID NO 29
<211> LENGTH: 11
<212> TYPE: PRT
<213> ORGANISM: Influenza A virus

<400> SEQUENCE: 29

Ser Tyr Ile Asn Arg Thr Gly Thr Phe Glu Phe
1               5                   10

<210> SEQ ID NO 30
<211> LENGTH: 9
<212> TYPE: PRT
<213> ORGANISM: Influenza A virus

<400> SEQUENCE: 30

Thr Tyr Gln Trp Ile Ile Arg Asn Trp
1               5

<210> SEQ ID NO 31
<211> LENGTH: 11
<212> TYPE: PRT
<213> ORGANISM: Influenza A virus

<400> SEQUENCE: 31

Thr Tyr Gln Trp Ile Ile Arg Asn Trp Glu Thr
1               5                   10

<210> SEQ ID NO 32
<211> LENGTH: 10
<212> TYPE: PRT
<213> ORGANISM: Influenza A virus
```

<400> SEQUENCE: 32

Lys Leu Val Gly Ile Asn Met Ser Lys Lys
1               5                   10

<210> SEQ ID NO 33
<211> LENGTH: 9
<212> TYPE: PRT
<213> ORGANISM: Influenza A virus

<400> SEQUENCE: 33

Phe Glu Asp Leu Arg Val Leu Ser Ala
1               5

<210> SEQ ID NO 34
<211> LENGTH: 9
<212> TYPE: PRT
<213> ORGANISM: Influenza A virus

<400> SEQUENCE: 34

Gly Pro Ala Thr Ala Gln Met Ala Leu
1               5

<210> SEQ ID NO 35
<211> LENGTH: 8
<212> TYPE: PRT
<213> ORGANISM: Influenza A virus

<400> SEQUENCE: 35

Arg Tyr Gly Phe Val Ala Asn Phe
1               5

<210> SEQ ID NO 36
<211> LENGTH: 9
<212> TYPE: PRT
<213> ORGANISM: Influenza A virus

<400> SEQUENCE: 36

Arg Arg Ala Ile Ala Thr Pro Gly Met
1               5

<210> SEQ ID NO 37
<211> LENGTH: 9
<212> TYPE: PRT
<213> ORGANISM: Influenza A virus

<400> SEQUENCE: 37

Cys Glu Lys Leu Glu Gln Ser Gly Leu
1               5

<210> SEQ ID NO 38
<211> LENGTH: 10
<212> TYPE: PRT
<213> ORGANISM: Influenza A virus

<400> SEQUENCE: 38

Gly Thr Phe Glu Phe Thr Ser Phe Phe Tyr
1               5                   10

<210> SEQ ID NO 39
<211> LENGTH: 9
<212> TYPE: PRT
<213> ORGANISM: Influenza A virus

<400> SEQUENCE: 39

Asp Thr Val Asn Arg Thr His Gln Tyr
1               5

<210> SEQ ID NO 40
<211> LENGTH: 9
<212> TYPE: PRT
<213> ORGANISM: Influenza A virus

<400> SEQUENCE: 40

Val Ser Asp Gly Gly Pro Asn Leu Tyr
1               5

<210> SEQ ID NO 41
<211> LENGTH: 8
<212> TYPE: PRT
<213> ORGANISM: Influenza A virus

<400> SEQUENCE: 41

Phe Glu Phe Thr Ser Phe Phe Tyr
1               5

<210> SEQ ID NO 42
<211> LENGTH: 9
<212> TYPE: PRT
<213> ORGANISM: Influenza A virus

<400> SEQUENCE: 42

Gly Ile Leu Gly Phe Val Phe Val Leu
1               5

<210> SEQ ID NO 43
<211> LENGTH: 9
<212> TYPE: PRT
<213> ORGANISM: Influenza B virus

<400> SEQUENCE: 43

Tyr Leu Asn Pro Gly Asn Tyr Ser Met
1               5

<210> SEQ ID NO 44
<211> LENGTH: 9
<212> TYPE: PRT
<213> ORGANISM: Influenza B virus

<400> SEQUENCE: 44

Ile Tyr His Pro Gly Gly Asn Lys Leu
1               5

<210> SEQ ID NO 45
<211> LENGTH: 9
<212> TYPE: PRT
<213> ORGANISM: Influenza B virus

<400> SEQUENCE: 45

Thr Tyr Gln Trp Val Leu Lys Asn Leu
1               5

<210> SEQ ID NO 46
<211> LENGTH: 9
<212> TYPE: PRT
<213> ORGANISM: Influenza B virus

<400> SEQUENCE: 46

Lys Tyr Val Leu Phe His Thr Ser Leu

<210> SEQ ID NO 47
<211> LENGTH: 10
<212> TYPE: PRT
<213> ORGANISM: Influenza B virus

<400> SEQUENCE: 47

Ile Tyr Phe Ser Pro Ile Arg Val Thr Phe
1               5                   10

<210> SEQ ID NO 48
<211> LENGTH: 9
<212> TYPE: PRT
<213> ORGANISM: Influenza B virus

<400> SEQUENCE: 48

Tyr Phe Ser Pro Ile Arg Val Thr Phe
1               5

<210> SEQ ID NO 49
<211> LENGTH: 9
<212> TYPE: PRT
<213> ORGANISM: Influenza B virus

<400> SEQUENCE: 49

Ala Ala Tyr Glu Asp Leu Arg Val Leu
1               5

<210> SEQ ID NO 50
<211> LENGTH: 9
<212> TYPE: PRT
<213> ORGANISM: Influenza B virus

<400> SEQUENCE: 50

Leu Tyr Ser Asp Ile Leu Leu Lys Phe
1               5

<210> SEQ ID NO 51
<211> LENGTH: 9
<212> TYPE: PRT
<213> ORGANISM: Influenza B virus

<400> SEQUENCE: 51

Thr Tyr His Ser Tyr Ala Asn Asn Ile
1               5

<210> SEQ ID NO 52
<211> LENGTH: 9
<212> TYPE: PRT
<213> ORGANISM: Influenza B virus

<400> SEQUENCE: 52

Tyr Tyr Ser Thr Ala Ala Ser Ser Leu
1               5

<210> SEQ ID NO 53
<211> LENGTH: 9
<212> TYPE: PRT
<213> ORGANISM: Influenza B virus

<400> SEQUENCE: 53

Asn Phe Ala Met Glu Leu Pro Ser Phe
1               5